US008912157B2

(12) United States Patent
Collard et al.

(10) Patent No.: US 8,912,157 B2
(45) Date of Patent: Dec. 16, 2014

(54) TREATMENT OF PANCREATIC DEVELOPMENTAL GENE RELATED DISEASES BY INHIBITION OF NATURAL ANTISENSE TRANSCRIPT TO A PANCREATIC DEVELOPMENTAL GENE

(75) Inventors: Joseph Collard, Delray Beach, FL (US); Olga Khorkova Sherman, Tequesta, FL (US)

(73) Assignee: CuRNA, Inc.

( * ) Notice: Subject to any disclaimer, the term of this patent is extended or adjusted under 35 U.S.C. 154(b) by 109 days.

(21) Appl. No.: 13/520,496

(22) PCT Filed: Jan. 6, 2011

(86) PCT No.: PCT/US2011/020321
§ 371 (c)(1),
(2), (4) Date: Jul. 3, 2012

(87) PCT Pub. No.: WO2011/085066
PCT Pub. Date: Jul. 14, 2011

(65) Prior Publication Data
US 2012/0322853 A1 Dec. 20, 2012

Related U.S. Application Data

(60) Provisional application No. 61/292,508, filed on Jan. 6, 2010, provisional application No. 61/294,129, filed on Jan. 12, 2010, provisional application No. 61/297,863, filed on Jan. 25, 2010, provisional application No. 61/297,847, filed on Jan. 25, 2010, provisional application No. 61/323,027, filed on Apr. 12, 2010.

(51) Int. Cl.
*A61K 48/00* (2006.01)
*C12N 15/113* (2010.01)
*A61K 31/7088* (2006.01)

(52) U.S. Cl.
CPC ......... *A61K 31/7088* (2013.01); *C12N 2310/11* (2013.01); *C12N 15/113* (2013.01)
USPC .......................... 514/44; 536/24.5; 536/23.1

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 5,034,506 A | 7/1991 | Summerton et al. |
| 5,138,045 A | 8/1992 | Cook et al. |
| 5,218,105 A | 6/1993 | Cook et al. |
| 5,288,512 A | 2/1994 | Seiden |
| 5,288,514 A | 2/1994 | Ellman |
| 5,319,080 A | 6/1994 | Leumann |
| 5,393,878 A | 2/1995 | Leumann |
| 5,432,272 A | 7/1995 | Benner et al. |
| 5,457,189 A | 10/1995 | Crooke et al. |
| 5,459,255 A | 10/1995 | Cook et al. |
| 5,474,796 A | 12/1995 | Brennan |
| 5,491,084 A | 2/1996 | Chalfie et al. |
| 5,506,337 A | 4/1996 | Summerton et al. |
| 5,519,134 A | 5/1996 | Acevedo et al. |
| 5,525,735 A | 6/1996 | Gallop et al. |
| 5,539,083 A | 7/1996 | Cook et al. |
| 5,549,974 A | 8/1996 | Holmes |
| 5,569,588 A | 10/1996 | Ashby et al. |
| 5,576,302 A | 11/1996 | Cook et al. |
| 5,593,853 A | 1/1997 | Chen et al. |
| 5,605,662 A | 2/1997 | Heller et al. |
| 5,661,134 A | 8/1997 | Cook et al. |
| 5,708,161 A | 1/1998 | Reese |
| 5,739,119 A | 4/1998 | Galli et al. |
| 5,739,311 A | 4/1998 | Lackey et al. |
| 5,756,710 A | 5/1998 | Stein et al. |
| 5,849,902 A | 12/1998 | Arrow et al. |
| 5,891,725 A | 4/1999 | Soreq et al. |
| 5,902,880 A | 5/1999 | Thompson |
| 5,908,779 A | 6/1999 | Carmichael et al. |
| 5,965,721 A | 10/1999 | Cook et al. |
| 5,985,663 A | 11/1999 | Bennett et al. |
| 6,005,095 A | 12/1999 | Capaccioli et al. |
| 6,013,639 A | 1/2000 | Peyman et al. |
| 6,013,786 A | 1/2000 | Chen et al. |
| 6,034,233 A | 3/2000 | Ecker et al. |
| 6,100,090 A | 8/2000 | Monia et al. |

(Continued)

FOREIGN PATENT DOCUMENTS

| | | |
|---|---|---|
| CA | 2686933 | 4/2008 |
| EP | 335451 A3 | 3/1988 |

(Continued)

OTHER PUBLICATIONS

Czauderna et al. Nucleic Acid Research 31:2705-2716, 2003).*
Ausubel, Current Protocols in Molecular Biology vol. 1, 1994, 6.0.1-6.4.10.
Barak, et al., "A β-Arrestin/Green Fluorescent Protein Biosensor for Detecting G Protein-Coupled Receptor Activation," J. Biol. Chem. 272:27497-27500 (1997).
Barber, et al., "Delivery of membrane-impermeant fluorescent probes into living neural cell populations by lipotransfer," Neuroscience Letters 207:17-20 (1996).
Baum, "Solid-phase synthesis of benzodiazepines," C&EN News, Jan. 18, p. 33-34 (1993).

(Continued)

*Primary Examiner* — Kimberly Chong
(74) *Attorney, Agent, or Firm* — CuRNA, Inc.; Monte R. Browder

(57) ABSTRACT

The present invention relates to antisense oligonucleotides that modulate the expression of and/or function of a Pancreatic Developmental gene, in particular, by targeting natural antisense polynucleotides of a Pancreatic Developmental gene. The invention also relates to the identification of these antisense oligonucleotides and their use in treating diseases and disorders associated with the expression of Pancreatic Developmental genes.

15 Claims, 5 Drawing Sheets

(56) References Cited

U.S. PATENT DOCUMENTS

| | | |
|---|---|---|
| 6,140,492 A | 10/2000 | Morelli et al. |
| 6,147,200 A | 11/2000 | Manoharan et al. |
| 6,165,712 A | 12/2000 | Foulkes et al. |
| 6,165,990 A | 12/2000 | Singh et al. |
| 6,175,409 B1 | 1/2001 | Nielsen et al. |
| 6,221,587 B1 | 4/2001 | Ecker et al. |
| 6,239,265 B1 | 5/2001 | Cook |
| 6,242,589 B1 | 6/2001 | Cook et al. |
| 6,268,490 B1 | 7/2001 | Imanishi et al. |
| 6,303,374 B1 | 10/2001 | Zhang et al. |
| 6,307,040 B1 | 10/2001 | Cook et al. |
| 6,316,198 B1 | 11/2001 | Skouv et al. |
| 6,335,434 B1 | 1/2002 | Guzaev et al. |
| 6,376,541 B1 | 4/2002 | Nixon et al. |
| 6,403,566 B1 | 6/2002 | Wang |
| 6,444,464 B1 | 9/2002 | Wyatt |
| 6,451,991 B1 | 9/2002 | Martin et al. |
| 6,525,191 B1 | 2/2003 | Ramassamy |
| 6,528,262 B1 | 3/2003 | Gilad et al. |
| 6,528,631 B1 | 3/2003 | Cook et al. |
| 6,617,122 B1 | 9/2003 | Hayden et al. |
| 6,617,442 B1 | 9/2003 | Crooke et al. |
| 6,630,315 B1 | 10/2003 | Miwa et al. |
| 6,639,059 B1 | 10/2003 | Kochkine et al. |
| 6,656,730 B1 | 12/2003 | Manoharan |
| 6,667,337 B2 | 12/2003 | Wilson |
| 6,670,461 B1 | 12/2003 | Bennett et al. |
| 6,710,174 B2 | 3/2004 | Bennett et al. |
| 6,734,291 B2 | 5/2004 | Kochkine et al. |
| 6,762,169 B1 | 7/2004 | Manoharan |
| 6,794,499 B2 | 9/2004 | Wengel et al. |
| 6,833,361 B2 | 12/2004 | Hong et al. |
| 6,861,514 B2 | 3/2005 | Cook et al. |
| 6,867,294 B1 | 3/2005 | Sanghvi et al. |
| 6,936,467 B2 | 8/2005 | Kmiec et al. |
| 6,936,593 B1 | 8/2005 | Agrawal et al. |
| 6,977,295 B2 | 12/2005 | Belotserkovskii et al. |
| 6,986,988 B2 | 1/2006 | Gilad et al. |
| 7,034,133 B2 | 4/2006 | Wengel et al. |
| 7,034,145 B2 | 4/2006 | Shen et al. |
| 7,053,195 B1 | 5/2006 | Goff |
| 7,053,199 B2 | 5/2006 | Imanishi et al. |
| 7,053,207 B2 | 5/2006 | Wengel |
| 7,060,809 B2 | 6/2006 | Wengel et al. |
| 7,084,125 B2 | 8/2006 | Wengel |
| 7,087,589 B2 | 8/2006 | Jacobson et al. |
| 7,125,982 B1 | 10/2006 | Frayne |
| 7,144,995 B2 | 12/2006 | Wise et al. |
| 7,144,999 B2 | 12/2006 | Ward et al. |
| 7,148,204 B2 | 12/2006 | Bennett et al. |
| 7,153,954 B2 | 12/2006 | Koch et al. |
| 7,169,916 B2 | 1/2007 | Krotz et al. |
| 7,199,107 B2 | 4/2007 | Dobie et al. |
| 7,202,357 B2 | 4/2007 | Crooke et al. |
| 7,217,572 B2 | 5/2007 | Ward et al. |
| 7,220,549 B2 | 5/2007 | Buzby |
| 7,226,785 B2 | 6/2007 | Kmiec et al. |
| 7,229,974 B2 | 6/2007 | Peyman et al. |
| 7,229,976 B2 | 6/2007 | Dobie et al. |
| 7,235,534 B2 | 6/2007 | Tanguay et al. |
| 7,235,653 B2 | 6/2007 | Bennett et al. |
| 7,238,858 B2 | 7/2007 | Marraccini et al. |
| 7,276,599 B2 | 10/2007 | Moore et al. |
| 7,285,288 B1 | 10/2007 | Tormo et al. |
| 7,297,786 B2 | 11/2007 | McCray et al. |
| 7,314,923 B2 | 1/2008 | Kaneko et al. |
| 7,320,965 B2 | 1/2008 | Sah et al. |
| 7,321,828 B2 | 1/2008 | Cowsert et al. |
| 7,335,764 B2 | 2/2008 | Crooke et al. |
| 7,335,765 B2 | 2/2008 | Kaneko et al. |
| 7,339,051 B2 | 3/2008 | Crooke et al. |
| 7,371,833 B1 | 5/2008 | Weiss |
| 7,399,845 B2 | 7/2008 | Seth et al. |
| 7,402,434 B2 | 7/2008 | Newman et al. |
| 7,402,574 B2 | 7/2008 | Iversen et al. |
| 7,420,050 B2 | 9/2008 | Park et al. |
| 7,423,142 B2 | 9/2008 | Vornlocher |
| 7,425,545 B2 | 9/2008 | Crooke et al. |
| 7,427,675 B2 | 9/2008 | Capaldi et al. |
| 7,456,154 B2 | 11/2008 | Soreq et al. |
| 7,462,642 B2 | 12/2008 | Wang et al. |
| 7,468,431 B2 | 12/2008 | Bhanot et al. |
| 7,510,830 B2 | 3/2009 | Baguley et al. |
| 7,541,344 B2 | 6/2009 | Bhat et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,582,745 B2 | 9/2009 | Sah et al. |
| 7,585,893 B2 | 9/2009 | Baguley et al. |
| 7,589,190 B2 | 9/2009 | Westergaard et al. |
| 7,598,227 B2 | 10/2009 | Crooke et al. |
| 7,605,251 B2 | 10/2009 | Tan et al. |
| 7,622,453 B2 | 11/2009 | Frieden et al. |
| 7,662,948 B2 | 2/2010 | Kurreck et al. |
| 7,666,854 B2 | 2/2010 | Seth et al. |
| 7,674,895 B2 | 3/2010 | Reich et al. |
| 7,687,617 B2 | 3/2010 | Thrue et al. |
| 7,691,995 B2 | 4/2010 | Zamore et al. |
| 7,695,902 B2 | 4/2010 | Crooke |
| 7,696,345 B2 | 4/2010 | Allerson et al. |
| 7,709,456 B2 | 5/2010 | Corey et al. |
| 7,709,630 B2 | 5/2010 | Gaarde et al. |
| 7,713,738 B2 | 5/2010 | Hansen et al. |
| 7,718,629 B2 | 5/2010 | Bamcrot et al. |
| 7,723,508 B2 | 5/2010 | Crooke et al. |
| 7,732,422 B2 | 6/2010 | Gleave et al. |
| 7,732,590 B2 | 6/2010 | Bhanot et al. |
| 7,737,264 B2 | 6/2010 | Thrue et al. |
| 7,737,265 B2 | 6/2010 | Akinc et al. |
| 7,741,305 B2 | 6/2010 | Crooke et al. |
| 7,741,309 B2 | 6/2010 | Hansen et al. |
| 7,741,457 B2 | 6/2010 | Seth et al. |
| 7,745,609 B2 | 6/2010 | Bennett et al. |
| 7,749,978 B2 | 7/2010 | Sah et al. |
| 8,110,674 B2 * | 2/2012 | Manoharan et al. ......... 536/24.5 |
| 2003/0139359 A1 | 7/2003 | Dobie |
| 2003/0186920 A1 | 10/2003 | Sirois |
| 2003/0191075 A1 | 10/2003 | Cook et al. |
| 2003/0228618 A1 | 12/2003 | Levanon et al. |
| 2003/0233670 A1 | 12/2003 | Edgerton et al. |
| 2004/0006031 A1 | 1/2004 | Dean et al. |
| 2004/0033480 A1 | 2/2004 | Wong |
| 2004/0101858 A1 | 5/2004 | Ward et al. |
| 2004/0137423 A1 | 7/2004 | Hayden et al. |
| 2004/0138155 A1 | 7/2004 | Baird et al. |
| 2004/0175803 A1 | 9/2004 | Meritet et al. |
| 2004/0180336 A1 | 9/2004 | Gilad et al. |
| 2004/0254137 A1 | 12/2004 | Ackermann et al. |
| 2005/0009771 A1 | 1/2005 | Levanon et al. |
| 2005/0026160 A1 | 2/2005 | Allerson et al. |
| 2005/0113326 A1 | 5/2005 | Siwkowski et al. |
| 2005/0143357 A1 | 6/2005 | Pousette et al. |
| 2005/0153286 A1 | 7/2005 | Clements |
| 2005/0215504 A1 | 9/2005 | Bennett et al. |
| 2005/0222029 A1 | 10/2005 | Bartel et al. |
| 2006/0009410 A1 | 1/2006 | Crooke et al. |
| 2006/0142196 A1 | 6/2006 | Klein et al. |
| 2006/0178333 A1 | 8/2006 | Soreq et al. |
| 2007/0082848 A1 | 4/2007 | Alitalo et al. |
| 2007/0197459 A1 | 8/2007 | Milner |
| 2007/0213274 A1 | 9/2007 | Salonen |
| 2007/0213292 A1 | 9/2007 | Stoffel et al. |
| 2007/0248590 A1 | 10/2007 | Milne et al. |
| 2008/0146788 A1 | 6/2008 | Bhat et al. |
| 2008/0221051 A1 | 9/2008 | Becker et al. |
| 2008/0293142 A1 | 11/2008 | Liu et al. |
| 2009/0191263 A1 | 7/2009 | Reich et al. |
| 2009/0192106 A1 | 7/2009 | Dobie et al. |
| 2009/0208479 A1 | 8/2009 | Jaye et al. |
| 2009/0258925 A1 | 10/2009 | Wahlestedt |
| 2009/0318536 A1 | 12/2009 | Freier et al. |

(56) References Cited

U.S. PATENT DOCUMENTS

| | | |
|---|---|---|
| 2009/0326041 A1 | 12/2009 | Bhanot et al. |
| 2010/0105760 A1 | 4/2010 | Collard et al. |

FOREIGN PATENT DOCUMENTS

| | | |
|---|---|---|
| EP | 335451 A2 | 10/1989 |
| WO | WO-84/03564 | 9/1984 |
| WO | WO-91/19733 | 12/1991 |
| WO | WO-92/00091 | 1/1992 |
| WO | WO-92/08796 | 5/1992 |
| WO | WO-93/20242 | 10/1993 |
| WO | WO-94-26887 A1 | 11/1994 |
| WO | WO-94/28143 | 12/1994 |
| WO | WO-95-15373 A2 | 6/1995 |
| WO | WO-95/22618 | 8/1995 |
| WO | WO-95/25116 | 10/1995 |
| WO | WO-95/35505 | 12/1995 |
| WO | WO-96-27663 A2 | 9/1996 |
| WO | WO-97-39120 A1 | 10/1997 |
| WO | WO-99-14226 A1 | 3/1999 |
| WO | WO-99-39352 A1 | 8/1999 |
| WO | WO-00-57837 A1 | 10/2000 |
| WO | WO-00-61770 A2 | 10/2000 |
| WO | WO-01-00669 A2 | 1/2001 |
| WO | WO-01-21631 A2 | 3/2001 |
| WO | WO-01-25488 A2 | 4/2001 |
| WO | WO-01-51630 A1 | 7/2001 |
| WO | WO-02-062840 A1 | 8/2002 |
| WO | WO-02-068688 A1 | 9/2002 |
| WO | WO-2004-016255 A1 | 2/2004 |
| WO | WO-2004-024079 A2 | 3/2004 |
| WO | WO-2004-030750 A1 | 4/2004 |
| WO | WO-2004-041838 A1 | 5/2004 |
| WO | WO-2004- 104161 A2 | 12/2004 |
| WO | WO 2005-045034 A2 | 5/2005 |
| WO | WO-2005-070136 A2 | 8/2005 |
| WO | WO 2005-079862 A1 | 9/2005 |
| WO | WO-2007-028065 A2 | 3/2007 |
| WO | WO-2007-071182 A1 | 6/2007 |
| WO | WO 2007-087113 A2 | 8/2007 |
| WO | WO-2007-138023 A1 | 12/2007 |
| WO | WO-2008-057556 A2 | 5/2008 |
| WO | WO 2008-066672 A2 | 6/2008 |
| WO | WO-2008-087561 A2 | 7/2008 |
| WO | WO-2010-002984 A1 | 1/2010 |
| WO | WO-2010-040571 A2 | 4/2010 |
| WO | WO-2010-054364 A1 | 5/2010 |
| WO | WO-2010-058227 A2 | 5/2010 |

OTHER PUBLICATIONS

Bernstein, E., et al., "Role for a bidentate ribonuclease in the initiation step of RNA interference," Nature 409:363 (2001).
Boutla, A., et al., "Short 5'-phosphorylated double-stranded RNAs induce RNA interference in *Drosophila*," Curr. Biol. 11:1776-1780 (2001).
Boyd-Kimball. et al., "Proteomic Identification of Proteins Specifically Oxidized by Intracerebral Injection of Amyloid β-Peptide (1-42) into Rat Brain: Implications for Alzheimer's Disease," Neuroscience 132, 313-324 (2005).
Brazma & Vilo, "Gene expression data analysis," FEBS Lett., 480;17-24 (2000).
Bright, et al., "Chapter 6. Fluorescence Ratio Imaging Microscopy," Methods in Cell Biology vol. 30, Taylor and Wang (eds) p. 157-192 (1989).
Bright, et al., "Delivery of Macromolecules Into Adherent Cells via Electroporation for Use in Fluorescence Spectroscopic Imaging and Metabolic Studies," Cytometry 24:226-233 (1996).
Bright, et al., "Fluorescence Ratio Imaging Microscopy: Temporal and Spatial Measurements of Cytoplasmic pH," J. Cell Biology 104:1019-1033 (1987).
Campbell, et al., "Phosphonmate Ester Synthesis Using a Modified Mitsunobu Condensation," J. Org. Chem. 59:658-660 (1994).

Caplen, N. J., et al., "Specific inhibition of gene expression by small double-stranded RNAs in invertebrate and vertebrate systems," PNAS Sci. USA 98:9742-9747 (2001).
Carninci, et al., "The transcriptional landscape of the mammalian genome," Science 309:1559-1563 (2005).
Carulli, et al., "High Throughput Analysis of Differential Gene Expression," J. Cell Biochem. Suppl., 3:286-296 (1998).
Celis, et al., "Gene expression profiling: monitoring transcription and translation products using DNA microarrays and proteomics," FEBS Lett. 480:2-16 (2000).
Chabala, J.C., "Solid-phase combinatorial chemistry and novel tagging methods for identifying leads" Curr Opin Biotechnol. 6:632-639 (1995).
Cech, J., "Ribozymes and Their Medical Implications," American. Med Assoc. 260:3030-3035 (1988).
Chen, et al., "Expression of ssDNA in Mammalian Cells," BioTechniques 34:167-171 (2003).
Chen, et al., "Analogous Organic Synthesis of Small-Compound Libraries: Validation of Combinatorial Chemistry in Small-Molecule Synthesis," J. Amer. Chem. Soc. 116:2661-2662 (1994).
Cheng, J. et al., "Transcriptional maps of 10 human chromosomes at 5-nucleotide resolution," Science 308:5725:1149-1154 (2005).
Cho, et al., "An Unnatural Biopolymer," Science 261:1303-1305 (1993).
Christiensen, N.K. et al., "A Novel Class of Oligonucleotide Analogues Containing 2'-O,3'-C-Linked [3,2.0]Bicycloarabinonucleoside Monomers: Synthesis, Thermal Affinity Studies, and Molecular Modeling," J. Am. Chem. Soc., 120:5458-5463 (1998).
Cubitt, et al., "Understanding, improving and using green fluorescent proteins," Trends in Biochemical Science 20:448-455 (1995).
Curiel, D. T. et al., "Adenovirus enhancement of transferrin-polylysine-mediated gene delivery," PNAS 88:8850-8854 (1991).
Dai et al., "SIRTI Interacts With p73 and Suppresses p73-Dependent Transcriptional Activity," J Cell Physiol 210(1):161-165 (2007).
Davidson, et al., "A model system for in vivo gene transfer into the central nervous system using an adenoviral vector," Nat. Genet. 3:219-223 (1993).
Davis, et al., "Direct Gene Transfer into Skeletal Muscle in Vivo: Factors Affecting Efficiency of Transfer and Stability of Expression," Hum Gene Ther 4:151-159 (1993).
De Mesmaeker, et al., "Antisense Oligonucleotides," Acc. Chem. Res. 28:366-374 (1995).
Deng et al., "Small Interfering RNA Targeting the PINK1 Induces Apoptosis in Dopaminergic Cells SH-SY5Y", Biochemical and Biophysical Research Communications, vol. 337, No. 4, pp. 1133-1138 (2005).
Dixon, et al,. "Anthrax," New England J. Med, 341:815-826 (1999).
Dolle, "Discosiery of Enzyme inhibitors through combinatorial chemistry," Mol Divers. 2:223-236 (1997).
Eguchi, et al., "Antisense RNA," Annu. Rev. Biochem 60:631-652 (1991).
Eichler, et al., "Generation and utilization of synthetic combinatorial libraries," Mol Med Today 1:174-180 (1995).
Eichler, et al., "Peptide Peptidomimetic and organic synthetic combinatorial libraries," Med Res Rev 15:481-496 (1995).
Espeseth, et al., A genome wide analysis of ubiquitin ligases in APP processing identifies a novel regulator of BACE1 mRNA levels,' Mol. Cell Neurosci. 33: 227-235 (2006).
Faghihi, M. & Wahlestedt, C., "RNA interference is not involved in natural antisense mediated regulation of gene expression in mammals," Genome Biol (2005).
Fauchere, et al., "Peptide and nonpeptide lead discovery using robotically synthesized soluble libraries," Can J Physiol Pharmacol 75:683-689 (1997).
Felgner and Holm, "Cationic Liposome-Mediated Transfection," Bethesda Res, Lab Focus. 11:2:21 (1989).
Fields, et al., "How many genes in the human genome?" Nature Genetic 7:345-346 (1994).
Freier & Altman, "The ups and downs of nucleic acid duplex stability: structure-stability studies on chemically-modified DNA:RNA duplexes," Nucl. Acid Res., 25:22:4429-4443 (1997).

(56) References Cited

OTHER PUBLICATIONS

Fuchs, et al., "Identification of Differentially Expressed Genes by Mutually Subtracted RNA Fingerprinting," Anal. Biochem., 286:91-98 (2000).
Gebeyehu, G., et al., "Novel biotinylated nucleotide-analogs for labeling and colorimetric detection of DNA," Nucl. Acids Res. 15:4513 (1987).
Geller, A.I. et al., "An HSV-I Vector Expressing Tyrosine Hydroxylase Causes Production and Release of L-DOPA from Cultured Rat Striatil Cells," J. Neurochem 64:487-496(1995).
Geller, A.I. et al., "Long-term increases in neurotransmitter release from neuronal cells expressing a constitutively active adenylate cyclase from a herpes simplex virus type 1 vector," PNAS U.S.A. :90:7603-7607 (1993).
Geller, A.I., et al., "Infection of cultured central nervous system neurons with a defective herpes simplex virus 1 vector results in stable expression of *Escherichia coli* β-galactosidase," PNAS USA 87:1149-1153 (1990).
Giuliano, et al., "FLuorescent Protein Biosensors: Measurment of Molecular Dynamics in Living Cells," Ann. Rev. of Biophysics and Biomolecular Structure 24:405-434 (1995).
Giuliano, et al., "Light-Optical-Based Reagents for the Measurment and Manipulation of Ions, Metabolites, and Macromolecules in Living Cells," Methods in Neuroscience 27:1-16 (1995).
Giuliano, et al., "Determination of Intracellular pH of BALB/c-3T3 Cells Using the Fluorescence of Pyranine," Anal. Biochem 167:362-371 (1987).
Going & Gusterson, "Molecular Pathology and Future Developments," Eur. J. Cancer, 35:1895-1904 (1999).
Hagihara, et al., "Vinylogous Polypeptides: An Alternate Peptide Backbone," J. Amer. Chem. Soc. 114:6568-6571 (1992).
Heller, et al., "Discovery and analysis of inflammatory disease-related genes using cDNA microarrays," PNAS U.S.A. 94:2150-2155 (1997).
Herdewijn P., "Heterocyclic Modifications of Oligonucleotides and Antisense Technology," Antisense & Nucleic Acid Drug Dev., 10:297-310 (2000).
Hirschmann, et al., J. Amer. Chem. Soc., 114:9217-9218 (1992).
Hobbs-DeWitt, et al., "Diversomers: An approach to nonpeptide, nonoligomerie chemical diversity," Proc. Nat. Acad. Sci. USA 90;6909-091:3 (1993).
Houghton AN, Gold JS, Blachere NE, Immunity against cancer: lessons learned from melanoma,. Curr Opin Immuno1 13:134-140 (2001).
International Human Genome Sequencing Consortium "Finishing the euchromatic sequence of the human genome," Nature 431:7011:931-945 (2004).
Janda, K.D. "Tagged versus untagged libraries: Methods for the generation and screening of combinatorial chemical libraries," PNAS 91:10779-10785 (1994).
Janowski, et al., "Inhibiting gene expression at transcription start sites in chromosomal DNA with antigene RNAs," Nature Chemical Biology, 1(4):216-222 (2005).
Jungblut, et al., "Proteomics in human disease: Cancer, heart and infectious diseases," Electrophoresis 20:2100-2110 (1999).
Jurecic & Belmont, "Long-distance DD-PCR and cDNA microarrays," Curr. Opin. Microbiol., 3:316-321 (2000).
Kabanov, et al., "A new class of antivirals: antisense oligonucleotides combined with a hydrophobic substituent effectively inhibit influenza virus reproduction and synthesis of virus-specific proteins in MDCK cells," FEBS Lett 259:327-330 (1990).
Kaplitt, M.G., et al., "Long-term gene expression and phenotypic correction using adeno-associated virus vectors in the mammalian brain," Nat. Genet. 8:148-154 (1994).
Kapranov, P. et al., "Examples of the complex architecture of the human transcriptome revealed by RACE and high-density tiling arrays," Genome Res 15:7:987-997 (2005).
Katayama, S. et al., "Antisense Transcription in the Mammalian Transcriptone," Science 309:1564-1566 (2005).
Kawahara & Nishikura, "Extensive adenosine-to-inosine editing detected in Alu repeats of antisense RNAs reveals scarcity of sense-antisense duplex formation," FEBS Lett 580:2301-2305 (2006).
Kay, et al., "Identification of enzyme inhibitors from phage-displayed combinatorial peptide libraries," Comb Chem High Throughput Screen 4:535-543 (2001).
Kenan, et al., "Exploring molecular diversity with combinatorial shape libraries," Trends Biochem Sci 19:57-64 (1994).
Kornberg, A., DNA Replication, W.H. Freeman & Co., San Francisco, 1980 pp. 75- 77.
Larson, et al., "Rapid DNA Fingerprinting of Pathogens by Flow Cytometry," Cytometry, 2000, 41:203-208 (2000).
Larsson, et al, "High-throughput protein expression of cDNA products as a tool in functional genomics," J. Biotechnology., 80:143-157 (2000).
Lebl, et al., "One-bead-one-structure combinatorial libraries," Biopolymers 37:177-198 (1995).
LeGal Lasalle et al., "An Adenovirus Vector for Gene Transfer into Neurons and Glia in teh Brain," Science 259:988-990 (1993).
Letsinger, et al., "Cholesteryl-conjugated oligonucleotides: Synthesis, properties, and activity as inhibitors or replication of human immunodeficiency virus in cell culture," PNAS 86:6553-6550 (1989).
Li et al., "Control of APP processing and Aβ generation level by BACE1 enzymatic activity and transcription," Faseb J 20; 285-292 (2006).
Li, et al., J. Neurochem 89 1308-1312 (2004a).
Liang, et al., "Parallel Synthesis and Screening of a Solid Phase Carbohydrate Library," Science 274:1520-1522 (1996).
Luther, "Role of endogenous antisouse RNA in cardiac gene regulation," J . Mol. Med. 83:26-32 (2005).
Madden, et al., "Serial analysis of gene expression: from gene discovery to target identification," Drug Discov. Today 5:415-425 (2000).
Makalowska I: Lin CF, Makalowski W., "Overlapping genes in vertebrate genomes," Comput Biol. Chem 29:1:1-12 (2005).
Mannino and Gould-Fogerite, "Liposome Mediated Gene Transfer," BioTechniques 6:682-690 (1988).
Manoharan et al., "Lipidic Nucleic Acids," Tetrahedron Lett 36:3051-3054 (1995).
Manoharan, et al., "Chemical Modifications to Improve Uptake and Bioavailability of Antisense Oligonucleotides" Ann. N.Y. Acad. Scie 660:306-309 (1992).
Manoharan, et al., "Introduction of a Lipophilic Thioether in teh Minor Groove of Nucleic Acids for Antisense Applications," Bioorg. Med. Chem. Let 3:2765-2770 (1993).
Manoharan, et al., "Cholic Acid-Oligonucleotide Conjugates for Antisense Applications," Bioorg. Med. Chem. Let 4;1053 (1994).
Manoharan, et al., "Oligonucleotide Conjugates: Alteration of the Pharmacokinetic Properties of Antisense Agents," Nucleosides & Nucleotides 14:969-973 (1995).
Manoharan, M., "2'-Carbohydrate modifications in antisense oligonucleotide therapy: importance of conformation, configurationj and conjugation," Biochemica et Biophysica Acta 1489:117-139 (1999).
Mattick, J. S. "RNA regulation: a new genetics?" Nat. Rev. Genet. 5:4:316-323 (2004).
Maurer, R.A., "Cationic Liposome-Mediated Transfection of Primary Cultures of Rat Pituitary Cells," Bethesda Res. Lab. Focus 11:2:25 (1989).
McNeil in Methods in Cell Biology vol. 29, Taylor and Wang (eds.) p. 153-173 (1989).
Morelli et al., "The antisense *bcl-2-Ig11* transcript is an optimal target for synthetic oligonucleotides," PNAS USA 94:8150-8155 (1997).
Nielsen, et al., "Sequence-Selective Recognition of DNA by Strand Displacement with a Thymine-Substituted Polyamide," Science 254:1497-1500 (1991).
Oberhauser., et al., "Effective incorporation of 2'O-methyl-oligoribonucleotides into liposomes and enhanced cell association through modification with thiocholesterol," Nucl. Acids Res. 20:533-538 (1992).

(56) References Cited

OTHER PUBLICATIONS

Petit et al., "Wild-type PINK1 Prevents Basal and induced Neuronal Apoptosis, a Protective Effect Abrogated by Parkinson Disease-Related Mutations", Journ. Biol, Chem., vol. 280, No. 40, pp. 34025-334032 (2005).
Prasanth, et al., "Regulating Gene Expression through RNA Nuclear Retention," Cell 123, 249-263 (2005).
Prashar & Weissman, "READS: A Method for Display of 3'-End Fragments of Restriction Enzyme-Digested cDNAs for Analysis or Differential Gene Expression," Methods Enzymol., 303:258-272 (1999).
Quantin, et al., "Adenovirus as an expression vector in muscle cells in vivo," PNAS 89:2581-2584 (1992).
Rosenfeld, et al., "In Vivo Transfer of the Human Cystic Fibrosis Transmembrane Conductance Regulator Gene to the Airway Epithelium," Cell, 68:143-155 (1992).
Rosok and Sioud, "Systematic identification of sense-antisense transcripts in mammalian cells," Nature Biotech. 22(1):104-108 (2004).
Saison-Behmoaras, et al., "Short modified antisense oligonucleotides directed against Ha-ras point mutation induce selective cleavage of the mRNA and inhibit T24 cells proliferation," EMBO J. 10:1111-1118 (1991).
Sanghvi, Y.S., in Crooke, S.T. and Lebleu, B., eds, Antisense Research and Applications, CRC Press, Boca Raton, 1993, p. 276-278.
Scheele et al., "The Human PINK1 Locus is Regulated and Vivo by a Non-Coding Natural Antisense RNA During Modulation of Mitochondrial Function", BMC Genomics, vol. 8, No. 1, p. 74 (2007).
Schena, et al., "Parallel human genome analysis: Microarray-based expression monitoring of 1000 genes," PNAS 93:10614-10619(1996).
Shea, et al., "Synthesis, hybridization properties and antiviral activity of lipid-oligodeoxynucleotide conjugates," Nucl. Acids Res 18:3777-3783 (1990).
Shimomura, et al., "Semi-synthetic aequorin," J. of Biochemistry (Tokyo) 251:405-410 (1988).
Singer, et al., "Targeting BACE1 with siRNAs ameliorates Alzheimer disease neuropathology in a transgenic model," Nat Neurosci 8:1343-1349 (2005).
Southwick, et al., "Cyanine Dye Labeling Reagents-Carboxymethylindocyanine Succinimidyl Esters," Cytometry 11:418-430 (1990).
Stratford-Perricadet, et al., "Widespread Long-term Gene Transfer to Mouse Skeletal Muscles and Heart," J. Clin. Invest., 90:626-630 (1992).
Sullenger, et al., "Overexpression of TAR sequences Renders Cells Resistant to Human Immunodeficiency Virus Replication," Cell63:601-608 (1990).
Sun et al., "Downregulation of Sirt 1 by antisense oligonucleotides induces apoptosis and enhances radiations sensitization in A549 lung cancer cells," Lung Cancer 58(1):21-29 (2007).
Sutcliffe, et al., "TOGA: An automated parsing technology for analyzing expression of nearly all genes," PNAS, 97:1976-1981 (2000).
Sutton, et al., "TIGR Assembler: A New Tool for Assembling Large Shotgun Sequencing Projects," Genome Science & Tech., 1:9-19 (1995).
Svinarchuk, et al,, "Inhibition of HIV proliferation in MT-4 cells by antisense oligonucleotide conjugated to lipophilic groups," Biochimie 75:49-54 (1993).
Tamagno, et al., "The various aggregation states of β-amyloid I-42 mediate different effects on oxidative stress, neurodegeneration, and BACE-1 expression," Free Radic Biol Med 41:202-212 (2006).
Thakker, D.R., et al., "siRNA-mediated knockdown of the serotonin transporter in the adult mouse brain," Mol Psychiatry 10:782-789 (2005).
Thakker, et al., "Neurochemical and behavioral consequences of widespread gene knockdown in the adult mouse brain by using nonviral RNA interference," PNAS 101:17270-17275 (2004).
Thomas et al., "Intracellular pH Measurements in Ehrlich Ascites Tumor Cells Utilizing Spectroscopic Probes Generated in Situ," Biochemistry 18:2210-2218 (1979).
Thompson, et al., "Synthesis and Applications of Small Molecule Libraries" Chem Rev 96:555-600 (1996).
To, Ky, "Identification of Differential Gene Expressionm by High Throughput Analysis," Comb. Chem. High Throughput Screen 3:235-241 (2000).
Tong, et al., "Oxidative stress potentiates BACE1 gene expression," Neural Transm 112, 455-469 (2005).
Toulme, J.J., "New candidates for true antisense," Nature Biotechnology 19:17-18 (2001).
Tsien in Methods in Cell Biology vol. 30 Taylor and Wang (eds) p. 127-156 (1989).
Ulhman, E., "Recent advances in the medical chemistry of antisense oligonucleotide," Current Opinions in Drug, Discovery & Development 3:203-213 (2000).
Van Den Eynde BJ, "T cell defined tumor antigens," Curr Opin Immunol 9:684-693 (1997).
Van Der Bruggen, et al., "Tumor-specific shared antigenic peptides recognized by human T cells," Immunol Rev188:51-64 (2002).
Vanhee-Brossolet and Vaquero, "Do natural antisense transcripts make sense in eukaryotes?" Gene 211:1-9 (1998).
Vaughn, et al., "Human Antibodies with Sub-nanomolar Affinities Isolated from a Large Non-immunized Phage Display Library," Nature Biotechnology, 14:3:309-314 (1996).
Velculescu, et al., "Serial Analysis of Gene Expression," Science 270:484-487 (1995).
Wahlestedt, "Natural antisense and noncoding RNA transcripts as potential drug targets," Drug Discovery Today 11 (11/12):503-508 (2006).
Wahlestedt, C., "Antisense oligonucleotide strategies in neuropharmacology," Trends Pharmacol Sci 15:2:42-46 (1994).
Walsh, et al, The role of cell-derived oligomers Aβ in Alzheimer's disease and avenues for therapeutic intervention, Biochem Soc Trans 33: 1087-1090 (2005).
Wang, B.B. et al., "Identification of a nuclear-specific cyclophilin which interacts with the proteinase inhibitor eglin c," Biochem J. 314 (Pt 1) 313-319 (1996).
Wiesenhofer et al., "Glial cell line-derived neurotrophic factor (GDNP) is a proliferation factor for rat C6 glioma cells: evidence from antisense experiments," Antisense & Nucleic Acid Drug Development: 10(5):311-321 (2000).
Xue, et al., "Hypoxia and reoxygenation increased BACE1 mRNA and protein levels in human neuroblastoma SH-SY5Y cells," Neurosci Lett 405,231-235 (2006).
Yamada et al., "Endothelial Nitric-Oxide Synthase Antisense (NOS3AS) Gene Encodes an Autophagy-Related Protein (APG9-like2) Highly Expressed in Trophoblast" (2005).
Yang, et al "Cellular and Humoral Immune Responses to Viral Antigens Create Barriers to Lung-Directed Gene Therapy with Recombinant Adenoviruses," J. Virol 69:2004-2015 (1995).
EP Application No. 06850393.7 Examination Report dated Oct. 18, 2011.
International Search Report and Written Opinion for PCT Application No. PCT/US2010/033078 mailed Jun. 29, 2011.
PCT/US2010/026119 Search Report and Written Opinion mailed Feb. 7, 2011.
PCT/US2010/024079 Search Report and Written Opinion mailed Jan. 31. 2011.
PCT/US2010/027394 Search Report and Written Opinion mailed Nov. 5, 2010.
PCT/US96/10287 (WO97/000271) The Regents of the University of California 1.3.97.
International Search Report corresponding to PCT/US2011/020321 dated Oct. 19, 2011.

* cited by examiner

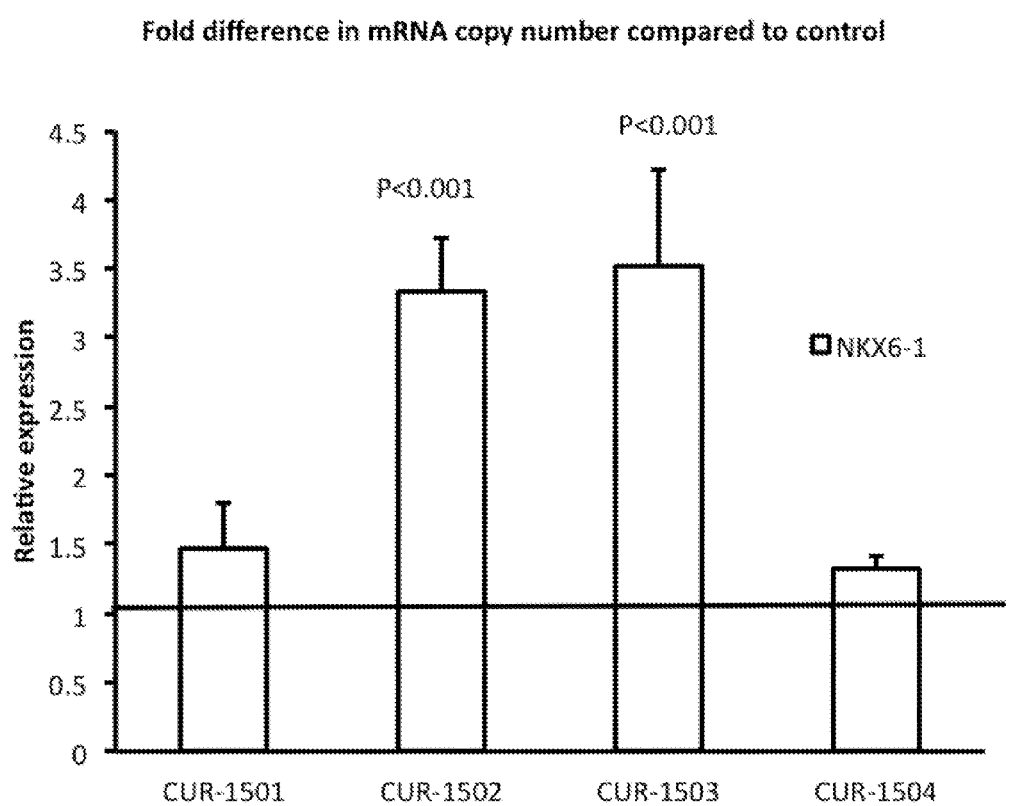

TREATMENT OF PANCREATIC DEVELOPMENTAL GENE RELATED DISEASES BY INHIBITION OF NATURAL ANTISENSE TRANSCRIPT TO A PANCREATIC DEVELOPMENTAL GENE

The present application claims the priority of U.S. provisional patent application 61/292,508 filed Jan. 6, 2010; U.S. provisional patent application No. 61/294,129 filed Jan. 12, 2010; U.S. provisional patent application No. 61/297,847 filed Jan. 25, 2010. U.S. provisional patent application No. 61/297,863 filed Jan. 25, 2010; U.S. provisional patent application No. 61/323,027 filed Apr. 12, 2010 and which are incorporated herein by reference in their entireties.

FIELD OF THE INVENTION

Embodiments of the invention comprise oligonucleotides modulating expression and/or function of a Pancreatic Developmental gene and associated molecules.

BACKGROUND

DNA-RNA and RNA-RNA hybridization are important to many aspects of nucleic acid function including DNA replication, transcription, and translation. Hybridization is also central to a variety of technologies that either detect a particular nucleic acid or alter its expression. Antisense nucleotides, for example, disrupt gene expression by hybridizing to target RNA, thereby interfering with RNA splicing, transcription, translation, and replication. Antisense DNA has the added feature that DNA-RNA hybrids serve as a substrate for digestion by ribonuclease H, an activity that is present in most cell types. Antisense molecules can be delivered into cells, as is the case for oligodeoxynucleotides (ODNs), or they can be expressed from endogenous genes as RNA molecules. The FDA recently approved an antisense drug, VITRAVENE™ (for treatment of cytomegalovirus retinitis), reflecting that antisense has therapeutic utility.

SUMMARY

In one embodiment, the invention provides methods for inhibiting the action of a natural antisense transcript by using antisense oligonucleotide(s) targeted to any region of the natural antisense transcript resulting in up-regulation of the corresponding sense gene. It is also contemplated herein that inhibition of the natural antisense transcript can be achieved by siRNA, ribozymes and small molecules, which are considered to be within the scope of the present invention.

One embodiment provides a method of modulating function and/or expression of a Pancreatic Developmental gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of a polynucleotide comprising 5 to 30 consecutive nucleotides within nucleotides 1 to 1235 of SEQ ID SEQ ID NO: 6, 1 to 17,964 of SEQ ID NO: 7, 1 to 1 to 50,003 of SEQ ID SEQ ID NO: 8, 1 to 486 of SEQ ID NO: 9, 1 to 494 of SEQ ID NO: 10, 1 to 1992 of SEQ ID NO: 11, or 1 to 1767 of SEQ ID NO: 12 thereby modulating function and/or expression of the Pancreatic Developmental gene polynucleotide in patient cells or tissues in vivo or in vitro.

In another embodiment, an oligonucleotide targets a natural antisense sequence of a Pancreatic Developmental gene polynucleotide, for example, nucleotides set forth in SEQ ID NO: 6 to 12, and any variants, alleles, homologs, mutants, derivatives, fragments and complementary sequences thereto. Examples of antisense oligonucleotides are set forth as SEQ ID NOS: 13 to 45.

Another embodiment provides a method of modulating function and/or expression of a Pancreatic Developmental gene polynucleotide in patient cells or tissues in vivo or in vitro comprising contacting said cells or tissues with an antisense oligonucleotide 5 to 30 nucleotides in length wherein said oligonucleotide has at least 50% sequence identity to a reverse complement of the an antisense of the Pancreatic Developmental gene polynucleotide; thereby modulating function and/or expression of the Pancreatic Developmental gene polynucleotide in patient cells or tissues in vivo or in vitro.

Another embodiment provides a method of modulating function and/or expression of a Pancreatic Developmental gene polynucleotide in patient cells or tissues in vivo or in vitro comprising contacting said cells or tissues with an antisense oligonucleotide 5 to 30 nucleotides in length wherein said oligonucleotide has at least 50% sequence identity to an antisense oligonucleotide to a Pancreatic Developmental gene antisense polynucleotide: thereby modulating function and/or expression of the Pancreatic Developmental gene polynucleotide in patient cells or tissues in vivo or in vitro.

In one embodiment, a composition comprises one or more antisense oligonucleotides which bind to sense and/or antisense Pancreatic Developmental gene polynucleotides.

In another embodiment, the oligonucleotides comprise one or more modified or substituted nucleotides.

In another embodiment, the oligonucleotides comprise one or more modified bonds.

In yet another embodiment, the modified nucleotides comprise modified bases comprising phosphorothioate, methylphosphonate, peptide nucleic acids, 2'-O-methyl, fluoro- or carbon, methylene or other locked nucleic acid (LNA) molecules. Preferably, the modified nucleotides are locked nucleic acid molecules, including α-L-LNA.

In another embodiment, the oligonucleotides are administered to a patient subcutaneously, intramuscularly, intravenously or intraperitoneally.

In another embodiment, the oligonucleotides are administered in a pharmaceutical composition. A treatment regimen comprises administering the antisense compounds at least once to patient; however, this treatment can be modified to include multiple doses over a period of time. The treatment can be combined with one or more other types of therapies.

In another embodiment, the oligonucleotides are encapsulated in a liposome or attached to a carrier molecule (e.g. cholesterol, TAT peptide).

Other aspects are described infra.

BRIEF DESCRIPTION OF THE DRAWINGS

FIG. 5 is a graph of real time PCR results showing the fold change+standard deviation in NKX6-1 mRNA after treatment of MCF-7 cells with phosphorothioate oligonucleotides introduced using Lipofectamine 2000, as compared to control. Bars denoted as CUR-1501 to CUR-1504 correspond to samples treated with SEQ ID NOS: 42 to 45 respectively.

SEQUENCE LISTING DESCRIPTION

Figure 1:
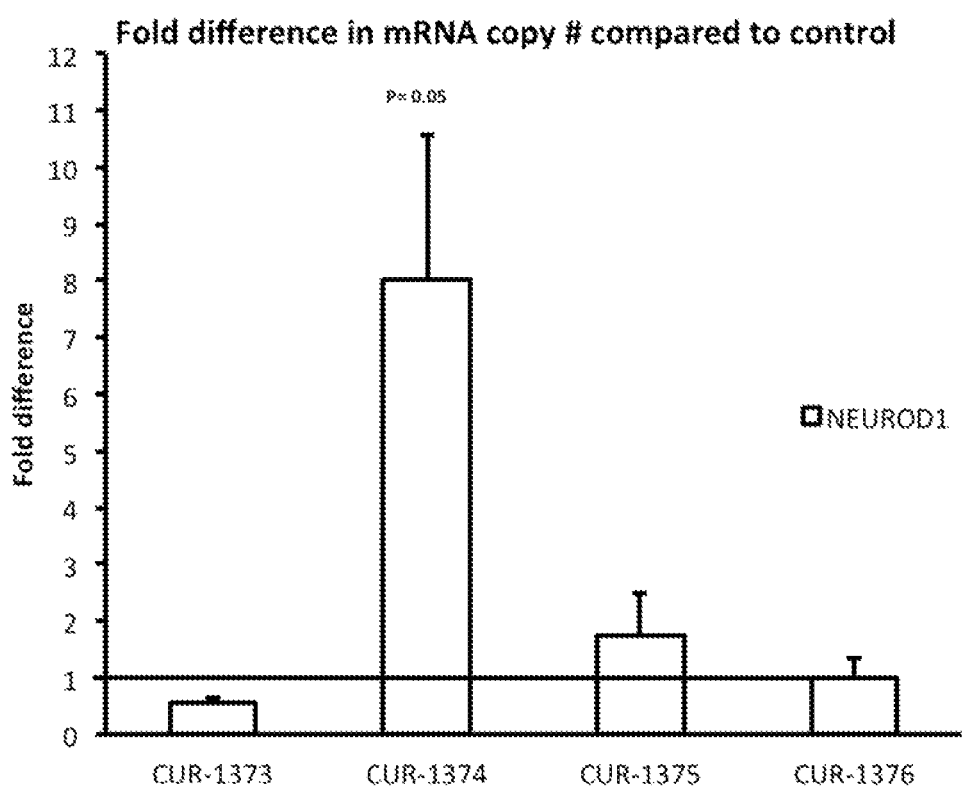
FIG. 1 is a graph of real time PCR results showing the fold change+standard deviation in NEUROD1 mRNA after treatment of HepG2 cells with phosphorothioate oligonucleotides introduced using Lipofectamine 2000, as compared to control. Real time PCR results show that the levels of the NEUROD1 mRNA in HepG2 cells are significantly increased 48 h after treatment with one of the oligos designed to NEUROD1 antisense Steedo.aApr07. Bars denoted as CUR-1373, CUR-1374, CUR-1375 and CUR-1376 correspond to samples treated with SEQ ID NOS: 13 to 16 respectively.

SEQ ID NO: 1: Homo sapiens neurogenic differentiation 1 (NEUROD1), mRNA (NCBI Accession No.: NM_002500). SEQ ID NO: 2: Homo sapiens hepatocyte nuclear factor 4, alpha (HNF4A), transcript variant 2, mRNA (NCBI Accession No.: NM_000457). SEQ ID NO: 3: Homo sapiens v-maf musculoaponeurotic fibrosarcoma oncogene homolog A (avian) (MAFA), mRNA (NCBI Accession No.: NM_201589). SEQ ID NO: 4: Homo sapiens pancreatic and duodenal homeobox 1 (PDX1), mRNA (NCBI Accession No.: NM_000209).
SEQ ID NO: 5: Homo sapiens NK6 homeobox 1 (NKX6-1), mRNA, (NCBI Accession No.: NM_006168).
SEQ ID NOs: 6 to 12: SEQ ID NO: 6: Natural NEUROD1 antisense sequence (Steedo.aApr07); SEQ ID NO: 7: Natural HNF4A antisense sequence (AF143870); SEQ ID NO: 8: Natural HNF4A antisense sequence (BC071794); SEQ ID NO: 9: Natural HNF4A antisense sequence (BX099913); SEQ ID NO: 10: Natural MAFA antisense sequence (BM127748); SEQ ID NO: 11: Natural PDX1 antisense sequence (Hs.416201) and SEQ ID NO: 12: Natural NKX6-1 antisense sequence (torsnaby.aApr07-unspliced)
SEQ ID NOs: 13 to 45: Antisense oligonucleotides. * indicates phosphothioate bond.

DETAILED DESCRIPTION

Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. The present invention is not limited by the ordering of acts or events, as some acts may occur in different orders and/or concurrently with other acts or events. Furthermore, not all illustrated acts or events are required to implement a methodology in accordance with the present invention.

All genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes disclosed herein, which in some embodiments relate to mammalian nucleic acid and amino acid sequences are intended to encompass homologous and/or orthologous genes and gene products from other animals including, but not limited to other mammals, fish, amphibians, reptiles, and birds. In embodiments, the genes or nucleic acid sequences are human.

DEFINITIONS

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "mRNA" means the presently known mRNA transcript(s) of a targeted gene, and any further transcripts which may be elucidated.

By "antisense oligonucleotides" or "antisense compound" is meant an RNA or DNA molecule that binds to another RNA or DNA (target RNA, DNA). For example, if it is an RNA oligonucleotide it binds to another RNA target by means of RNA-RNA interactions and alters the activity of the target RNA. An antisense oligonucleotide can upregulate or downregulate expression and/or function of a particular polynucleotide. The definition is meant to include any foreign RNA or DNA molecule which is useful from a therapeutic, diagnostic, or other viewpoint. Such molecules include, for example, antisense RNA or DNA molecules, interference RNA (RNAi), micro RNA, decoy RNA molecules, siRNA, enzymatic RNA, therapeutic editing RNA, and agonist and antagonist RNA, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

In the context of this invention, the term "oligonucleotide" refers to an oligomer or polymer of ribonucleic acid (RNA) or deoxyribonucleic acid (DNA) or mimetics thereof. The term "oligonucleotide", also includes linear or circular oligomers of natural and/or modified monomers or linkages, including deoxyribonucleosides, ribonucleosides, substituted and alpha-anomeric forms thereof, peptide nucleic acids (PNA), locked nucleic acids (LNA), phosphorothioate, methylphosphonate, and the like. Oligonucleotides are capable of specifically binding to a target polynucleotide by way of a regular pattern of monomer-to-monomer interactions, such as Watson-Crick type of base pairing, Hoögsteen or reverse Hoögsteen types of base pairing, or the like.

The oligonucleotide may be "chimeric", that is, composed of different regions. In the context of this invention "chimeric" compounds are oligonucleotides, which contain two or more chemical regions, for example, DNA region(s), RNA region(s), PNA region(s) etc. Each chemical region is made up of at least one monomer unit, i.e., a nucleotide in the case of an oligonucleotides compound. These oligonucleotides typically comprise at least one region wherein the oligonucleotide is modified in order to exhibit one or more desired properties. The desired properties of the oligonucleotide include, but are not limited, for example, to increased resistance to nuclease degradation, increased cellular uptake, and/or increased binding affinity for the target nucleic acid. Different regions of the oligonucleotide may therefore have different properties. The chimeric oligonucleotides of the present invention can be formed as mixed structures of two or more oligonucleotides, modified oligonucleotides, oligonucleosides and/or oligonucleotide analogs as described above.

The oligonucleotide can be composed of regions that can be linked in "register" that is, when the monomers are linked consecutively, as in native DNA, or linked via spacers. The spacers are intended to constitute a covalent "bridge" between the regions and have in cases a length not exceeding about 100 carbon atoms. The spacers may carry different functionalities, for example, having positive or negative charge, carry special nucleic acid binding properties (intercalators, groove binders, toxins, fluorophors etc.), being lipophilic, inducing special secondary structures like, for example, alanine containing peptides that induce alpha-helices.

As used herein "Pancreatic Developmental genes" and "Pancreatic Developmental gene" are inclusive of all family members, mutants, alleles, fragments, species, coding and noncoding sequences, sense and antisense polynucleotide strands, etc.

As used herein, the words 'Neurogenic differentiation 1', 'Neurogenic differentiation factor 1', NEUROD1, BETA2, BHF-1, bHLHa3, NeuroD, NEUROD, NeuroD1, are considered the same in the literature and are used interchangeably in the present application.

As used herein, the words Hepatocyte nuclear factor 4, alpha; Hepatocyte nuclear factor 4, alpha.; HNF4.alpha.; HNF4A, HNF-4alpha, MODY, MODY1, NR2A1, NR2A21, TCF, TCF14, Transcription factor-14. APF, LFB1 and HP1 are considered the same in the literature and are used interchangeably in the present application.

As used herein, the words 'v-maf musculoaponeurotic fibrosarcoma oncogene homolog A', MAFA, hMafA, v-maf, mafA, Pancreatic beta-cell-specific transcriptional activator, RIPE3b1, Transcription factor MafA. Transcription factor RIPE3b1, V-maf musculoaponeurotic fibrosarcoma oncogene homolog A (avian), are considered the same in the literature and are used interchangeably in the present application.

As used herein, the words 'Pancreatic and duodenal homeobox 1', PDX1, PDX-1. Glucose-sensitive factor, GSF, IDX-1. Insulin promoter factor 1, Insulin upstream factor 1, IPF1, IPF-1, Islet/duodenum homeobox-1, IUF1, IUF-1, MODY4, Pancreas/duodenum homeobox protein 1, Somatostatin-transactivating factor 1, STF-1 are considered the same in the literature and are used interchangeably in the present application.

As used herein, the words NK6 homeobox 1, NKX6-1, Homeobox protein NK-6 homolog A, Homeobox protein Nkx-6.1, Nkx6.1, NKX6.1 and NKX6A are considered the same in the literature and are used interchangeably in the present application.

As used herein, the term "oligonucleotide specific for" or "oligonucleotide which targets" refers to an oligonucleotide having a sequence (i) capable of forming a stable complex with a portion of the targeted gene, or (ii) capable of forming a stable duplex with a portion of a mRNA transcript of the targeted gene. Stability of the complexes and duplexes can be determined by theoretical calculations and/or in vitro assays. Exemplary assays for determining stability of hybridization complexes and duplexes are described in the Examples below.

As used herein, the term "target nucleic acid" encompasses DNA, RNA (comprising premRNA and mRNA) transcribed from such DNA, and also cDNA derived from such RNA, coding, noncoding sequences, sense or antisense polynucleotides. The specific hybridization of an oligomeric compound with its target nucleic acid interferes with the normal function of the nucleic acid. This modulation of function of a target nucleic acid by compounds, which specifically hybridize to it, is generally referred to as "antisense". The functions of DNA to be interfered include, for example, replication and transcription. The functions of RNA to be interfered, include all vital functions such as, for example, translocation of the RNA to the site of protein translation, translation of protein from the RNA, splicing of the RNA to yield one or more mRNA species, and catalytic activity which may be engaged in or facilitated by the RNA. The overall effect of such interference with target nucleic acid function is modulation of the expression of an encoded product or oligonucleotides.

RNA interference "RNAi" is mediated by double stranded RNA (dsRNA) molecules that have sequence-specific homology to their "target" nucleic acid sequences. In certain embodiments of the present invention, the mediators are 5-25 nucleotide "small interfering" RNA duplexes (siRNAs). The siRNAs are derived from the processing of dsRNA by an RNase enzyme known as Dicer. siRNA duplex products are recruited into a multi-protein siRNA complex termed RISC (RNA Induced Silencing Complex). Without wishing to be bound by any particular theory, a RISC is then believed to be guided to a target nucleic acid (suitably mRNA), where the siRNA duplex interacts in a sequence-specific way to mediate cleavage in a catalytic fashion. Small interfering RNAs that can be used in accordance with the present invention can be synthesized and used according to procedures that are well known in the art and that will be familiar to the ordinarily skilled artisan. Small interfering RNAs for use in the methods of the present invention suitably comprise between about 1 to about 50 nucleotides (nt). In examples of non limiting embodiments, siRNAs can comprise about 5 to about 40 nt, about 5 to about 30 nt, about 10 to about 30 nt, about 15 to about 25 nt, or about 20-25 nucleotides.

Selection of appropriate oligonucleotides is facilitated by using computer programs that automatically align nucleic acid sequences and indicate regions of identity or homology. Such programs are used to compare nucleic acid sequences obtained, for example, by searching databases such as GenBank or by sequencing PCR products. Comparison of nucleic acid sequences from a range of species allows the selection of nucleic acid sequences that display an appropriate degree of identity between species. In the case of genes that have not been sequenced, Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

By "enzymatic RNA" is meant an RNA molecule with enzymatic activity. Enzymatic nucleic acids (ribozymes) act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through base pairing, and once bound to the correct site, acts enzymatically to cut the target RNA.

By "decoy RNA" is meant an RNA molecule that mimics the natural binding domain for a ligand. The decoy RNA therefore competes with natural binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA. This is meant to be a specific example. Those in the art will recognize that this is but one example, and other embodiments can be readily generated using techniques generally known in the art.

As used herein, the term "monomers" typically indicates monomers linked by phosphodiester bonds or analogs thereof to form oligonucleotides ranging in size from a few monomeric units, e.g., from about 3-4, to about several hundreds of monomeric units. Analogs of phosphodiester linkages include: phosphorothioate, phosphorodithioate, methylphosphomates, phosphoroselenoate, phosphoramidate, and the like, as more fully described below.

The term "nucleotide" covers naturally occurring nucleotides as well as nonnaturally occurring nucleotides. It should be clear to the person skilled in the art that various nucleotides which previously have been considered "non-naturally occurring" have subsequently been found in nature. Thus, "nucleotides" includes not only the known purine and pyrimidine heterocycles-containing molecules, but also heterocyclic analogues and tautomers thereof. Illustrative examples of other types of nucleotides are molecules containing adenine, guanine, thymine, cytosine, uracil, purine, xanthine, diaminopurine, 8-oxo-N6-methyladenine, 7-deazaxanthine, 7-deazaguanine, N4,N4-ethanocytosin, N6,N6-ethano-2,6-diaminopurine, 5-methylcytosine, 5-(C3-C6)-alkynylcytosine, 5-fluorouracil, 5-bromouracil, pseudoisocytosine, 2-hydroxy-5-methyl-4-triazolopyridin, isocytosine, isoguanin, inosine and the "non-naturally occurring" nucleotides described in U.S. Pat. No. 5,432,272. The term "nucleotide" is intended to cover every and all of these examples as well as analogues and tautomers thereof. Especially interesting nucleotides are those containing adenine, guanine, thymine, cytosine, and uracil, which are considered as the naturally occurring nucleotides in relation to therapeutic and diagnostic application in humans. Nucleotides include the natural 2'-deoxy and 2'-hydroxyl sugars, e.g., as described in Komberg and Baker, DNA Replication, 2nd Ed. (Freeman, San Francisco, 1992) as well as their analogs.

"Analogs" in reference to nucleotides includes synthetic nucleotides having modified base moieties and/or modified sugar moieties. Such analogs include synthetic nucleotides designed to enhance binding properties, e.g., duplex or triplex stability, specificity, or the like.

As used herein, "hybridization" means the pairing of substantially complementary strands of oligomeric compounds. One mechanism of pairing involves hydrogen bonding, which may be Watson-Crick. Hoögsteen or reversed Hoögsteen hydrogen bonding, between complementary nucleoside or nucleotide bases (nucleotides) of the strands of oligomeric compounds. For example, adenine and thymine are complementary nucleotides which pair through the formation of hydrogen bonds. Hybridization can occur under varying circumstances.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated. In general, stringent hybridization conditions comprise low concentrations (<0.15 M) of salts with inorganic cations such as Na++ or K++ (i.e., low ionic strength), temperature higher than 20° C.-25° C. below the Tm of the oligomeric compound:target sequence complex, and the presence of denaturants such as formamide, dimethylformamide, dimethyl sulfoxide, or the detergent sodium dodecyl sulfate (SDS). For example, the hybridization rate decreases 1.1% for each 1% formamide. An example of a high stringency hybridization condition is 0.1× sodium chloride-sodium citrate buffer (SSC)/0.1% (w/v) SDS at 60° C. for 30 minutes.

"Complementary," as used herein, refers to the capacity for precise pairing between two nucleotides on one or two oligomeric strands. For example, if a nucleobase at a certain position of an antisense compound is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleotides which can hydrogen bond with each other. Thus, "specifically hybridizable" and "complementary" are terms which are used to indicate a sufficient degree of precise pairing or complementarity over a sufficient number of nucleotides such that stable and specific binding occurs between the oligomeric compound and a target nucleic acid.

It is understood in the art that the sequence of an oligomeric compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). The oligomeric compounds of the present invention comprise at least about 70%, or at least about 75%, or at least about 80%, or at least about 85%, or at least about 90%, or at least about 95%, or at least about 99% sequence complementarity to a target region within the target nucleic acid sequence to which they are targeted. For example, an antisense compound in which 18 of 20 nucleotides of the antisense compound are complementary to a target region, and would therefore specifically hybridize, would represent 90 percent complementarity. In this example, the remaining noncomplementary nucleotides may be clustered or interspersed with complementary nucleotides and need not be contiguous to each other or to complementary nucleotides. As such, an antisense compound which is 18 nucleotides in length having 4 (four) noncomplementary nucleotides which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art. Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (*Adv. Appl. Math.*, (1981) 2, 482-489).

As used herein, the term "Thermal Melting Point (Tm)" refers to the temperature, under defined ionic strength, pH, and nucleic acid concentration, at which 50% of the oligonucleotides complementary to the target sequence hybridize to the target sequence at equilibrium. Typically, stringent conditions will be those in which the salt concentration is at least about 0.01 to 1.0 M Na ion concentration (or other salts) at pH 7.0 to 8.3 and the temperature is at least about 30° C. for short oligonucleotides (e.g., 10 to 50 nucleotide). Stringent conditions may also be achieved with the addition of destabilizing agents such as formamide.

As used herein, "modulation" means either an increase (stimulation) or a decrease (inhibition) in the expression of a gene.

The term "variant," when used in the context of a polynucleotide sequence, may encompass a polynucleotide sequence related to a wild type gene. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. Of particular utility in the invention are variants of wild type gene products. Variants may result from at least one mutation in the nucleic acid sequence and may result in altered mRNAs or in polypeptides whose structure or function may or may not be altered. Any given natural or recombinant gene may have none, one, or many allelic forms. Common mutational changes that give rise to variants are generally ascribed to natural deletions, additions, or substitutions of nucleotides. Each of these types of changes may occur alone, or in combination with the others, one or more times in a given sequence.

The resulting polypeptides generally will have significant amino acid identity relative to each other. A polymorphic variant is a variation in the polynucleotide sequence of a particular gene between individuals of a given species. Polymorphic variants also may encompass "single nucleotide polymorphisms" (SNPs,) or single base mutations in which the polynucleotide sequence varies by one base. The presence of SNPs may be indicative of, for example, a certain population with a propensity for a disease state, that is susceptibility versus resistance.

Derivative polynucleotides include nucleic acids subjected to chemical modification, for example, replacement of hydrogen by an alkyl, acyl, or amino group. Derivatives, e.g., derivative oligonucleotides, may comprise non-naturally-occurring portions, such as altered sugar moieties or inter-sugar linkages. Exemplary among these are phosphorothioate and other sulfur containing species which are known in the art. Derivative nucleic acids may also contain labels, including radionucleotides, enzymes, fluorescent agents, chemiluminescent agents, chromogenic agents, substrates, cofactors, inhibitors, magnetic particles, and the like.

A "derivative" polypeptide or peptide is one that is modified, for example, by glycosylation, pegylation, phosphorylation, sulfation, reduction/alkylation, acylation, chemical coupling, or mild formalin treatment. A derivative may also be modified to contain a detectable label, either directly or indirectly, including, but not limited to, a radioisotope, fluorescent, and enzyme label.

As used herein, the term "animal" or "patient" is meant to include, for example, humans, sheep, elks, deer, mule deer, minks, mammals, monkeys, horses, cattle, pigs, goats, dogs, cats, rats, mice, birds, chicken, reptiles, fish, insects and arachnids.

"Mammal" covers warm blooded mammals that are typically under medical care (e.g., humans and domesticated animals). Examples include feline, canine, equine, bovine, and human, as well as just human.

"Treating" or "treatment" covers the treatment of a disease-state in a mammal, and includes: (a) preventing the disease-state from occurring in a mammal, in particular, when such mammal is predisposed to the disease-state but has not yet been diagnosed as having it; (b) inhibiting the disease-state, e.g., arresting it development; and/or (c) relieving the disease-state, e.g., causing regression of the disease state until a desired endpoint is reached. Treating also includes the amelioration of a symptom of a disease (e.g., lessen the pain or discomfort), wherein such amelioration may or may not be directly affecting the disease (e.g., cause, transmission, expression, etc.).

As used herein, "cancer" refers to all types of cancer or neoplasm or malignant tumors found in mammals, including, but not limited to: leukemias, lymphomas, melanomas, carcinomas and sarcomas. The cancer manifests itself as a "tumor" or tissue comprising malignant cells of the cancer.

Examples of rumors include sarcomas and carcinomas such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma. Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pincaloma, hemangioblastoma, acoustic neuroma, oligodendroglioma, meningioma, melanoma, neuroblastoma, and retinoblastoma. Additional cancers which can be treated by the disclosed composition according to the invention include but not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Neurological disease or disorder" refers to any disease or disorder of the nervous system and/or visual system. "Neurological disease or disorder" include disease or disorders that involve the central nervous system (brain, brainstem and cerebellum), the peripheral nervous system (including cranial nerves), and the autonomic nervous system (parts of which are located in both central and peripheral nervous system). Examples of neurological disorders include but are not limited to, headache, stupor and coma, dementia, seizure, sleep disorders, trauma, infections, neoplasms, neuroophthalmology, movement disorders, demyelinating diseases, spinal cord disorders, and disorders of peripheral nerves, muscle and neuromuscular junctions. Addiction and mental illness, include, but are not limited to, bipolar disorder and schizophrenia, are also included in the definition of neurological disorder. The following is a list of several neurological disorders, symptoms, signs and syndromes that can be treated using compositions and methods according to the present invention: acquired epileptiform aphasia; acute disseminated encephalomyelitis; adrenoleukodystrophy; age-related macular degeneration; agenesis of the corpus callosum; agnosia; Aicardi syndrome; Alexander disease; Alpers' disease; alternating hemiplegia; Vascular dementia; amyotrophic lateral sclerosis; anencephaly; Angelman syndrome; angiomatosis; anoxia; aphasia; apraxia; arachnoid cysts; arachnoiditis; Anronl-Chiari malformation; arteriovenous malformation; Asperger syndrome; ataxia telegiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome; causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy; chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease; cytomegalovirus infection; dancing eyes-dancing feet syndrome; Dandy-Walker syndrome; Dawson disease; Dc Morsier's syndrome; Dejerine-Klumke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; fronto-temporal dementia and other "tauopathies"; Gaucher's disease; Gerstmanns syndrome; giant cell arteritis; giant cell inclusion disease; globoid cell leukodystrophy; Guillain-Barre syndrome; HTLV-1-associated myelopathy; Hallervorden-Spatz disease; head injury; headache; hemifacial spasm; hereditary spastic paraplegia; heredopathia atactic a polyneuritiformis; herpes zoster oticus; herpes zoster; Hirayama syndrome; HIV associated dementia and neuropathy (also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; infantile refsum disease; infantile spasms; inflammatory myopathy; intracranial cyst; intracranial hypertension; Joubert syndrome; Keams-Sayre syndrome; Kennedy disease Kinsboume syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gustaut syndrome; Lesch-Nyhan syndrome; leukodystrophy; Lewy body dementia; Lisseneephaly; locked-in syndrome; Lou Gehrig's disease (i.e., motor neuron disease or amyotrophic lateral sclerosis); lumbar disc disease; Lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neuron disease; Moyamoya disease; mucopolysaccharidoses; milti-infarct dementia; multifocal motor neuropathy; multiple sclerosis and other demyelinating disorders; multiple system atrophy with postural hypotension; p muscular dystrophy; myasthenia gravis; myelinoelastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae oflupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia;

Neurodegenerative disease or disorder (Parkinson's disease, Huntington's disease, Alzheimer's disease, amyotrophic lateral sclerosis (ALS), dementia, multiple sclerosis and other diseases and disorders associated with neuronal cell death); paramyotonia congenital; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocalleukoencephalopathy; progressive sclerosing poliodystrophy; progressive supranuclear palsy; pseudotumor cerebri; Ramsay-Hunt syndrome (types I and II); Rasmussen's encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; Tic Douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau disease; Wallenberg's syndrome; Werdnig-Hoffman disease; West syndrome; whiplash; Williams syndrome; Wildon's disease; and Zellweger syndrome.

An "Inflammation" refers to systemic inflammatory conditions and conditions associated locally with migration and attraction of monocytes, leukocytes and/or neutrophils. Examples of inflammation include, but are not limited to, Inflammation resulting from infection with pathogenic organisms (including gram-positive bacteria, gram-negative bacteria, viruses, fungi, and parasites such as protozoa and helminths), transplant rejection (including rejection of solid organs such as kidney, liver, heart, lung or cornea, as well as rejection of bone marrow transplants including graft-versus-host disease (GVHD)), or from localized chronic or acute autoimmune or allergic reactions. Autoimmune diseases include acute glomerulonephritis; rheumatoid or reactive arthritis; chronic glomerulonephritis; inflammatory bowel diseases such as Crohn's disease, ulcerative colitis and necrotizing enterocolitis; granulocyte transfusion associated syndromes; inflammatory dermatoses such as contact dermatitis, atopic dermatitis, psoriasis; systemic lupus erythematosus (SLE), autoimmune thyroiditis, multiple sclerosis, and some forms of diabetes, or any other autoimmune state where attack by the subject's own immune system results in pathologic tissue destruction. Allergic reactions include allergic asthma, chronic bronchitis, acute and delayed hypersensitivity. Systemic inflammatory disease states include inflammation associated with trauma, burns, reperfusion following ischemic events (e.g. thrombotic events in heart, brain, intestines or peripheral vasculature, including myocardial infarction and stroke), sepsis, ARDS or multiple organ dysfunction syndrome. Inflammatory cell recruitment also occurs in atherosclerotic plaques. Inflammation includes, but is not limited to, Non-Hodgkin's lymphoma, Wegener's granulomatosis, Hashimoto's thyroiditis, hepatocellular carcinoma, thymus atrophy, chronic pancreatitis, rheumatoid arthritis, reactive lymphoid hyperplasia, osteoarthritis, ulcerative colitis, papillary carcinoma, Crohn's disease, ulcerative colitis, acute cholecystitis, chronic cholecystitis, cirrhosis, chronic sialadenitis, peritonitis, acute pancreatitis, chronic pancreatitis, chronic Gastritis, adenomyosis, endometriosis, acute cervicitis, chronic cervicitis, lymphoid hyperplasia, multiple sclerosis, hypertrophy secondary to idiopathic thrombocytopenic purpura, primary IgA nephropathy, systemic lupus erythematosus, psoriasis, pulmonary emphysema, chronic pyelonephritis, and chronic cystitis.

A cardiovascular disease or disorder includes those disorders that can either cause ischemia or are caused by reperfusion of the heart. Examples include, but are not limited to, atherosclerosis, coronary artery disease, granulomatous myocarditis, chronic myocarditis (non-granulomatous), primary hypertrophic cardiomyopathy, peripheral artery disease (PAD), stroke, angina pectoris, myocardial infarction, cardiovascular tissue damage caused by cardiac arrest, cardiovascular tissue damage caused by cardiac bypass, cardiogenic shock, and related conditions that would be known by those of ordinary skill in the art or which involve dysfunction of or tissue damage to the heart or vasculature, especially, but not limited to, tissue damage related to a Pancreatic Developmental gene activation. CVS diseases include, but are not limited to, atherosclerosis, granulomatous myocarditis, myocardial infarction, myocardial fibrosis secondary to valvular heart disease, myocardial fibrosis without infarction, primary hypertrophic cardiomyopathy, and chronic myocarditis (non-granulomatous).

A 'Metabolic disease or disorder" refers to a wide range of diseases and disorders of the endocrine system including, for example, insulin resistance, diabetes, obesity, impaired glucose tolerance, high blood cholesterol, hyperglycemia, hyperinsulinemia, dyslipidemia and hyperlipidemia.

Polynucleotide and Oligonucleotide Compositions and Molecules

Targets

In one embodiment, the targets comprise nucleic acid sequences of a Pancreatic Developmental gene, including without limitation sense and/or antisense noncoding and/or coding sequences associated with a Pancreatic Developmental gene.

In one embodiment, the targets comprise nucleic acid sequences of NEUROD1, including without limitation sense and/or antisense noncoding and/or coding sequences associated with NEUROD1 gene.

In one embodiment, the targets comprise nucleic acid sequences of HNF4A, including without limitation sense and/or antisense noncoding and/or coding sequences associated with HNF4A gene.

In one embodiment, the targets comprise nucleic acid sequences of MAFA, including without limitation sense and/or antisense noncoding and/or coding sequences associated with MAFA gene.

In one embodiment, the targets comprise nucleic acid sequences of PDX1, including without limitation sense and/or antisense noncoding and/or coding sequences associated with PDX1 gene.

In one embodiment, the targets comprise nucleic acid sequences of NKX6, including without limitation sense and/or antisense noncoding and/or coding sequences associated with NKX6 gene.

BETA2/NeuroD1 is a tissue-specific basic helix-loop-helix transcription factor with ability to up-regulate insulin gene expression. NeuroD1/BETA2 is a key regulator of pancreatic islet morphogenesis and insulin hormone gene transcription in islet beta cells. It was cloned as a gene required for neuronal differentiation, named NeuroD; we now refer to the gene asBETA2/NeuroD1. Like many bHLH family members that play important roles in regulating various developmental systems, BETA2/NeuroD1 is essential for development of the pancreas and brain.

HNF4A encodes a transcription factor with an important role in hepatocyte and pancreatic transcriptional regulation. An orphan nuclear receptor and hepatic activator, hepatic nuclear factor-4 (HNF-4), is a central regulator of transcriptional networks in the liver and pancreatic β-cells. The two promoters, P1 and P2, are located 45.5 kb apart on chromosome 20q. While HNF4A transcripts in the liver are primarily of P1 origin, the P2 promoter drives expression in the pancreas, where it regulates genes involved in insulin secretion and glucose homeostasis.

MAFA is the β-cell-specific nuclear factor bound to a conserved cis-regulatory element called RIPE3b1 in the insulin gene enhancer region and functions as an important transactivator for the insulin gene. MAFA is a basic-leucine zipper (bLZ) transcription factor that controls β-cell-specific expression of the insulin gene through a cis-regulatory element called RIPE3b1 and functions as potent transactivator of insulin gene. MAFA cooperates synergistically with NEUROD1 and PDX1. Phosphorylation by GSK3 increases its transcriptional activity and is required for its oncogenic activity.

Pancreatic-duodenal homeobox 1 (PDX1) is a transcription factor of homeobox genes family important in differentiation and development of the pancreas, duodenum and antrum. Pancreatic duodenal homeobox 1 (PDX-1) is a transcription factor with a critical role in pancreatic development. PDX-1 regulates pancreatic cell proliferation and differentiation, and increased expression of this transcription factor has been described in huma Pancreatic adenocarcinoma and cell lines. Pdx1 is also necessary for β-cell maturation: developing β-cells co-express Pdx1, Nkx6-1, and insulin, a process that results in the silencing of MafB and the expression of MafA, a necessary switch in maturation of β-cells. Pdx1 appears to also play a role in the fating of endocrine cells, encoding for insulin and somatostatin, two pancreatic endocrine products, while repressing glucagon. Thus, Pdx1 expression apparently favors the production of insulin+ β-cells and somatostatin+Δ-cells rather than glucagon+ α-cells.

Nkx6.1 is recognized as the most beta-cell specific transcription factor in the pancreas. Nkx6 homeodomain transcription factors have important developmental roles in the CNS and the pancreas. Nkx6.1 is essential for proper motoneuron and oligodendrocyte development and the development and maintenance of insulin-producing pancreatic beta cells.

Nkx-6.1 is expressed in ventral neural progenitor cells and subsequently in the median half of the lateral motor neuron column (LMCm) and in mesenchymal tissues surrounding Shh-expressing cells; ventral spinal meninges, esophageal mesenchyme, and dorsal tracheal mesenchyme. Nkx6.1 is required for ventral regional patterning and neuronal fate determination in the vertebrate CNS. Nkx6.1 controls motor neuron and ventral interneuron fates. Nkx6.1 controls migration and axon pathfinding of cranial branchio-motoneurons and it is required for the early specification of somatic motoneuron progenitors in the spinal cord. Early specification of branchio-motoncurons (hindbrain) is independent of Nkx6.1 function, but it is required for their subsequent development. Nkx6.1 is required for the development of postmitotic motoneurons, and the control of branchio-motoneuron migration. The status of Nkx6.1 expression in certain motor neuron pools regulates muscle nerve formation, and the pattern of innervation of individual muscles.

Table 1 Shows a List of Some Pancreatic Developmental Genes

It should be appreciated that in the Table 1 below, an indicated gene means the gene and all currently known variants thereof, including the different mRNA transcripts that the gene and its variants can give rise to, any further gene variants which may be elucidated, and antisense sequences. The list also includes the non-coding RNA molecules or the portions of polynucleotides. In general, however, such variants will have significant sequence identity to a sequence of any polynucleotide in Table 1 below, e.g., a variant will have at least about 70 percent sequence identity to a sequence of the Table 1 below, typically at least about 75, 80, 85, 90, 95, 97, 98 or 99 percent sequence identity to a sequence of the below Table 1. Sequence identity of variant can be determined by any number of standard techniques such as BLAST program (ncbi.nclm.nih.gov/blast/).

TABLE I

| Gene Symbol | Accession Number | Function |
| --- | --- | --- |
| VEGFA | NM_001025366 | Induces angiogenesis, vasculogenesis and endothelial cell growth, promotes cell migration, and inhibits apoptosis. |
| TCF7L2 | NM_001146274 | Blood glucose homeostasis |
| SST | NM_001048 | Inhibits the release of numerous secondary hormones by binding 10 high-affinity G-protein-coupled somatostatin receptors |
| SOX9 | NM_000346 | Maintenance of pancreatic progenitor cells |
| SOX17 | NM_022454 | Pancreas development |
| SLC2A2 | NM_000340 | Mediates facilitated bidirectional glucose transport |
| RBPJL | NM_014276 | Pancreas development - formation of ascinar structures |
| RBPJ | NM_005349 | Pancreas development - formation of ascinar structures |
| PYY | NM_004160 | Inhibits pancreatic secretion and mobility in the gut |
| PTF1A | NM_178161 | Determines whether cells allocated to the pancreatic buds continue towards pancreatic organogenesis or revert back to duodenal fates. The protein is thought to be involved in the maintenance of exocrine pancreas-specific gene expression including elastase 1 and amylase. |
| PPY | NM_002722 | Acts as a regulator of pancreatic and gastrointestinal functions and may be important in the regulation of food intake. |

TABLE I-continued

| Gene Symbol | Accession Number | Function |
|---|---|---|
| POU3F4 | NM_000307 | Expressed in the pancreatic anlaga of the mouse foregut at e10 in the alpha cells and transactivates glucagon gene expression |
| PDX1 | NM_000209 | Transcriptional activator of several genes, including insulin, somatostatin, glucokinase, islet amyloid polypeptide, and glucose transporter type 2. The encoded nuclear protein is involved in the early development of the pancreas and plays a major role in glucose-dependent regulation of insulin gene expression. |
| PBX1 | NM_002585 | PBX1 regulates the activity of PDX1 in pancreatic development. Regulates proglucagon expression by serving as a co-factor for Cdx-2 |
| PAX 6 | NM_000280 | Glucose homeostasis. regulates beta and alpha cell differentiation |
| PAX4 | NM_006193 | Involved in pancreatic islet development and differentiation of insulin-producing beta cells |
| ONECUT 1 | NM_004498 | Transcriptional regulator of pancreatic duct development. Serves as a coactivator protein to enhance FoxA2 transcription |
| Nodal | NM_018055 | pancreas development |
| NKX6-1 | NM_006168 | Required for the development of beta cells and is a potent bifunctional transcription regulator that binds to AT-rich sequences within the promoter region of target genes |
| NKX2-2 | NM_002509 | Regulates NKX6.1, regulates differentiation of beta cells |
| NEUROG 3 | NM_020999 | Critical for the development of alpha and beta cells |
| NEUROD 1 | NM_002500 | Regulates expression of the insulin gene |
| MYT1 | NM_004535 | Initiates endocrine differentiation in pancreatic islet cells, positively regulates NGF3 |
| MYC | NM_002467 | Induces cell proliferation |
| MNX1 | NM_001165255 | Transcriptional activator protein expressed early in pancreas development |
| MIXL1 | NM_031944 | Transcription factor that regulates cell fate during development |
| MAFB | NM_005461 | Activator of glucagon gene expression in alpha and beta cells |
| MAFA | NM_201589 | Regulates pancreatic beta cell-specific expression of the insulin gene |
| KRT19 | NM_002276 | Pancreas development - duct formation |
| ISL2 | NM_145805 | Pancreas development -bud formation |
| ISL1 | NM_002202 | The encoded protein binds to the enhancer region of the insulin gene, among others, and may play an important role in regulating insulin gene expression. The encoded protein is central to the development of pancreatic cell lineages and may also be required for motor neuron generation. |
| INSM1 | NM_002196 | Pancreatic beta cell development |
| Ins2 | NM_000207, NM_001185097, NM_001185098 | Insulin - stimulates glucose uptake |
| Ins1 | NM_000207, NM_001185097, NM_001185098 | Insulin - stimulates glucose uptake |
| INHBB | NM_002193 | Inhibins and activins inhibit and activate, respectively, the secretion of follitropin by the pituitary gland. Inhibins/activins are involved in regulating a number of diverse functions such as hypothalamic and pituitary hormone secretion, gonadal hormone secretion, germ cell development and maturation, erythroid differentiation, insulin secretion, nerve cell survival, embryonic axial development or bone growth, depending on their subunit composition. Inhibins appear to oppose the functions of activins |
| HNF4A | NM_000457.3 | Regulates expression of HNF1a |
| HNF1B | NM_000458.2 | Regulates expression of HNF4a |
| HHEX | NM_002729.4 | Recognizes the DNA sequence 5'-ATTAA-3'. Transcriptional repressor. May play a role in hematopoietic differentiation. Establishes anterior identity at two levels: acts early to enhance canonical WNT-signaling by repressing expression of TLE4, and acts later to inhibit NODAL-signaling by directly targeting NODAL |
| HES1 | NM_005524 | Represses the expression of Ngn preventing neuronal differentiation in cells adjacent to developing neuroblasts. |
| GHRL | NM_001134941 | Ghrelin is an endogenous ligand for the growth hormone secretagogue receptor and is involved in regulating growth hormone release. |
| Gdfl1 | NM_005811 | promotes beta-cell differentiation, modulates NGN3 |
| GCG | NM_002054 | Glucagon, is a pancreatic hormone that counteracts the glucose-lowering action of insulin by stimulating glycogenolysis and gluconeogenesis |
| GATA6 | NM_005257 | interacts with Nkx2.2 |
| Gata4 | NM_002052 | Transcriptional activator. Binds to the consensus sequence 5'-AGATAG-3'. Acts as a transcriptional activator of ANF in cooperation with NKX2-5 |
| FST | NM_006350 | Binds directly to activin and functions as an activin antagonist. Specific inhibitor of the biosynthesis and secretion of pituitary follicle stimulating hormone (FSH) |
| FOXA2 | NM_021784 | regulation of Pdx1 |
| FOXA1 | NM_004496 | regulation of Pdx1 |
| FGF2 | NM_002006 | Induction of pancreatic islet clusters |
| FGF10 | NM_004465 | Maintains the pancreatic progenitor cell state |
| CPA1 | NM_001868 | Carboxypeptidase A1 is a monomeric pancreatic exopeptidase. It is involved in zymogen inhibition |
| ARX | NM_139058 | The ARX gene provides instructions for producing a protein that regulates the activity of other genes. On the basis of this action, the ARX protein is called a transcription factor. The ARX gene is part of a larger family of homeobox genes, which act during early embryonic development to control the formation of many |

TABLE I-continued

| Gene Symbol | Accession Number | Function |
|---|---|---|
| | | body structures. Specifically, the ARX protein is believed to be involved in the development of the pancreas, gastrointestinal tract, testes, and brain. |
| AMY1 | NM_001008221 | This gene encodes an amylase isoenzyme produced by the salivary gland. Alternative splicing results in multiple transcript variants encoding the same protein. |
| ACVR2B | NM_001106 | On ligand binding, forms a receptor complex consisting of two type II and two type I transmembrane serine/threonine kinases. Type II receptors phosphorylate and activate type I receptors which autophosphorylate, then bind and activate SMAD transcriptional regulators. Receptor for activin A, activin B and inhibin A |
| ACVR2A | NM_001616 | On ligand binding, forms a receptor complex consisting of two type II and two type I transmembrane serine/threonine kinases. Type II receptors phosphorylate and activate type I receptors which autophosphorylate, then bind and activate SMAD transcriptional regulators. Receptor for activin A, activin B and inhibin A |

In some embodiments, antisense oligonucleotides are used to prevent or treat diseases or disorders associated with Pancreatic Developmental gene family members. Exemplary Pancreatic Developmental gene mediated diseases and disorders which can be treated with cell/tissues regenerated from stem cells obtained using the antisense compounds comprise: a disease or disorder associated with abnormal function and/or expression of a Pancreatic Developmental gene, a disease or disorder associated with abnormal function and/or expression of any of the genes listed in Table 1, a cardiovascular disease or disorder (e.g., congestive heart failure, myocardial infarction, an Ischemic disease, an atrial or ventricular arrhythmia, a hypertensive vascular disease, a peripheral vascular disease, and atherosclerosis etc.), inflammation, a gastrointestinal disease or disorder (e.g., a disorder of the esophagus, achalasia, vigoruos achalasia, dysphagia, cricopharyngcal incoordination, pre-esophageal dysphagia, diffuse esophageal spasm, globus sensation, Barrett's metaplasia, gastroesophageal reflux etc.), a disease or disorder of the stomach and/or duodenum (e.g., functional dyspepsia, inflammation of the gastric mucosa, gastritis, stress gastritis, chronic erosive gastritis, atrophy of gastric glands, metaplasia of gastric tissues, gastric ulcers, duodenal ulcers, a neoplasm of the stomach), a disease or disorder of the pancreas (e.g., acute or chronic pancreatitis, insufficiency of the exocrinic or endocrinic tissues of the pancreas like steatorrhea, diabetes etc.), a neoplasm of the exocrine or endocrine pancreas (e.g., multiple endocrine neoplasia syndrome, ductal adenocarcinoma, cystadenocarcinoma, an islet cell tumor, insulinoma, gastrinoma, carcinoid minors, glucagonoma, Zollinger-Ellison syndrome, Vipoma syndrome, malabsorption syndrome etc.), a disease or disorder of the bowel (e.g., chronic inflammatory disease of the bowel, Crohn's disease, ileus, diarrhea and constipation, colonic inertia, megacolon, malabsorption syndrome, ulcerative colitis, a functional bowel disorder, irritable bowel syndrome etc.), a neoplasm of the bowel (e.g., familial polyposis, adenocarcinoma, primary malignant lymphoma, carcinoid tumors, Kaposi's sarcoma, polyps, cancer of the colon and rectum.); a hepatic disease or disorder (e.g., bilirubin metabolism disorder, jaundice, syndroms of Gilbert's, Crigler-Najjar, Dubin-Johnson and Rotor; intrahepatic cholestasis, hepatomegaly, portal hypertension, ascites, Budd-Chiari syndrome, portal-systemic encephalopathy, fatty liver, steatosis, Reye's syndrome, a liver disease due to alcohol, alcoholic hepatitis or cirrhosis, fibrosis, cirrhosis etc.), fibrosis and/or cirrhosis of the liver due to inborn errors of metabolism or exogenous substances, a storage disease or disorder, syndrome of Gaucher's, Zellweger's, Wilson's-disease, acute or chronic hepatitis, viral hepatitis and its variants; an inflammatory condition of the liver due to virus, bacteria, fungi, protozoa, helminth; a drug induced disease or disorder of the liver, a chronic liver disease like primary sclerosing cholangitis, alphai-antitrypsin-deficiency, primary biliary cirrhosis, a postoperative liver disorder like postoperative intrahepatic cholestasis, a hepatic granuloma, a vascular liver disease or disorder associated with systemic disease, a benign or malignant neoplasm of the liver, a disturbance of liver metabolism in the new-born or prematurely born a musculoskeletal Disease (e.g., osteoporosis, postmenopausal osteoporosis, senile osteoporosis, secondary osteoporosis, idiopathic juvenile osteoporosis, Paget's disease of the bone, osteochondroma, osteocartilaginous exostose, etc.), a tumor of the bone (e.g., benign chondromas, chondroblastomas, chondromyxoid fibromas, osteoid osteomas, a giant cell tumor of the bone, multiple myeloma, osteosarcoma (osteogenic sarcoma), fibrosarcoma, malignant fibrous histiocytoma, chondrosarcomas, Ewing's tumor (Ewing's sarcoma), malignant lymphoma of bone (reticulum cell sarcoma, metastatic tumors of the bone), osteoarthritis, and gout and Pseudogout; a disorder of joint and connective tissue (e.g., rheumatoid arthritis, psoriatic arthritis, discoid lupus erythematosus, systemic lupus erythematosus, scleroderma (systemic sclerosis), Sjogren's syndrome, connective tissue disease, polymyositis and dermatomyositis, relapsing polychondritis, vasculitis, polyarteritis nodosa, polymyalgia rheumatica, temporal arteritis, Wegener's granulomatosis, Reiter's syndrome, Behcet's syndrome, ankylosing spondylitis, or Charcot's joints (neuropathic joint disease) etc.); a bone and joint infection (e.g., osteomyelitis, and infectious arthritis); a disease or disorder of muscles, bursas, and/or tendons (e.g., spasmodic torticollis, fibromyalgia syndromes (myofascial pain syndromes, fibromyositis), bursitis, tendinitis and tenosynovitis), foot problem (e.g., ankle sprain, foot fractures, heel spurs, Sever's disease, posterior achilles tendon bursitis, anterior achilles tendon bursitis, posterior tibial neuralgia, pain in the ball of the foot (caused by damage to the nerves between the toes or to the joints between the toes and foot), onychomycosis, or nail discoloration), cancer, an inflammatory disease or disorder such as: hypersensitivity reactions of type I-IV (e.g., a hypersensitivity disease of the lung including asthma, atopic diseases, allergic rhinitis or conjunctivitis, angioedema of the lids, hereditary angioedema, antireceptor hypersensitivity reactions and autoimmune diseases, Hashimoto's thyroiditis, systemic lupus erythematosus, Goodpasture's syndrome, pemphigus, myasthenia gravis, Grave's and Raynaud's disease, type B insulin-resistant diabetes, rheumatoid arthritis, psoriasis, Crohn's disease, scleroderma, mixed connective tissue disease, polymyositis, sarcoidosis, glomerulonephritis, acute or chronic host versus graft reactions); a pulmonary disease or disorder such as: Chronic obstructive pulmonary disease (COPD); a urinary system disorder such as: malign disorders of the organs constituting the genitourinary system of female and male, a renal disease or disorder like acute or chronic renal failure, immunologically mediated renal diseases like renal transplant rejection, lupus nephritis, immune complex renal diseases, glomerulopathies, nephritis, toxic nephropathy, an obstructive uropathy like benign prostatic hyperplasia (BPH), neurogenic bladder syndrome, urinary incontinence like urge-, stress-, or overflow incontinence, pelvic pain, and erectile dysfunction, a disease or a disorder associated with defective endocrine pancreatic development (e.g., type 2 diabetes mellitus); a disease or a disorder associated with defective neurogenesis; a neurodegenerative disease or disorder (e.g. Alzheimer's disease, Parkinson's disease, amyotrophic lateral sclerosis etc.); a disease or a disorder associated with defective development of the vestibular and/or auditory system, a disease or a disorder associated with photoreceptor cell degeneration (e.g., loss of vision, age-related macular degeneration etc.), obesity, a disease or a disorder associated with defective functioning of liver (e.g., liver failure), pulverulent cataract, cerulean cataract, non-syndromic congenital cataract, congenital cataract-microcornea syndrome, a pancreatic disease or a disorder (e.g., diabetes, MODY syndrome. Partial pancreas agenesis, chronic hyperglycemia, pancreatic beta cell failure, glucose toxicity, Glucose Intolerance, Metabolic syndrome X etc.), Crohn's disease, myocardial infarction, intercranial, intercranial arterosclerosis, cerebral infarction, herpesviral infection, a disease or disorder associated with impaired lipid metabolism, a disease or disorder associated with insulin production, a disease or disorder associated with serotonin production (e.g., depression and obesity), a neurological disease or disorder (including disorders associated with neural defects (e.g., defects in motor neurons, serotonin-producing neurons, dopamine neurons, and developmental defects in the forebrain, midbrain, hindbrain, and spinal cord) etc.), a disease of the reproductive System and a metabolic disease or disorder such as diabetes (e.g., type 2 diabetes; non-insulin dependent diabetes mellitus).

In another embodiment, the antisense oligonucleotides modulate the expression, in vivo amounts and/or function of a Pancreatic Developmental gene in patients suffering from or at risk of developing diseases or disorders associated with Pancreatic Developmental genes.

In one embodiment, the oligonucleotides are specific for polynucleotides of a Pancreatic Developmental gene, which includes, without limitation noncoding regions. The Pancreatic Developmental gene targets comprise variants of a Pancreatic Developmental gene: mutants of a Pancreatic Developmental gene, including SNPs; noncoding sequences of a Pancreatic Developmental gene; alleles, fragments and the like. Preferably the oligonucleotide is an antisense RNA molecule.

In accordance with embodiments of the invention, the target nucleic acid molecule is not limited to Pancreatic Developmental gene polynucleotides alone but extends to any of the isoforms, receptors, homologs, non-coding regions and the like of a Pancreatic Developmental gene.

In another embodiment, an oligonucleotide targets a natural antisense sequence (natural antisense to the coding and non-coding regions) of a Pancreatic Developmental gene targets, including, without limitation, variants, alleles, homologs, mutants, derivatives, fragments and complementary sequences thereto. Preferably the oligonucleotide is an antisense RNA or DNA molecule.

In another embodiment, the oligomeric compounds of the present invention also include variants in which a different base is present at one or more of the nucleotide positions in the compound. For example, if the first nucleotide is an adenine, variants may be produced which contain thymidine, guanosine, cytidine or other natural or unnatural nucleotides at this position. This may be done at any of the positions of the antisense compound.

In some embodiments, homology, sequence identity or complementarity, between the antisense compound and target is from about 50% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

An antisense compound is specifically hybridizable when binding of the compound to the target nucleic acid interferes with the normal function of the target nucleic acid to cause a loss of activity, and there is a sufficient degree of complementarity to avoid non-specific binding of die antisense compound to non-target nucleic acid sequences under conditions in which specific binding is desired. Such conditions include, i.e., physiological conditions in the case of in vivo assays or therapeutic treatment, and conditions in which assays are performed in the case of in vitro assays.

An antisense compound, whether DNA, RNA, chimeric, substituted etc, is specifically hybridizable when binding of the compound to the target DNA or RNA molecule interferes with the normal function of the target DNA or RNA to cause a loss of utility, and there is a sufficient degree of complementarily to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

In another embodiment, targeting of a Pancreatic Developmental gene including without limitation, antisense sequences which are identified and expanded, using for example, PCR, hybridization etc., one or more of the sequences set forth as SEQ ID NO: 6 to 12, and the like, modulate the expression or function of a Pancreatic Developmental gene. In one embodiment, expression or function is up-regulated as compared to a control. In another embodiment, expression or function is down-regulated as compared to a control.

In another embodiment, oligonucleotides comprise nucleic acid sequences set forth as SEQ ID NOS: 13 to 45 including antisense sequences which are identified and expanded, using for example, PCR, hybridization etc. These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

The specificity and sensitivity of antisense is also harnessed by those of skill in the an for therapeutic uses. Antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In embodiments of the present invention oligomeric antisense compounds, particularly oligonucleotides, bind to target nucleic acid molecules and modulate the expression and/or function of molecules encoded by a target gene. The functions of DNA to be interfered comprise, for example, replication and transcription. The functions of RNA to be interfered comprise all vital functions such as, for example, translocation of the RNA to the site of protein translation, translation of protein from the RNA, splicing of the RNA to yield one or more mRNA species, and catalytic activity which may be engaged in or facilitated by the RNA. The functions may be up-regulated or inhibited depending on the functions desired.

The antisense compounds, include, antisense oligomeric compounds, antisense oligonucleotides, external guide sequence (EGS) oligonucleotides, alternate splicers, primers, probes, and other oligomeric compounds that hybridize to at least a portion of the target nucleic acid. As such, these compounds may be introduced in the form of single-stranded, double-stranded, partially single-stranded, or circular oligomeric compounds.

Targeting an antisense compound to a particular nucleic acid molecule, in the context of this invention, can be a multistep process. The process usually begins with the identification of a target nucleic acid whose function is to be modulated. This target nucleic acid may be, for example, a cellular gene (or mRNA transcribed from the gene) whose expression is associated with a particular disorder or disease state, or a nucleic acid molecule from an infectious agent. In the present invention, the target nucleic acid encodes a Pancreatic Developmental gene.

The targeting process usually also includes determination of at least one target region, segment, or site within the target nucleic acid for the antisense interaction to occur such that the desired effect, e.g., modulation of expression, will result. Within the context of the present invention, the term "region" is defined as a portion of the target nucleic acid having at least one identifiable structure, function, or characteristic. Within regions of target nucleic acids are segments. "Segments" are defined as smaller or sub-portions of regions within a target nucleic acid. "Sites," as used in the present invention, are defined as positions within a target nucleic acid.

In one embodiment, the antisense oligonucleotides bind to the natural antisense sequences of a Pancreatic Developmental gene and modulate the expression and/or function of a Pancreatic Developmental gene (SEQ ID NO: 1 to 5). Examples of antisense sequences include SEQ ID NOS: 6 to 45.

In another embodiment, the antisense oligonucleotides bind to one or more segments of a Pancreatic Developmental gene polynucleotide and modulate the expression and/or function of a Pancreatic Developmental gene. The segments comprise at least five consecutive nucleotides of a Pancreatic Developmental gene sense or antisense polynucleotides.

In another embodiment, the antisense oligonucleotides are specific for natural antisense sequences of a Pancreatic Developmental gene wherein binding of the oligonucleotides to the natural antisense sequences of a Pancreatic Developmental gene modulate expression and/or function of a Pancreatic Developmental gene.

In another embodiment, oligonucleotide compounds comprise sequences set forth as SEQ ID NOS: 13 to 45, antisense sequences which are identified and expanded, using for example, PCR, hybridization etc These oligonucleotides can comprise one or more modified nucleotides, shorter or longer fragments, modified bonds and the like. Examples of modified bonds or internucleotide linkages comprise phosphorothioate, phosphorodithioate or the like. In another embodiment, the nucleotides comprise a phosphorus derivative. The phosphorus derivative (or modified phosphate group) which may be attached to the sugar or sugar analog moiety in the modified oligonucleotides of the present invention may be a monophosphate, diphosphate, triphosphate, alkylphosphate, alkanephosphate, phosphorothioate and the like. The preparation of the above-noted phosphate analogs, and their incorporation into nucleotides, modified nucleotides and oligonucleotides, per se, is also known and need not be described here.

Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes has a translation initiation codon having the RNA sequence 5'-GUG, 5'-UUG or 5'-CUG; and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA transcribed from a gene encoding a Pancreatic Developmental gene, regardless of the sequence(s) of such codons. A translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. Consequently, the "start codon region" (or "translation initiation codon region") and the "stop codon region" (or "translation termination codon region") are all regions that may be targeted effectively with the antisense compounds of the present invention.

The open reading frame (ORF) or "coding region," which is known in the art to refer to the region between the translation initiation codon and the translation termination codon, is also a region which may be targeted effectively. Within the context of the present invention, a targeted region is the intragenic region encompassing the translation initiation or termination codon of the open reading frame (ORF) of a gene.

Another target region includes the 5' untranslated region (5'UTR), known in the art to refer to the portion of an mRNA in the 5' direction from the translation initiation codon, and thus including nucleotides between the 5' cap site and the translation initiation codon of an mRNA (or corresponding nucleotides on the gene). Still another target region includes the 3' untranslated region (3'UTR), known in the art to refer to the portion of an mRNA in the 3' direction from the translation termination codon, and thus including nucleotides between the translation termination codon and 3' end of an mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. Another target region for this invention is the 5' cap region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. In one embodiment, targeting splice sites, i.e., intron-exon junctions or exon-intron junctions, is particularly useful in situations where aberrant splicing is implicated in disease, or where an overproduction of a particular splice product is implicated in disease. An aberrant fusion junction due to rearrangement or deletion is another embodiment of a target site. mRNA transcripts produced via the process of splicing of two (or more) mRNAs from different gene sources are known as "fusion transcripts". Introns can be effectively targeted using antisense compounds targeted to, for example, DNA or pre-mRNA.

In another embodiment, the antisense oligonucleotides bind to coding and/or non-coding regions of a target polynucleotide and modulate the expression and/or function of the target molecule.

In another embodiment, the antisense oligonucleotides bind to natural antisense polynucleotides and modulate the expression and/or function of the target molecule.

In another embodiment, the antisense oligonucleotides bind to sense polynucleotides and modulate the expression and/or function of the target molecule.

Alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and exonic sequence.

Upon excision of one or more exon or intron regions, or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

Variants can be produced through the use of alternative signals to start or stop transcription. Pre-mRNAs and mRNAs can possess more than one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites. Within the context of the invention, the types of variants described herein are also embodiments of target nucleic acids.

The locations on the target nucleic acid to which the antisense compounds hybridize are defined as at least a 5-nucleotide long portion of a target region to which an active antisense compound is targeted.

While the specific sequences of certain exemplary target segments are set forth herein, one of skill in the art will recognize that these serve to illustrate and describe particular embodiments within the scope of the present invention. Additional target segments are readily identifiable by one having ordinary skill in the an in view of this disclosure.

Target segments 5-100 nucleotides in length comprising a stretch of at least five (5) consecutive nucleotides selected from within the illustrative target segments are considered to be suitable for targeting as well.

Target segments can include DNA or RNA sequences that comprise at least the 5 consecutive nucleotides from the 5'-terminus of one of the illustrative target segments (the remaining nucleotides being a consecutive stretch of the same DNA or RNA beginning immediately upstream of the 5'-terminus of the target segment and continuing until the DNA or RNA contains about 5 to about 100 nucleotides). Similarly target segments are represented by DNA or RNA sequences that comprise at least the 5 consecutive nucleotides from the 3'-terminus of one of the illustrative target segments (the remaining nucleotides being a consecutive stretch of the same DNA or RNA beginning immediately downstream of the 3'-terminus of the target segment and continuing until the DNA or RNA contains about 5 to about 100 nucleotides). One having skill in the art armed with the target segments illustrated herein will be able, without undue experimentation, to identify further target segments.

Once one or more target regions, segments or sites have been identified, antisense compounds are chosen which are sufficiently complementary to the target, i.e., hybridize sufficiently well and with sufficient specificity, to give the desired effect.

In embodiments of the invention the oligonucleotides bind to an antisense strand of a particular target. The oligonucleotides are at least 5 nucleotides in length and can be synthesized so each oligonucleotide targets overlapping sequences such that oligonucleotides are synthesized to cover the entire length of the target polynucleotide. The targets also include coding as well as non coding regions.

In one embodiment, specific nucleic acids are targeted by antisense oligonucleotides. Targeting an antisense compound to a particular nucleic acid, is a multistep process. The process usually begins with the identification of a nucleic acid sequence whose function is to be modulated. This may be, for example, a cellular gene (or mRNA transcribed from the gene) whose expression is associated with a particular disorder or disease state, or a non coding polynucleotide such as for example, non coding RNA (ncRNA).

RNAs can be classified into (1) messenger RNAs (mRNAs), which are translated into proteins, and (2) non-protein-coding RNAs (ncRNAs). ncRNAs comprise microRNAs, antisense transcripts and other Transcriptional Units (TU) containing a high density of stop codons and lacking any extensive "Open Reading Frame". Many ncRNAs appear to start from initiation sites in 3' untranslated regions (3'UTRs) of protein-coding loci. ncRNAs are often rare and at least half of the ncRNAs that have been sequenced by the FANTOM consortium seem not to be polydenylate. Most researchers have for obvious reasons focused on polyadenylated mRNAs that are processed and exported to the cytoplasm. Recently, it was shown that the set of non-polyadenylated nuclear RNAs may be very large, and that many such transcripts arise from intergenic regions. The mechanism by which ncRNAs may regulate gene expression is by base pairing with target transcripts. The RNAs that function by base pairing can be grouped into (1) cis encoded RNAs that are encoded at the same genetic location, but on the opposite strand to the RNAs they act upon and therefore display perfect complementarity to their target, and (2) trans-encoded RNAs that are encoded at a chromosomal location distinct from the RNAs they act upon and generally do not exhibit perfect base-pairing potential with their targets.

Without wishing to be bound by theory, perturbation of an antisense polynucleotide by the antisense oligonucleotides described herein can alter the expression of the corresponding sense messenger RNAs. However, this regulation can either be discordant (antisense knockdown results in messenger RNA elevation) or concordant (antisense knockdown results in concomitant messenger RNA reduction). In these cases, antisense oligonucleotides can be targeted to overlapping or non-overlapping parts of the antisense transcript resulting in its knockdown or sequestration. Coding as well as non-coding antisense can be targeted in an identical manner and that either category is capable of regulating the corresponding sense transcripts—either in a concordant or disconcordant manner. The strategies that are employed in identifying new oligonucleotides for use against a target can be based on the knockdown of antisense RNA transcripts by antisense oligonucleotides or any other means of modulating the desired target.

Strategy 1: In the case of discordant regulation, knocking down the antisense transcript elevates the expression of the conventional (sense) gene. Should that latter gene encode for a known or putative drug target, then knockdown of its antisense counterpart could conceivably mimic the action of a receptor agonist or an enzyme stimulant.

Strategy 2: In the case of concordant regulation, one could concomitantly knock down both antisense and sense transcripts and thereby achieve synergistic reduction of the conventional (sense) gene expression. If, for example, an antisense oligonucleotide is used to achieve knockdown, then this strategy can be used to apply one antisense oligonucleotide targeted to the sense transcript and another antisense oligonucleotide to the corresponding antisense transcript, or a single energetically symmetric antisense oligonucleotide that simultaneously targets overlapping sense and antisense transcripts.

According to the present invention, antisense compounds include antisense oligonucleotides, ribozymes, external guide sequence (EGS) oligonucleotides, siRNA compounds, single- or double-stranded RNA interference (RNAi) compounds such as siRNA compounds, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, doublestranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3" terminus producing an extension of single stranded character. The double stranded compounds optionally can include overhangs on the ends. Further modifications can include conjugate groups attached to one of the termini, selected nucleotide positions, sugar positions or to one of the internuclcoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines, however, in some embodiments, the gene expression or function is up regulated. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

In another embodiment, the desired oligonucleotides or antisense compounds, comprise at least one of: antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof.

dsRNA can also activate gene expression, a mechanism that has been termed "small RNA-induced gene activation" or RNAa. dsRNAs targeting gene promoters induce potent transcriptional activation of associated genes. RNAa was demonstrated in human cells using synthetic dsRNAs, termed "small activating RNAs" (saRNAs).

Small double-stranded RNA (dsRNA), such as small interfering RNA (siRNA) and microRNA (miRNA), have been found to be the trigger of an evolutionary conserved mechanism known as RNA interference (RNAi). RNAi invariably leads to gene silencing. However, in instances described in detail in the examples section which follows, oligonucleotides are shown to increase the expression and/or function of the Pancreatic Developmental gene polynucleotides and encoded products thereof. dsRNAs may also act as small activating RNAs (saRNA). Without wishing to be bound by theory, by targeting sequences in gene promoters. saRNAs would induce target gene expression in a phenomenon referred to as dsRNA-induced transcriptional activation (RNAa).

In a further embodiment, the "target segments" identified herein may be employed in a screen for additional compounds that modulate the expression of a Pancreatic Developmental gene polynucleotide. "Modulators" are those compounds that decrease or increase the expression of a nucleic acid molecule encoding a Pancreatic Developmental gene and which comprise at least a 5-nucleotide portion that is complementary to a target segment. The screening method comprises the steps of contacting a target segment of a nucleic acid molecule encoding sense or natural antisense polynucleotides of a Pancreatic Developmental gene with one or more candidate modulators, and selecting for one or more candidate modulators which decrease or increase the expression of a nucleic acid molecule encoding a Pancreatic Developmental gene polynucleotide, e.g. SEQ ID NOS: 13 to 45. Once it is shown that the candidate modulator or modulators are capable of modulating (e.g. either decreasing or increasing) the expression of a nucleic acid molecule encoding a Pancreatic Developmental gene polynucleotide, the modulator may then be employed in further investigative studies of the function of a Pancreatic Developmental gene polynucleotide, or for use as a research, diagnostic, or therapeutic agent in accordance with the present invention.

Targeting the natural antisense sequence modulates the function of the target gene. For example, the Pancreatic Developmental gene (e.g. accession numbers NM_001025366, NM_001146274, NM_001048, NM_000346, NM_022454, NM_000340, NM_014276, NM_005349, NM_004160, NM_178161, NM_002722, NM_000307, NM_000209, NM_002585, NM_000280, NM_006193, NM_004498, NM_018055, NM_006168, NM_002509, NM_020999, NM_002500, NM_004535, NM_002467, NM_001165255, NM_031944, NM_005461, NM_201589, NM_002276, NM_145805, NM_002202, NM_002196, NM_000207, NM_001185097, NM_001185098, NM_000207, NM_001185097, NM_001185098, NM_002193, NM_000457.3, NM_000458.2, NM_002729.4, NM_005524, NM_001134941, NM_005811, NM_002054, NM_005257, NM_002052, NM_006350, NM_021784, NM_04496, NM_002006, NM_004465, NM_001868, NM_139058, NM_001008221, NM_001106, NM_001616). In an embodiment, the target is an antisense polynucleotide of the Pancreatic Developmental gene. In an embodiment, an antisense oligonucleotide targets sense and/or natural antisense sequences of a Pancreatic Developmental gene polynucleotide (e.g. accession numbers NM_001025366, NM_001146274, NM_001048, NM_000346, NM_022454, NM_000340, NM_014276, NM_005349, NM_004160, NM_178161, NM_002722, NM_000307, NM_000209, NM_002585, NM_000280, NM_006193, NM_004498, NM_018055, NM_006168, NM_002509, NM_020999, NM_002500, NM_004535, NM_002467, NM_001165255, NM_031944, NM_005461, NM_201589, NM_002276, NM_145805, NM_002202, NM_002196, NM_000207, NM_001185097, NM_001185098, NM_000207, NM_001185097, NM_001185098, NM_002193, NM_000457.3, NM_000458.2, NM_002729.4, NM_005524, NM_001134941, NM_005811, NM_002054, NM_005257, NM_002052, NM_006350, NM_021784, NM_004496, NM_002006, NM_004465, NM_001868, NM_139058, NM_001008221, NM_001106, NM_001616), variants, alleles, isoforms, homologs, mutants, derivatives, fragments and complementary sequences thereto. Preferably the oligonucleotide is an antisense molecule and the targets include coding and noncoding regions of antisense and/or sense Pancreatic Developmental gene polynucleotides.

The target segments of the present invention may be also be combined with their respective complementary antisense compounds of the present invention to form stabilized double-stranded (duplexed) oligonucleotides.

Such double stranded oligonucleotide moieties have been shown in the art to modulate target expression and regulate translation as well as RNA processing via an antisense mechanism. Moreover, the double-stranded moieties may be subject to chemical modifications. For example, such double-stranded moieties have been shown to inhibit the target by the classical hybridization of antisense strand of the duplex to the target, thereby triggering enzymatic degradation of the target.

In an embodiment, an antisense oligonucleotide targets Pancreatic Developmental gene polynucleotides (e.g. accession numbers NM_001025366, NM_001146274, NM_001048, NM_000346, NM_022454, NM_000340, NM_014276, NM_005349, NM_004160, NM_178161, NM_002722, NM_000307, NM_000209, NM_002585, NM_000280, NM_006193, NM_004498, NM_018055, NM_006168, NM_002509, NM_020999, NM_002500, NM_004535, NM_002467, NM_001165255, NM_031944, NM_005461, NM_201589, NM_002276, NM_145805, NM_002202, NM_002196, NM_000207, NM_00185097, NM_001185098, NM_000207, NM_001185097, NM_001185098, NM_002193, NM_000457.3, NM_000458.2, NM_002729.4, NM_005524, NM_001134941, NM_005811, NM_002054, NM_005257, NM_002052, NM_006350, NM_021784, NM_004496, NM_002006, NM_004465, NM_001868, NM_139058, NM_001008221, NM_001106, NM_001616), variants, alleles, isoforms, homologs, mutants, derivatives, fragments and complementary sequences thereto. Preferably the oligonucleotide is an antisense molecule.

In accordance with embodiments of the invention, the target nucleic acid molecule is not limited to Pancreatic Developmental gene alone but extends to any of the isoforms, receptors, homologs and the like of a Pancreatic Developmental gene molecule.

In another embodiment, an oligonucleotide targets a natural antisense sequence of a Pancreatic Developmental gene polynucleotide, for example, polynucleotides set forth as SEQ ID NO: 6 to 12, and any variants, alleles, homologs, mutants, derivatives, fragments and complementary sequences thereto. Examples of antisense oligonucleotides are set forth as SEQ ID NOS: 13 to 45.

In one embodiment, the oligonucleotides are complementary to or bind to nucleic acid sequences of a Pancreatic Developmental gene antisense, including without limitation noncoding sense and/or antisense sequences associated with a Pancreatic Developmental gene polynucleotide and modulate expression and/or function of a Pancreatic Developmental gene molecule.

In another embodiment, the oligonucleotides are complementary to or bind to nucleic acid sequences of a Pancreatic Developmental gene natural antisense, set forth as SEQ ID NO: 6 to 12 and modulate expression and/or function of a Pancreatic Developmental gene molecule.

In an embodiment, oligonucleotides comprise sequences of at least 5 consecutive nucleotides of SEQ ID NOS: 13 to 45 and modulate expression and/or function of a Pancreatic Developmental gene molecule.

The polynucleotide targets comprise Pancreatic Developmental gene, including family members thereof, variants of a Pancreatic Developmental gene; mutants of a Pancreatic Developmental gene, including SNPs; noncoding sequences of a Pancreatic Developmental gene; alleles of a Pancreatic Developmental gene; species variants, fragments and the like. Preferably the oligonucleotide is an antisense molecule.

In another embodiment, the oligonucleotide targeting Pancreatic Developmental gene polynucleotides, comprise: antisense RNA, interference RNA (RNAi), short interfering RNA (siRNA); micro interfering RNA (miRNA); a small, temporal RNA (stRNA); or a short, hairpin RNA (shRNA); small RNA-induced gene activation (RNAa); or, small activating RNA (saRNA).

In another embodiment, targeting of a Pancreatic Developmental gene polynucleotide, e.g. SEQ ID NO: 6 to 12 modulate the expression or function of these targets. In one embodiment, expression or function is up-regulated as compared to a control. In another embodiment, expression or function is down-regulated as compared to a control.

In another embodiment, antisense compounds comprise sequences set forth as SEQ ID NOS: 13 to 45. These oligonucleotides can comprise one or more modified nucleotides, shorter or longer fragments, modified bonds and the like.

In another embodiment, SEQ ID NOS: 13 to 45 comprise one or more LNA nucleotides.

The modulation of a desired target nucleic acid can be carried out in several ways known in the art. For example, antisense oligonucleotides, siRNA etc. Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript.

Because of their sequence-specificity, trans-cleaving enzymatic nucleic acid molecules show promise as therapeutic agents for human disease. Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies have been used to evolve new nucleic acid catalysts capable of catalyzing a variety of reactions, such as cleavage and ligation of phosphodiester linkages and amide linkages.

The development of ribozymes that are optimal for catalytic activity would contribute significantly to any strategy that employs RNA-cleaving ribozymes for the purpose of regulating gene expression. The hammerhead ribozyme, for example, functions with a catalytic rate (kcat) of about 1 min-1 in the presence of saturating (10 mM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain selfcleaving ribozymes may be optimized to give maximal catalytic activity, or that entirely new RNA motifs can be made that display significantly faster rates for RNA phosphodiester cleavage.

Intermolecular cleavage of an RNA substrate by an RNA catalyst that fits the "hammerhead" model was first shown in 1987. The RNA catalyst was recovered and reacted with multiple RNA molecules, demonstrating that it was truly catalytic.

Catalytic RNAs designed based on the "hammerhead" motif have been used to cleave specific target sequences by making appropriate base changes in the catalytic RNA to maintain necessary base pairing with the target sequences. This has allowed use of the catalytic RNA to cleave specific target sequences and indicates that catalytic RNAs designed according to the "hammerhead" model may possibly cleave specific substrate RNAs in vivo.

RNA interference (RNAi) has become a powerful tool for modulating gene expression in mammals and mammalian cells. This approach requires the delivery of small interfering RNA (siRNA) either as RNA itself or as DNA, using an expression plasmid or virus and the coding sequence for small hairpin RNAs that are processed to siRNAs. This system enables efficient transport of the pre-siRNAs to the cytoplasm where they are active and permit the use of regulated and tissue specific promoters for gene expression.

In one embodiment, an oligonucleotide or antisense compound comprises an oligomer or polymer of ribonucleic acid (RNA) and/or deoxyribonucleic acid (DNA), or a mimetic, chimera, analog or homolog thereof. This term includes oligonucleotides composed of naturally occurring nucleotides, sugars and covalent internuclcoside (backbone) linkages as well as oligonucleotides having non-naturally occurring portions which function similarly. Such modified or substituted oligonucleotides are often desired over native forms because of desirable properties such as, for example, enhanced cellular uptake, enhanced affinity for a target nucleic acid and increased stability in the presence of nucleases.

According to the present invention, the oligonucleotides or "antisense compounds" include antisense oligonucleotides (e.g. RNA, DNA, mimetic, chimera, analog or homolog thereof), ribozymes, external guide sequence (EGS) oligonucleotides, siRNA compounds, single- or double-stranded RNA interference (RNAi) compounds such as siRNA compounds, saRNA, aRNA, and other oligomeric compounds which hybridize to at least a portion of the target nucleic acid and modulate its function. As such, they may be DNA, RNA, DNA-like, RNA-like, or mixtures thereof, or may be mimetics of one or more of these. These compounds may be single-stranded, double-stranded, circular or hairpin oligomeric compounds and may contain structural elements such as internal or terminal bulges, mismatches or loops. Antisense compounds are routinely prepared linearly but can be joined or otherwise prepared to be circular and/or branched. Antisense compounds can include constructs such as, for example, two strands hybridized to form a wholly or partially double-stranded compound or a single strand with sufficient self-complementarity to allow for hybridization and formation of a fully or partially double-stranded compound. The two strands can be linked internally leaving free 3' or 5' termini or can be linked to form a continuous hairpin structure or loop. The hairpin structure may contain an overhang on either the 5' or 3' terminus producing an extension of single stranded character. The double stranded compounds optionally can include overhangs on the ends. Further modifications can include conjugate groups attached to one of the termini, selected nucleotide positions, sugar positions or to one of the internuclcoside linkages. Alternatively, the two strands can be linked via a non-nucleic acid moiety or linker group. When formed from only one strand, dsRNA can take the form of a self-complementary hairpin-type molecule that doubles back on itself to form a duplex. Thus, the dsRNAs can be fully or partially double stranded. Specific modulation of gene expression can be achieved by stable expression of dsRNA hairpins in transgenic cell lines. When formed from two strands, or a single strand that takes the form of a self-complementary hairpin-type molecule doubled back on itself to form a duplex, the two strands (or duplex-forming regions of a single strand) are complementary RNA strands that base pair in Watson-Crick fashion.

Once introduced to a system, the compounds of the invention may elicit the action of one or more enzymes or structural proteins to effect cleavage or other modification of the target nucleic acid or may work via occupancy-based mechanisms. In general, nucleic acids (including oligonucleotides) may be described as "DNA-like" (i.e., generally having one or more 2'-deoxy sugars and, generally, T rather than U bases) or "RNA-like" (i.e., generally having one or more 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-formlike structure are "RNA-like." In some (chimeric) embodiments, an antisense compound may contain both A- and B-form regions.

The antisense compounds in accordance with this invention can comprise an antisense portion from about 5 to about 80 nucleotides (i.e. from about 5 to about 80 linked nucleosides) in length. This refers to the length of the antisense strand or portion of the antisense compound. In other words, a single-stranded antisense compound of the invention comprises from 5 to about 80 nucleotides, and a double-stranded antisense compound of the invention (such as a dsRNA, for example) comprises a sense and an antisense strand or portion of 5 to about 80 nucleotides in length. One of ordinary skill in the art will appreciate that this comprehends antisense portions of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleotides in length, or any range therewithin.

In one embodiment, the antisense compounds of the invention have antisense portions of 10 to 50 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range therewithin. In some embodiments, the oligonucleotides are 15 nucleotides in length.

In one embodiment, the antisense or oligonucleotide compounds of the invention have antisense portions of 12 or 13 to 30 nucleotides in length. One having ordinary skill in the art will appreciate that this embodies antisense compounds having antisense portions of 12, 13, 14, 15, 16, 17, 18, 19, 20, 21, 22, 23, 24, 25, 26, 27, 28, 29 or 30 nucleotides in length, or any range therewithin.

In another embodiment, the oligomeric compounds of the present invention also include variants in which a different base is present at one or more of the nucleotide positions in the compound. For example, if the first nucleotide is an adenosine, variants may be produced which contain thymidine, guanosine or cytidine at this position. This may be done at any of the positions of the antisense or dsRNA compounds. These compounds are then tested using the methods described herein to determine their ability to inhibit expression of a target nucleic acid.

In some embodiments, homology, sequence identity or complementarity, between the antisense compound and target is from about 40% to about 60%. In some embodiments, homology, sequence identity or complementarity, is from about 60% to about 70%. In some embodiments, homology, sequence identity or complementarity, is from about 70% to about 80%. In some embodiments, homology, sequence identity or complementarity, is from about 80% to about 90%. In some embodiments, homology, sequence identity or complementarity, is about 90%, about 92%, about 94%, about 95%, about 96%, about 97%, about 98%, about 99% or about 100%.

In another embodiment, the antisense oligonucleotides, such as for example, nucleic acid molecules set forth in SEQ ID NOS: 6 to 45 comprise one or more substitutions or modifications. In one embodiment, the nucleotides are substituted with locked nucleic acids (LNA).

In another embodiment, the oligonucleotides target one or more regions of the nucleic acid molecules sense and/or antisense of coding and/or non-coding sequences associated with Pancreatic Developmental gene and the sequences set forth as SEQ ID NOS: 1 to 12. The oligonucleotides are also targeted to overlapping regions of SEQ ID NOS: 1 to 12.

Certain oligonucleotides of this invention are chimeric oligonucleotides. "Chimeric oligonucleotides" or "chimeras," in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense modulation of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art. In one embodiment, a chimeric oligonucleotide comprises at least one region modified to increase target binding affinity, and, usually, a region that acts as a substrate for RNAse H. Affinity of an oligonucleotide for its target (in this case, a nucleic acid encoding ras) is routinely determined by measuring the Tm of an oligonucleotide/target pair, which is the temperature at which the oligonucleotide and target dissociate; dissociation is detected spectrophotometrically. The higher the Tm, the greater is the affinity of the oligonucleotide for the target.

Chimeric antisense compounds of the invention may be formed as composite structures of two or more oligonucleotides, modified oligonucleotides, oligonucleosides and/or oligonucleotides mimetics as described above. Such; compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein incorporated by reference.

In another embodiment, the region of the oligonucleotide which is modified comprises at least one nucleotide modified at the 2' position of the sugar, most preferably a 2'-Oalkyl, 2'-O-alkyl-O-alkyl or 2'-fluoro-modified nucleotide. In other embodiments, RNA modifications include 2'-fluoro, 2'-amino and 2' O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target. The effect of such increased affinity is to greatly enhance RNAi oligonucleotide inhibition of gene expression. RNAse H is a cellular endonuclease that cleaves the RNA strand of RNA: DNA duplexes; activation of this enzyme therefore results in cleavage of the RNA target, and thus can greatly enhance the efficiency of RNAi inhibition. Cleavage of the RNA target can be routinely demonstrated by gel electrophoresis. In another embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance. Some desirable modifications can be found in Dc Mesmacker et. al. (1995) Acc. Chem. Res., 28:366-374.

Specific examples of some oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most are oligonucleotides with phosphorothioate backbones and those with heteroatom backbones, particularly CH2-NH—O—CH2, CH, —N(CH3)-O—CH2 [known as a methylene(methylimino) or MMI backbone], CH2-O—N (CH3)-CH2, CH2-N (CH3)-N (CH3)-CH2 and O—N (CH3)-CH2-CH2 backbones, wherein the native phosphodiester backbone is represented as O—P—O—CH,). The amide backbones disclosed by Dc Mesmacker et al. (1995) Acc. Chem. Res. 28:366-374 are also preferred. Also are oligonucleotides having morpholino backbone structures (Summerton and Weller, U.S. Pat. No. 5,034,506). In other embodiments, such as the peptide nucleic acid (PNA) backbone, the phosphodiester backbone of the oligonucleotide is replaced with a polyamide backbone, the nucleotides being bound directly or indirectly to the aza nitrogen atoms of the polyamide backbone. Oligonucleotides may also comprise one or more substituted sugar moieties, oligonucleotides comprise one of the following at the 2' position: OH, SH, SCH3, F, OCN, OCH3 OCH3, OCH3 O(CH2)n CH3, O(CH2)n NH2 or O(CH2)n CH3 where n is from 1 to about 10; C1 to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A modification includes 2'-methoxyethoxy [2'-O—CH2 CH2 OCH3, also known as 2'-O-(2-methoxyethyl)]. Other modifications include 2'-methoxy (2'-O—CH3), 2'-propoxy (2'-OCH2 CH2CH3) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetic such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleotides include adenine (A), guanine (G), thymine (T), cytosine (C) and uracil (U). Modified nucleotides include nucleotides found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the an as 5-Me-C), 5-hydroxymethylcytosine (HMC), glycosyl HMC and gentobiosyl HMC, as well as synthetic nucleotides, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine and 2,6-diaminopurine. A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety, a hexyl, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid. Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, the nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of one of ordinary skill in the art. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

In accordance with the invention, use of modifications such as the use of LNA monomers to enhance the potency, specificity and duration of action and broaden the routes of administration of oligonucleotides comprised of current chemistries such as MOE, ANA, FANA, PS etc. This can be achieved by substituting some of the monomers in the current oligonucleotides by LNA monomers. The LNA modified oligonucleotide may have a size similar to the parent compound or may be larger or preferably smaller. It is that such LNA-modified oligonucleotides contain less than about 70%, more preferably less than about 60%, most preferably less than about 50% LNA monomers and that their sizes are between about 5 and 25 nucleotides, more preferably between about 12 and 20 nucleotides.

Modified oligonucleotide backbones comprise, but are not limited to, phosphorothioates, chiral phosphorothioates, phosphotriesters, phosphotriesters, aminoalkylphosphotriesters, methyl and other alkyl phosphonates comprising 3'alkylene phosphonates and chiral phosphonates, phosphinates, phosphoramides comprising 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative United States patents that teach the preparation of the above phosphorus containing linkages comprise, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

Modified oligonucleotide backbones that do not include a phosphorus atom therein have backbones that are formed by short chain alkyl or cycloalkyl internuclcoside linkages, mixed heteroatom and alkyl or cycloalkyl internuclcoside linkages, or one or more short chain heteroatomic or heterocyclic internuclcoside linkages. These comprise those having morpholino linkages (formed in part from the sugar portion of a nucleoside): siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Representative United States patents that teach die preparation of the above oligonucleosides comprise, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

In other oligonucleotide mimetic, both the sugar and the internuclcoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach die preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen, et al. (1991) *Science* 254, 1497-1500.

In another embodiment of the invention the oligonucleotides with phosphorothioate backbones and oligonucleosides with heteroatom backbones, and in particular-CH2-NH—O—CH2-, —CH2-N(CH3)-O—CH2-known as a methylene (methylamine) or MMI backbone, —CH2-O—N (CH3)-CH2-, —CH2N(CH3)-N(CH3) CH2-and-O—N (CH3)-CH2-CH2- wherein the native phosphodiester backbone is represented as —O—P—O—CH2- of the above referenced U.S. Pat. No. 5,489,677, and the amide backbones of the above referenced U.S. Pat. No. 5,602,240. Also are oligonucleotides having morpholino backbone structures of the above-referenced U.S. Pat. No. 5,034,506.

Modified oligonucleotides may also contain one or more substituted sugar moieties, oligonucleotides comprise one of the following at the 2' position: OH; F; O-, S-, or N-alkyl; O-, S-, or N-alkenyl; O-, S- or N-alkynyl; or O alkyl-O-alkyl, wherein the alkyl, alkenyl and alkynyl may be substituted or unsubstituted C to CO alkyl or C2 to CO alkenyl and alkynyl. Particularly are O (CH2)n OmCH3, O(CH2)n, OCH3, O(CH2)nNH2, O(CH2)nCH3, O(CH2)nONH2, and O(CH2nON(CH2)nCH3)2 where n and m can be from 1 to about 10. Other oligonucleotides comprise one of the following at the 2' position: C to CO, (lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A modification comprises 2'-methoxyethoxy (2-O—CH2CH2OCH3, also known as 2'-O-(2-methoxyethyl) or 2'-MOE) i.e., an alkoxyalkoxy group. A further modification comprises 2'-dimethylaminoethoxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2.

Other modifications comprise 2'-methoxy (2'-OCH3), 2'-aminopropoxy (2'-O CH2CH2CH2NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetic such as cyclobutyl moieties in place of the pentofuranosyl sugar. Representative United States patents that teach the preparation of such modified sugar structures comprise, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Oligonucleotides may also comprise nucleobase (often referred to in the art simply as "base") modifications or substitutions. As used herein, "unmodified" or "natural" nucleotides comprise the purine bases adenine (A) and guanine (G), and the pyrimidine bases thymine (T), cytosine (C) and uracil (U). Modified nucleotides comprise other synthetic and natural nucleotides such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylquanine and 7-methyladenine, 8-azaguanine and 8-azaadenine, 7-deazaguanine and 7-deazaadenine and 3-deazaguanine and 3-deazaadenine.

Further, nucleotides comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et. al., 'Angewandle Chemie, International Edition', 1991, 30, page 613, and those disclosed by Sanghvi, Y. S., Chapter 15, 'Antisense Research and Applications', pages 289-302, Crooke, S. T. and Lebleu, B. ea., CRC Press, 1993. Certain of these nucleotides are particularly useful for increasing the binding affinity of the oligomeric compounds of the invention. These comprise 5-substituted pyrimidines, 6-azapyrimidines and N-2, N-6 and 0-6 substituted purines, comprising 2-aminopropyladenine, 5-propynyluracil and 5-propynylcytosine, 5-methylcytosine substitutions have been shown to increase nucleic acid duplex stability by 0.6-1.2° C. (Sanghvi, Y. S., Crooke, S. T. and Lebleu, B., eds, 'Antisense Research and Applications', CRC Press, Boca Raton, 1993, pp. 276-278) and are presently base substitutions, even more particularly when combined with 2'-Omethoxyethyl sugar modifications.

Representative United States patents that teach the preparation of the above noted modified nucleotides as well as other modified nucleotides comprise, but are not limited to, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,596,091; 5,614,617; 5,750,692, and 5,681,941, each of which is herein incorporated by reference.

Another modification of the oligonucleotides of the invention involves chemically linking to the oligonucleotide one or more moieties or conjugates, which enhance the activity, cellular distribution, or cellular uptake of the oligonucleotide.

Such moieties comprise but are not limited to, lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-t-oxycholesterol moiety.

Representative United States patents that teach the preparation of such oligonucleotides conjugates comprise, but are not limited to, U.S. Pat. Nos. 4,828,979; 4,948,882; 5,218, 105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, each of which is herein incorporated by reference.

Drug Discovery:

The compounds of the present invention can also be applied in the areas of drug discovery and target validation. The present invention comprehends the use of the compounds and target segments identified herein in drug discovery efforts to elucidate relationships that exist between a Pancreatic Developmental gene polynucleotide and a disease state, phenotype, or condition. These methods include detecting or modulating a Pancreatic Developmental gene polynucleotide comprising contacting a sample, tissue, cell, or organism with the compounds of the present invention, measuring the nucleic acid or protein level of a Pancreatic Developmental gene polynucleotide and/or a related phenotypic or chemical endpoint at some time after treatment, and optionally comparing the measured value to a non-treated sample or sample treated with a further compound of the invention. These methods can also be performed in parallel or in combination with other experiments to determine the function of unknown genes for the process of target validation or to determine the validity of a particular gene product as a target for treatment or prevention of a particular disease, condition, or phenotype.

Assessing Up-Regulation or Inhibition of Gene Expression:

Transfer of an exogenous nucleic acid into a host cell or organism can be assessed by directly detecting the presence of the nucleic acid in the cell or organism. Such detection can be achieved by several methods well known in the art. For example, the presence of the exogenous nucleic acid can be detected by Southern blot or by a polymerase chain reaction (PCR) technique using primers that specifically amplify nucleotide sequences associated with the nucleic acid. Expression of the exogenous nucleic acids can also be measured using conventional methods including gene expression analysis. For instance, mRNA produced from an exogenous nucleic acid can be detected and quantified using a Northern blot and reverse transcription PCR (RT-PCR).

Expression of RNA from the exogenous nucleic acid can also be detected by measuring an enzymatic activity or a reporter protein activity. For example, antisense modulatory activity can be measured indirectly as a decrease or increase in target nucleic acid expression as an indication that the exogenous nucleic acid is producing the effector RNA. Based on sequence conservation, primers can be designed and used to amplify coding regions of the target genes. Initially, the most highly expressed coding region from each gene can be used to build a model control gene, although any coding or non coding region can be used. Each control gene is assembled by inserting each coding region between a reporter coding region and its poly(A) signal. These plasmids would produce an mRNA with a reporter gene in the upstream portion of the gene and a potential RNAi target in the 3' non-coding region. The effectiveness of individual antisense oligonucleotides would be assayed by modulation of the reporter gene. Reporter genes useful in the methods of the present invention include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), red fluorescent protein (RFP), yellow fluorescent protein (YFP), cyan fluorescent protein (CFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracycline. Methods to determine modulation of a reporter gene are well known in the art, and include, but are not limited to, fluorometric methods (e.g. fluorescence spectroscopy Fluorescence Activated Cell Soiling (FACS), fluorescence microscopy), antibiotic resistance determination.

NEUROD1, HNF4A, MAFA, PDX1. NKX6-1 proteins and mRNA expression can be assayed using methods known to those of skill in the an and described elsewhere herein. For example, immunoassays such as the ELISA can be used to measure protein levels. Pancreatic Developmental gene antibodies for ELISAs are available commercially, e.g., from R&D Systems (Minneapolis, Minn.), Abeam, Cambridge, Mass.

In embodiments, NEUROD1, HNF4A, MAFA, PDX1, NKX6-1 expression (e.g., mRNA or protein) in a sample (e.g., cells or tissues in vivo or in vitro) treated using an antisense oligonucleotide of the invention is evaluated by comparison with Pancreatic Developmental gene expression in a control sample. For example, expression of the protein or nucleic acid can be compared using methods known to those of skill in the an with that in a mock-treated or untreated sample. Alternatively, comparison with a sample treated with a control antisense oligonucleotide (e.g., one having an altered or different sequence) can be made depending on the information desired. In another embodiment, a difference in the expression of the Pancreatic Developmental gene protein or nucleic acid in a treated vs. an untreated sample can be compared with the difference in expression of a different nucleic acid (including any standard deemed appropriate by the researcher, e.g., a housekeeping gene) in a treated sample vs. an untreated sample.

Observed differences can be expressed as desired, e.g., in the form of a ratio or fraction, for use in a comparison with control. In embodiments, the level of a Pancreatic Developmental gene mRNA or protein, in a sample treated with an antisense oligonucleotide of the present invention, is increased or decreased by about 1.25-fold to about 10-fold or more relative to an untreated sample or a sample treated with a control nucleic acid. In embodiments, the level of a Pancreatic Developmental gene mRNA or protein is increased or decreased by at least about 1.25-fold, at least about 1.3-fold, at least about 1.4-fold, at least about 1.5-fold, at least about 1.6-fold, at least about 1.7-fold, at least about 1.8-fold, at least about 2-fold, at least about 2.5-fold, at least about 3-fold, at least about 3.5-fold, at least about 4-fold, at least about 4.5-fold, at least about 5-fold, at least about 5.5-fold, at least about 6-fold, at least about 6.5-fold, at least about 7-fold, at least about 7.5-fold, at least about 8-fold, at least about 8.5-fold, at least about 9-fold, at least about 9.5-fold, or at least about 10-fold or more.

Kits, Research Reagents, Diagnostics, and Therapeutics

The compounds of the present invention can be utilized for diagnostics, therapeutics, and prophylaxis, and as research reagents and components of kits. Furthermore, antisense oligonucleotides, which are able to inhibit gene expression with exquisite specificity, are often used by those of ordinary skill to elucidate the function of particular genes or to distinguish between functions of various members of a biological pathway.

For use in kits and diagnostics and in various biological systems, the compounds of the present invention, either alone or in combination with other compounds or therapeutics, are useful as tools in differential and/or combinatorial analyses to elucidate expression patterns of a portion or die entire complement of genes expressed within cells and tissues.

As used herein the term "biological system" or "system" is defined as any organism, cell, cell culture or tissue that expresses, or is made competent to express products of the Pancreatic Developmental genes. These include, but are not limited to, humans, transgenic animals, cells, cell cultures, tissues, xenografts, transplants and combinations thereof.

As one non limiting example, expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds that affect expression patterns.

Examples of methods of gene expression analysis known in the art include DNA arrays or microarrays (Brazma and Vilo, (2000) *FEBS Lett.,* 480, 17-24; Celis, et al., (2000) *FEBS Lett.,* 480, 2-16), SAGE (serial analysis of gene expression) (Madden, et al., (2000) Drug Discov. Today, 5, 415-425), READS (restriction enzyme amplification of digested cDNAs) (Prashar and Weissman, (1999) *Methods Enzymol.,* 303, 258-72), TOGA (total gene expression analysis) (Sutcliffe, et al., (2000) *Proc. Natl. Acad. Sci. U.S.A.,* 97, 1976-81), protein arrays and proteomics (Celis, et al., (2000) *FEBS Lett.,* 480, 2-16; Jungblut, et al., Electrophoresis, 1999, 20, 2100-10), expressed sequence tag (EST) sequencing (Celis, et al., *FEBS Lett.,* 2000, 480, 2-16; Larsson, et al., J. Biotechnol., 2000, 80, 143-57), subtractive RNA fingerprinting (SuRF) (Fuchs, et al., (2000) Anal. Biochem. 286, 91-98; Larson, et al., (2000) *Cytometry*, 41, 203-208), subtractive cloning, differential display (DD) (Jurecic and Belmont, (2000) *Curr. Opin. Microbiol.* 3, 316-21), comparative genomic hybridization (Carulli, et al. (1998) *J. Cell Biochem. Suppl.*, 31, 286-96), FISH (fluorescent in situ hybridization) techniques (Going and Gusterson, (1999) *Eur. J. Cancer,* 35, 1895-904) and mass spectrometry methods (To, Comb. (2000) *Chem. High Throughput Screen,* 3, 235-41).

The compounds of the invention are useful for research and diagnostics, because these compounds hybridize to nucleic acids encoding a Pancreatic Developmental gene. For example, oligonucleotides that hybridize with such efficiency and under such conditions as disclosed herein as to be effective Pancreatic Developmental gene modulators are effective primers or probes under conditions favoring gene amplification or detection, respectively. These primers and probes are useful in methods requiring the specific detection of nucleic acid molecules encoding a Pancreatic Developmental gene and in the amplification of said nucleic acid molecules for detection or for use in further studies of a Pancreatic Developmental gene. Hybridization of the antisense oligonucleotides, particularly the primers and probes, of the invention with a nucleic acid encoding a Pancreatic Developmental gene can be detected by means known in the art. Such means may include conjugation of an enzyme to the oligonucleotide, radiolabeling of the oligonucleotide, or any other suitable detection means. Kits using such detection means for detecting the level of a Pancreatic Developmental gene in a sample may also be prepared.

The specificity and sensitivity of antisense are also harnessed by those of skill in the art for therapeutic uses. Antisense compounds have been employed as therapeutic moieties in the treatment of disease states in animals, including humans. Antisense oligonucleotide drugs have been safely and effectively administered to humans and numerous clinical trials are presently underway. It is thus established that antisense compounds can be useful therapeutic modalities that can be configured to be useful in treatment regimes for the treatment of cells, tissues and animals, especially humans.

For therapeutics, an animal, preferably a human, suspected of having a disease or disorder which can be treated by modulating the expression of a Pancreatic Developmental gene polynucleotide is treated by administering antisense compounds in accordance with this invention. For example, in one non-limiting embodiment, the methods comprise the step of administering to the animal in need of treatment, a therapeutically effective amount of a Pancreatic Developmental gene modulator. The Pancreatic Developmental gene modulators of the present invention effectively modulate the activity of a Pancreatic Developmental gene or modulate the expression of a Pancreatic Developmental gene protein. In one embodiment, the activity or expression of a Pancreatic Developmental gene in an animal is inhibited by about 10% as compared to a control. Preferably, the activity or expression of a Pancreatic Developmental gene in an animal is inhibited by about 30%. More preferably, the activity or expression of a Pancreatic Developmental gene in an animal is inhibited by 50% or more. Thus, the oligomeric compounds modulate expression of a Pancreatic Developmental gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

In one embodiment, the activity or expression of a Pancreatic Developmental gene and/or in an animal is increased by about 10% as compared to a control. Preferably, the activity or expression of a Pancreatic Developmental gene in an animal is increased by about 30%. More preferably, the activity or expression of a Pancreatic Developmental gene in an animal is increased by 50% or more. Thus, the oligomeric compounds modulate expression of a Pancreatic Developmental gene mRNA by at least 10%, by at least 50%, by at least 25%, by at least 30%, by at least 40%, by at least 50%, by at least 60%, by at least 70%, by at least 75%, by at least 80%, by at least 85%, by at least 90%, by at least 95%, by at least 98%, by at least 99%, or by 100% as compared to a control.

For example, the reduction of the expression of a Pancreatic Developmental gene may be measured in scrum, blood, adipose tissue, liver or any other body fluid, tissue or organ of the animal. Preferably, the cells contained within said fluids, tissues or organs being analyzed contain a nucleic acid molecule encoding Pancreatic Developmental gene peptides and/or the Pancreatic Developmental gene protein itself.

The compounds of the invention can be utilized in pharmaceutical compositions by adding an effective amount of a compound to a suitable pharmaceutically acceptable diluent or carrier. Use of the compounds and methods of the invention may also be useful prophylactically.

Conjugates:

Another modification of the oligonucleotides of the invention involves chemically linking to the oligonucleotide one or more moieties or conjugates that enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a hexyl, e.g., hexyl-5-tritylthiol, a thiocholesterol, an aliphatic chain, e.g., dodecandiol or undecyl residues, a phospholipid, e.g., di-hexadecyl-rac-glycerol or triethylammonium 1,2-di-O-hexadecyl-rac-glycero-3-Hphosphonate, a polyamine or a polyethylene glycol chain, or adamantane acetic acid, a palmityl moiety, or an octadecylamine or hexylamino-carbonyl-oxycholesterol moiety. Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3, 5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic.

Representative United States patents that teach the preparation of such oligonucleotides conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

Formulations:

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,165; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

Although, the antisense oligonucleotides do not need to be administered in the context of a vector in order to modulate a target expression and/or function, embodiments of the invention relates to expression vector constructs for the expression of antisense oligonucleotides, comprising promoters, hybrid promoter gene sequences and possess a strong constitutive promoter activity, or a promoter activity which can be induced in the desired case.

In an embodiment, invention practice involves administering at least one of the foregoing antisense oligonucleotides with a suitable nucleic acid delivery system. In one embodiment, that system includes a nonviral vector operably linked to the polynucleotide. Examples of such nonviral vectors include the oligonucleotide alone (e.g. any one or more of SEQ ID NOS: 13 to 45) or in combination with a suitable protein, polysaccharide or lipid formulation.

Additionally suitable nucleic acid delivery systems include viral vector, typically sequence from at least one of an adenovirus, adenovirus-associated virus (AAV), helper-dependent adenovirus, retrovirus, or hemagglutinatin virus of Japan-liposome (HVJ) complex. Preferably, the viral vector comprises a strong eukaryotic promoter operably linked to the polynucleotide e.g., a cytomegalovirus (CMV) promoter.

Additionally vectors include viral vectors, fusion proteins and chemical conjugates. Retroviral vectors include Moloney murine leukemia viruses and HIV-based viruses. One HIV-based viral vector comprises at least two vectors wherein the gag and pol genes are from an HIV genome and the env gene is from another virus. DNA viral vectors are preferred. These vectors include pox vectors such as orthopox or avipox vectors, herpesvirus vectors such as a herpes simplex I virus (HSV) vector, Adenovirus Vectors and Adeno-associated Virus Vectors).

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of die compounds of the invention: i.e., salts that retain the desired biological activity of the parent compound and do not impart undesired toxicological effects thereto. For oligonucleotides, examples of pharmaceutically acceptable salts and their uses are further described in U.S. Pat. No. 6,287,860, which is incorporated herein by reference.

The present invention also includes pharmaceutical compositions and formulations that include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration.

For treating tissues in the central nervous system, administration can be made by, e.g., injection or infusion into the cerebrospinal fluid. Administration of antisense RNA into cerebrospinal fluid is described, e.g., in U.S. Pat. App. Pub. No. 2007/0117772, "Methods for slowing familial ALS disease progression," incorporated herein by reference in its entirety.

When it is intended that the antisense oligonucleotide of the present invention be administered to cells in the central nervous system, administration can be with one or more agents capable of promoting penetration of the subject antisense oligonucleotide across the blood-brain barrier. Injection can be made, e.g., in the entorhinal cortex or hippocampus. Delivery of neurotrophic factors by administration of an adenovirus vector to motor neurons in muscle tissue is described in, e.g., U.S. Pat. No. 6,632,427, "Adenoviral-vector-mediated gene transfer into medullary motor neurons," incorporated herein by reference. Delivery of vectors directly to the brain, e.g., the striatum, the thalamus, the hippocampus, or the substantia nigra, is known in the art and described, e.g., in U.S. Pat. No. 6,756,523, "Adenovirus vectors for the transfer of foreign genes into cells of the central nervous system particularly in brain," incorporated herein by reference. Administration can be rapid as by injection or made over a period of time as by slow infusion or administration of slow release formulations.

The subject antisense oligonucleotides can also be linked or conjugated with agents that provide desirable pharmaceutical or pharmacodynamic properties. For example, the antisense oligonucleotide can be coupled to any substance, known in the art to promote penetration or transport across the blood-brain barrier, such as an antibody to the transferrin receptor, and administered by intravenous injection. The antisense compound can be linked with a viral vector, for example, that makes the antisense compound more effective and/or increases the transport of the antisense compound across the blood-brain barrier. Osmotic blood brain barrier disruption can also be accomplished by, e.g., infusion of sugars including, but not limited to, meso erythritol, xylitol, D(+) galactose, D(+) lactose, D(+) xylose, dulcitol, myo-inositol, L(−) fructose, D(−) mannitol, D(+) glucose, D(+) arabinose, D(−) arabinose, cellobiose, D(+) maltose, D(+)

raffinose, L(+) rhamnose, D(+) melibiose. D(−) ribose, adonitol, D(+) arabitol, L(−) arabitol, D(+) fucose, L(−) fucose, D(−) lyxose, L(+) lyxose, and L(−) lyxose, or amino acids including, but not limited to, glutamine, lysine, arginine, asparagine, aspartic acid, cysteine, glutamic acid, glycine, histidine, leucine, methionine, phenylalanine, proline, serine, threonine, tyrosine, valine, and taurine. Methods and materials for enhancing blood brain barrier penetration are described, e.g., in U.S. Pat. No. 4,866,042, "Method for the delivery of genetic material across the blood brain barrier," U.S. Pat. No. 6,294,520, "Material for passage through the blood-brain barrier," and U.S. Pat. No. 6,936,589, "Parenteral delivery systems," all incorporated herein by reference in their entirety.

The subject antisense compounds may be admixed, encapsulated, conjugated or otherwise associated with other molecules, molecule structures or mixtures of compounds, for example, liposomes, receptor-targeted molecules, oral, rectal, topical or other formulations, for assisting in uptake, distribution and/or absorption. For example, cationic lipids may be included in the formulation to facilitate oligonucleotide uptake. One such composition shown to facilitate uptake is LIPOFECTIN (available from GIBCO-BRL, Bethesda, Md.).

Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carriers) or excipient(s). In general, the formulations are prepared by uniformly and intimately bringing into association die active ingredients with liquid carriers or finely divided solid earners or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogeneous systems of one liquid dispersed in another in the form of droplets usually exceeding 0.1 μm in diameter. Emulsions may contain additional components in addition to the dispersed phases, and the active drug that may be present as a solution in either the aqueous phase, oily phase or itself as a separate phase. Microemulsions are included as an embodiment of the present invention. Emulsions and their uses are well known in the art and are further described in U.S. Pat. No. 6,287,860.

Formulations of the present invention include liposomal formulations. As used in the present invention, the term "liposome" means a vesicle composed of amphiphilic lipids arranged in a spherical bilayers or bilayers. Liposomes are unilamellar or multilamellar vesicles which have a membrane formed from a lipophilic material and an aqueous interior that contains the composition to be delivered. Cationic liposomes are positively charged liposomes that are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids. When incorporated into liposomes, these specialized lipids result in liposomes with enhanced circulation lifetimes relative to liposomeslacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein by reference.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs Penetration enhancers may be classified as belonging to one of five broad categories, i.e., surfactants, fatty acids, bile salts, chelating agents, and non-chelating nonsurfactants. Penetration enhancers and their uses are further described in U.S. Pat. No. 6,287,860, which is incorporated herein by reference.

One of skill in the art will recognize that formulations are routinely designed according to their intended use, i.e. route of administration.

formulations for topical administration include those in which the oligonucleotides of the invention are in admixture with a topical delivery agent such as lipids, liposomes, fatty acids, fatty acid esters, steroids, chelating agents and surfactants, lipids and liposomes include neutral (e.g. diolcoyl-phosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and diolcoyl-phosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids, fatty acids and esters, pharmaceutically acceptable salts thereof, and their uses are further described in U.S. Pat. No. 6,287,860.

Compositions and formulations for oral administration include powders or granules, microparticulates, nanoparticulates, suspensions or solutions in water or non-aqueous media, capsules, gel capsules, sachets, tablets or minitablets.

Thickeners, flavoring agents, diluents, emulsifiers, dispersing aids or binders may be desirable, oral formulations are those in which oligonucleotides of the invention are administered in conjunction with one or more penetration enhancers surfactants and chelators, surfactants include fatty acids and/or esters or salts thereof, bile acids and/or salts thereof, bile acids/salts and fatty acids and their uses are further described in U.S. Pat. No. 6,287,860, which is incorporated herein by reference. Also are combinations of penetration enhancers, for example, fatty acids/salts in combination with bile acids/salts. A particularly combination is the sodium salt of lauric acid, capric acid and polyoxyethylene. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein by reference.

Compositions and formulations for parenteral, intrathecal or intraventricular administration may include sterile aqueous solutions that may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents that function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bischloroethyl-nitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclo-phosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Antiinflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. For example, the first target may be a particular antisense sequence of a Pancreatic Developmental gene, and the second target may be a region from another nucleotide sequence. Alternatively, compositions of the invention may contain two or more antisense compounds targeted to different regions of the same Pancreatic Developmental gene nucleic acid target. Numerous examples of antisense compounds are illustrated herein and others may be selected from among suitable compounds known in the art. Two or more combined compounds may be used together or sequentially.

Dosing:

The formulation of therapeutic compositions and their subsequent administration (dosing) is believed to be within the skill of those in the art. Dosing is dependent on severity and responsiveness of the disease state to be treated, with die course of treatment lasting from several days to several months, or until a cure is effected or a diminution of die disease state is achieved. Optimal dosing schedules can be calculated from measurements of drug accumulation in the body of the patient. Persons of ordinary skill can easily determine optimum dosages, closing methodologies and repetition rates. Optimum dosages may vary depending on the relative potency of individual oligonucleotides, and can generally be estimated based on EC50s found to be effective in in vitro and in vivo animal models. In general, dosage is from 0.01 μg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily, to once every 20 years.

In embodiments, a patient is treated with a dosage of drug that is at least about 1, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100 mg/kg body weight. Certain injected dosages of antisense oligonucleotides are described, e.g., in U.S. Pat. No. 7,563,884, "Antisense modulation of PTP1B expression," incorporated herein by reference in its entirety.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments.

All documents mentioned herein are incorporated herein by reference. All publications and patent documents cited in this application are incorporated by reference for all purposes to the same extent as if each individual publication or patent document were so individually denoted. By their citation of various references in this document. Applicants do not admit any particular reference is "prior art" to their invention. Embodiments of inventive compositions and methods are illustrated in the following examples.

EXAMPLES

The following non-limiting Examples serve to illustrate selected embodiments of the invention. It will be appreciated that variations in proportions and alternatives in elements of the components shown will be apparent to those skilled in the an and are within the scope of embodiments of the present invention.

Example 1

Design of Antisense Oligonucleotides Specific for a Nucleic Acid Molecule Antisense to a Pancreatic Developmental Gene and/or a Sense Strand of a Pancreatic Developmental Gene Polynucleotide As indicated above the term "oligonucleotide specific for" or "oligonucleotide targets" refers to an oligonucleotide having a sequence (i) capable of forming a stable complex with a portion of the targeted gene, or (ii) capable of forming a stable duplex with a portion of an mRNA transcript of the targeted gene.

Selection of appropriate oligonucleotides is facilitated by using computer programs that automatically align nucleic acid sequences and indicate regions of identity or homology. Such programs are used to compare nucleic acid sequences obtained, for example, by searching databases such as Gen-Bank or by sequencing PCR products. Comparison of nucleic acid sequences from a range of species allows the selection of nucleic acid sequences that display an appropriate degree of identity between species. In the case of genes that have not been sequenced. Southern blots are performed to allow a determination of the degree of identity between genes in target species and other species. By performing Southern blots at varying degrees of stringency, as is well known in the art, it is possible to obtain an approximate measure of identity. These procedures allow the selection of oligonucleotides that exhibit a high degree of complementarity to target nucleic acid sequences in a subject to be controlled and a lower degree of complementarity to corresponding nucleic acid sequences in other species. One skilled in the art will realize that there is considerable latitude in selecting appropriate regions of genes for use in the present invention.

An antisense compound is "specifically hybridizable" when binding of the compound to the target nucleic acid interferes with the normal function of the target nucleic acid to cause a modulation of function and/or activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays The hybridization properties of the oligonucleotides described herein can be determined by one or more in vitro assays as known in the art. For example, the properties of the oligonucleotides described herein can be obtained by determination of binding strength between the target natural antisense and a potential drug molecules using melting curve assay.

The binding strength between the target natural antisense and a potential drug molecule (Molecule) can be estimated using any of the established methods of measuring the strength of intermolecular interactions, for example, a melting curve assay.

Melting curve assay determines the temperature at which a rapid transition from double-stranded to single-stranded conformation occurs for the natural antisense/Molecule complex. This temperature is widely accepted as a reliable measure of the interaction strength between the two molecules.

A melting curve assay can be performed using a cDNA copy of the actual natural antisense RNA molecule or a synthetic DNA or RNA nucleotide corresponding to the binding site of the Molecule. Multiple kits containing all necessary reagents to perform this assay are available (e.g. Applied Biosystems Inc. MeltDoctor kit). These kits include a suitable buffer solution containing one of the double strand DNA (dsDNA) binding dyes (such as ABI HRM dyes, SYBR Green. SYTO, etc.). The properties of the dsDNA dyes are such that they emit almost no fluorescence in free form, but are highly fluorescent when bound to dsDNA.

To perform the assay the cDNA or a corresponding oligonucleotide are mixed with Molecule in concentrations defined by the particular manufacturer's protocols. The mixture is heated to 95° C. to dissociate all pre-formed dsDNA complexes, then slowly cooled to room temperature or other lower temperature defined by the kit manufacturer to allow the DNA molecules to anneal. The newly formed complexes are then slowly heated to 95° C. with simultaneous continuous collection of data on the amount of fluorescence that is produced by the reaction. The fluorescence intensity is inversely proportional to the amounts of dsDNA present in the reaction. The data can be collected using a real time PCR instrument compatible with the kit (e.g. ABI's StepOne Plus Real Time PCR System or LightTyper instrument, Roche Diagnostics, Lewes, UK).

Melting peaks are constructed by plotting the negative derivative of fluorescence with respect to temperature (-d (Fluorescence)/dT) on the y-axis) against temperature (x-axis) using appropriate software (for example LightTyper (Roche) or SDS Dissociation Curve, ABI). The data is analyzed to identify the temperature of the rapid transition from dsDNA complex to single strand molecules. This temperature is called Tm and is directly proportional to the strength of interaction between the two molecules. Typically, Tm will exceed 40° C.

Example 2

Modulation of a Pancreatic Developmental Gene Polynucleotide Treatment of HepG2 Cells with Antisense Oligonucleotides HepG2 cells from ATCC (cat #HB-8065) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% CO2. One day before the experiment the cells were replated at the density of 1.5×105/ml into 6 well plates and incubated at 37° C. and 5% CO2. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with HepG2 cells. A Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs01922995_s1, Hs001651425_s1, and Hs00426216_m1 by Applied Biosystems Inc., Foster City, Calif.). The following PCR cycle was used: 50° C. for 2 min, 95° C. for 10 min, 40 cycles of (95° C. for 15 seconds, 60° C. for 1 min) using Mx4000 thermal cycler (Stratagene). Fold change in gene expression after treatment with antisense oligonucleotides was calculated based on the difference in 18S-normalized dCt values between treated and mock-transfected samples.

Results

Real time PCR results show that the fold change standard deviation in NeuroD1 mRNA after treatment of HepG2 cells with phosphorotioate oligonucleotides introduced using Lipofectamine 2000, as compared to control (FIG. 1).

Figure 3:
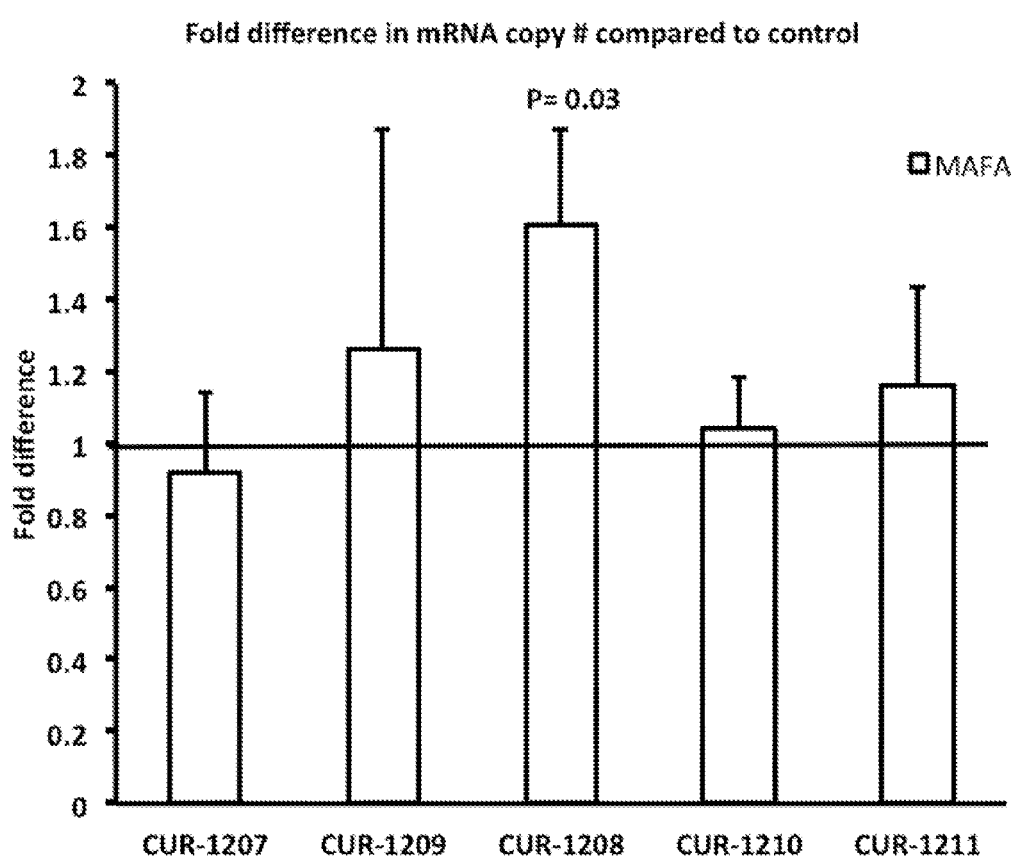
FIG. 3 is a graph of real time PCR results showing the fold change+standard deviation in MAFA mRNA after treatment of HepG2 cells with phosphorothioate oligonucleotides introduced using Lipofectamine 2000, as compared to control. Real time PCR results show that the levels of MAFA mRNA in HepG2 cells are significantly increased 48 h after treatment with one of the oligos designed to MAFA antisense BM127748. Bare denoted as CUR-1207, CUR-1209, CUR-1208, CUR-1210 and CUR-1211 correspond to samples treated with SEQ ID NOS: 32 to 36 respectively.

Real time PCR results show that the levels of MAFA mRNA in HepG2 cells are significantly increased 48 h after treatment with one of the oligos designed to MAFA antisense BM127748 (FIG. 3).

Figure 4:
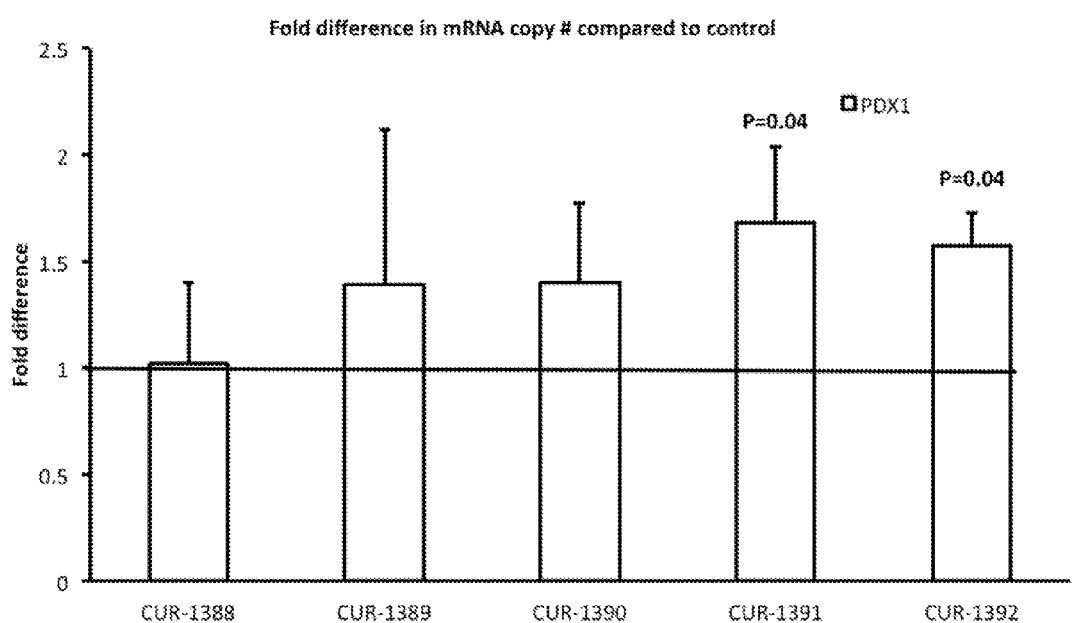
FIG. 4 is a graph of real time PCR results showing the fold change+standard deviation in PDX1 mRNA after treatment of HepG2 cells with phosphorothioate oligonucleotides introduced using Lipofectamine 2000, as compared to control. Real time PCR results show that the levels of PDX1 mRNA are significantly increased in HepG2 cells 48 h after treatment with two of the oligos designed to PDX1 antisense Hs.416201. Bars denoted as CUR-1388, CUR-1389, CUR-1390, CUR-1391 and CUR-1392 correspond to samples treated with SEQ ID NOS: 37 to 41 respectively.

Real time PCR results show that the levels of PDX1 mRNA in HepG2 cells are significantly increased 48 h after treatment with one of the oligos designed to PDX1 antisense Hs.416201 (FIG. 4).

Treatment of 518A2 Cells with Antisense Oligonucleotides:

518A2 cells obtained from Albert Einstein-Montefiore Cancer Center, NY were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CI)) at 37° C. and 5% CO2. One day before the experiment die cells were replated at the density of 1.5×105/ml into 6 well plates and incubated at 37° C. and 5% CO2. On the day of the experiment the media in the 6 well plates was changed to fresh growth media. All antisense oligonucleotides were diluted to die concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with 518A2 cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813 as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs01023298_m1 by Applied Biosystems Inc., Foster City Calif.). The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems). Fold change in gene expression after treatment with antisense oligonucleotides was calculated based on the difference in 18S-normalized dCt values between treated and mock-transfected samples.

Figure 2:
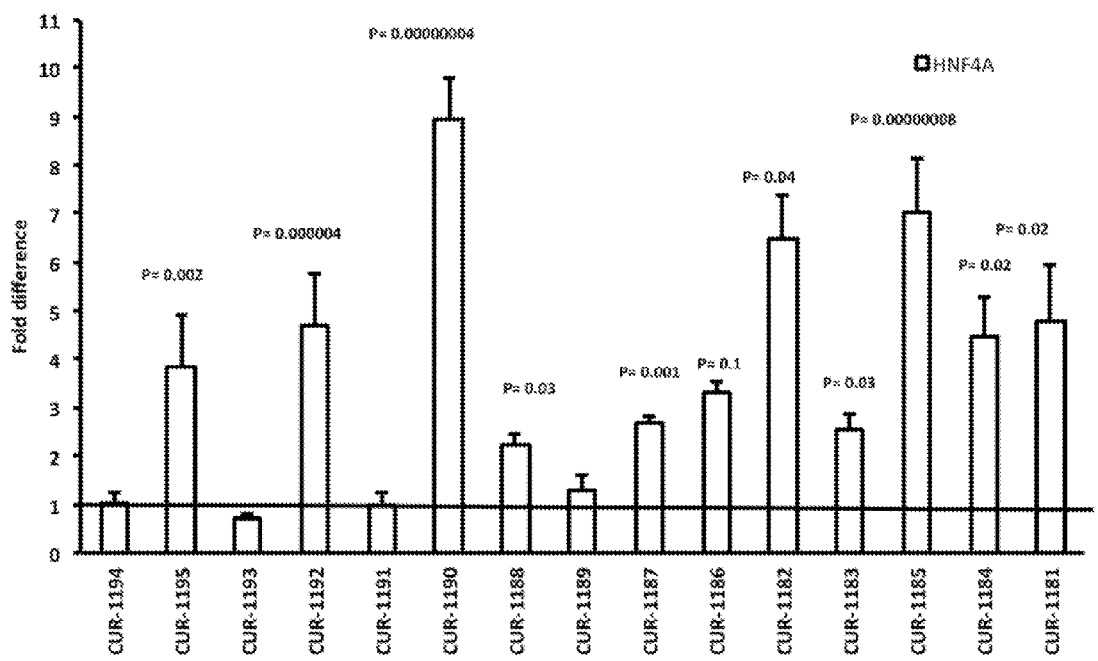
FIG. 2 is a graph of real time PCR results showing the fold change+standard deviation in HNF4A mRNA after treatment of 518A2 cells with phosphorothioate oligonucleotides introduced using Lipofectamine 2000, as compared to control. Bars denoted as CUR-1194, CUR-1195, CUR-1193, CUR-1192, CUR-1191, CUR-1190, CUR-1188, CUR-1189, CUR-1187, CUR-1186, CUR-1182. CUR-1183, CUR-1185, CUR-1184, CUR-1181 correspond to samples treated with SEQ ID NOS: 17 to 31 respectively.

Results:

Real time PCR results show that the levels of HNF4A mRNA in 518A2 cells are significantly increased 48 h after treatment with oligos to HNF4A antisense transcripts BX099913, BC071794 and AF143870 (FIG. 2).

Treatment of MCF-7 Cells with Antisense Oligonucleotides:

MCF-7 cells from ATCC (cat #HTB-22) were grown in growth media (MEM/EBSS (Hyclone cat #SH30024, or Mediatech cat #MT-10-010-CV)+10% FBS (Mediatech cat #MT35-011-CV)+penicillin/streptomycin (Mediatech cat #MT30-002-CD) at 37° C. and 5% $CO_2$. One day before the experiment the cells were replated at the density of $1.5 \times 10^5$ ml into 6 well plates and incubated at 37° C. and 5% CO2. On the day of the experiment the media in the 6 well plates was changed to fresh growth media. All antisense oligonucleotides were diluted to the concentration of 20 μM. Two μl of this solution was incubated with 400 μl of Opti-MEM media (Gibco cat #31985-070) and 4 μl of Lipofectamine 2000 (Invitrogen cat #11668019) at room temperature for 20 min and applied to each well of the 6 well plates with MCF-7 cells. Similar mixture including 2 μl of water instead of the oligonucleotide solution was used for the mock-transfected controls. After 3-18 h of incubation at 37° C. and 5% CO2 the media was changed to fresh growth media. 48 h after addition of antisense oligonucleotides the media was removed and RNA was extracted from the cells using SV Total RNA Isolation System from Promega (cat #Z3105) or RNeasy Total RNA Isolation kit from Qiagen (cat #74181) following the manufacturers' instructions. 600 ng of RNA was added to the reverse transcription reaction performed using Verso cDNA kit from Thermo Scientific (cat #AB1453B) or High Capacity cDNA Reverse Transcription Kit (cat #4368813) as described in the manufacturer's protocol. The cDNA from this reverse transcription reaction was used to monitor gene expression by real time PCR using ABI Taqman Gene Expression Mix (cat #4369510) and primers/probes designed by ABI (Applied Biosystems Taqman Gene Expression Assay: Hs00232355_m1. The following PCR cycle was used: 50° C. for 2 min, 95° C. for 10 min, 40 cycles of (95° C. for 15 seconds, 60° C. for 1 min) using StepOne Plus Real Time PCR Machine (Applied Biosystems).

Fold change in gene expression after treatment with antisense oligonucleotides was calculated based on the difference in 18S-normalized dCt values between treated and mock-transfected samples.

Results:

Real time PCR results show that the levels of the NKX6-1 mRNA in MCF-7 cells are significantly increased 48 h after treatment with the oligos designed to NKX6-1 antisense torsnaby.aApr07-unspliced (FIG. 5).

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The Abstract of the disclosure will allow the reader to quickly ascertain the nature of the technical disclosure. It is submitted with the understanding that it will not be used to interpret or limit the scope or meaning of the following claims.

| CUR NO | SEQ ID NO: | SEQUENCE |
|---|---|---|
| CUR-1373 | SEQ ID NO: 13 | T*C*C*T*C*T*C*T*C*C*A*A*C*C*A*C*T |
| CUR-1374 | SEQ ID NO: 14 | T*G*T*C*T*C*G*G*C*T*C*T*C*C*A*C*T*C*C*T |
| CUR-1375 | SEQ ID NO: 15 | C*A*T*T*C*C*T*T*C*C*A*C*A*A*T*T*C*G*C*T |
| CUR-1376 | SEQ ID NO: 16 | G*T*T*C*C*T*C*C*C*G*T*G*C*C*T*T*T*A*G |
| CUR-1194 | SEQ ID NO: 17 | A*C*C*T*A*T*A*G*T*A*C*A*C*G*C*C*C*A*G*C*A |
| CUR-1195 | SEQ ID NO: 18 | G*C*T*T*C*T*G*C*C*C*A*G*G*T*G*T*G*A*C*A |
| CUR-1193 | SEQ ID NO: 19 | C*A*G*C*A*A*G*T*G*T*T*C*A*G*A*T*C*C*A |
| CUR-1192 | SEQ ID NO: 20 | A*G*T*G*T*C*A*G*A*T*C*C*C*A*G*C*T*C*C*A*G |
| CUR-1191 | SEQ ID NO: 21 | G*G*A*G*T*T*T*G*G*T*T*G*G*G |
| CUR-1190 | SEQ ID NO: 22 | G*T*G*T*C*A*G*A*T*C*C*C*A*G*C*T*C*C*A*G |
| CUR-1188 | SEQ ID NO: 23 | C*T*C*G*T*T*A*C*C*T*C*T*T*G*T*C*C*T*G*G |
| CUR-1189 | SEQ ID NO: 24 | A*G*T*C*G*G*G*A*G*G*G*G*C*T*T*G*G*G*T*T*A |
| CUR-1187 | SEQ ID NO: 25 | C*C*C*T*G*C*T*T*C*C*T*T*C*T*G*T*G*T*C*T |
| CUR-1186 | SEQ ID NO: 26 | G*C*C*A*C*C*C*T*G*C*T*T*C*C*T*T*C*T*G*T |
| CUR-1182 | SEQ ID NO: 27 | T*C*C*T*G*C*T*T*C*T*C*G*G*C*T*C*T*C*A |
| CUR-1183 | SEQ ID NO: 28 | C*C*T*C*C*A*T*G*T*C*C*T*G*C*C*C*T*C*A*A |
| CUR-1185 | SEQ ID NO: 29 | T*C*C*G*T*C*T*C*C*T*C*C*A*T*T*A*G*T*C*C*A |
| CUR-1184 | SEQ ID NO: 30 | T*C*C*G*T*C*T*C*C*T*C*C*A*T*T*A*G*T*C*C |
| CUR-1181 | SEQ ID NO: 31 | G*T*C*C*G*T*C*T*C*C*T*C*C*A*T*T*A*G*T*C*C |
| CUR-1207 | SEQ ID NO: 32 | C*T*A*C*C*A*A*G*C*A*T*C*A*C*C*T*C*A*A*C*C*C |
| CUR-1209 | SEQ ID NO: 33 | A*G*T*T*C*G*A*G*G*T*G*A*A*G*G*A*A*G*G*A*G*C |
| CUR-1208 | SEQ ID NO: 34 | C*G*C*T*G*G*A*G*G*A*T*C*T*G*T*A*C*T*G*G*A |
| CUR-1210 | SEQ ID NO: 35 | C*C*T*G*A*T*G*A*A*G*T*T*C*G*A*G*G*T*G*A |
| CUR-1211 | SEQ ID NO: 36 | G*T*A*C*G*T*C*A*A*A*C*G*A*C*T*T*C*G*A*C*C*T |
| CUR-1388 | SEQ ID NO: 37 | G*C*A*A*T*T*G*A*A*G*C*T*G*T*C*T*C*C*C |
| CUR-1389 | SEQ ID NO: 38 | C*G*G*C*A*G*A*G*A*A*C*A*G*A*A*G*G*T*C |
| CUR-1390 | SEQ ID NO: 39 | T*T*T*C*A*G*G*A*G*A*T*G*G*G*C*G*C*T*C |
| CUR-1391 | SEQ ID NO: 40 | G*G*A*G*A*G*C*A*A*T*C*T*G*A*G*A*A*G*C*G*A |
| CUR-1392 | SEQ ID NO: 41 | G*C*C*T*C*T*C*A*A*C*G*T*C*A*G*A*G*C*C*T |
| CUR-1501 | SEQ ID NO: 42 | T*C*T*C*A*G*T*C*T*C*A*A*T*C*T*C*T*C*C*C |
| CUR-1502 | SEQ ID NO: 43 | G*T*T*A*C*A*C*G*T*C*C*A*C*T*C*C*C*A*A*G*G |
| CUR-1503 | SEQ ID NO: 44 | G*C*T*A*T*G*C*C*T*G*C*C*A*C*C*A*T*C*C*T |
| CUR-1504 | SEQ ID NO: 45 | T*T*t*C*C*T*C*C*C*A*AT*T*C*C*T*A*C*C*T |

What is claimed is:

1. A method of upregulating a function of and/or the expression of a Pancreatic Developmental gene polynucleotide in patient cells or tissues in vivo or in vitro comprising: contacting said cells or tissues with at least one single stranded antisense oligonucleotide 19 to 21 nucleotides in length wherein said at least one oligonucleotide has at least 90% sequence identity to a reverse complement of a polynucleotide comprising 19 to 21 consecutive nucleotides within the natural antisense polynucleotide selected from the group consisting of nucleotides 1 to 1235 of SEQ ID SEQ ID NO: 6, 1 to 17,964 of SEQ ID NO: 7, 1 to 1 to 50,003 of SEQ ID SEQ ID NO: 8, 1 to 486 of SEQ ID NO: 9, 1 to 494 of SEQ ID NO: 10, 1 to 1992 of SEQ ID NO: 11, or 1 to 1767 of SEQ ID NO: 12 and wherein said antisense oligonucleotide specifically targets said natural antisense polynucleotide; thereby upregulating a function of and/or the expression of the Pancreatic Developmental gene polynucleotide in patient cells or tissues in vivo or in vitro.

2. A method of upregulating a function of and/or the expression of a Pancreatic Developmental gene polynucleotide selected from the group comprising SEQ ID NOS: 1-5 in patient cells or tissues in vivo or in vitro comprising: contacting said cells or tissues with at least one single stranded antisense oligonucleotide 19 to 21 nucleotides in length wherein said at least one antisense oligonucleotide has at least 90% sequence identity to a corresponding 19 to 21 nucleotide region within a reverse complement of a natural antisense polynucleotide of a Pancreatic Developmental gene polynucleotide wherein said antisense oligonucleotide specifically targets said natural antisense polynucleotide; thereby upregulating a function of and/or the expression of the Pancreatic Developmental gene polynucleotide in patient cells or tissues in vivo or in vitro.

3. A method of upregulating a function of and/or the expression of a Pancreatic Developmental gene polynucleotide in patient cells or tissues in vivo or in vitro comprising: contacting said cells or tissues with at least one modified single stranded antisense oligonucleotide of 19 to 21 nucleotides in length that specifically targets a complementary region of a natural antisense polynucleotide the Pancreatic Developmental gene; thereby upregulating a function of and/or the expression of the Pancreatic Developmental gene in patient cells or tissues in vivo or in vitro.

4. The method of claim 3, wherein a function of and/or the expression of Pancreatic Developmental gene is increased in vitro with respect to a mock-transfected control.

5. The method of claim 3, wherein the at least one antisense oligonucleotide targets a natural antisense polynucleotide selected from the group consisting of SEQ ID NOS: 6-12.

6. The method of claim 3, wherein the at least one antisense oligonucleotide targets a natural antisense polynucleotide antisense to non-coding nucleic acid sequences of a Pancreatic Developmental gene polynucleotide.

7. The method of claim 3, wherein the at least one antisense oligonucleotide targets a natural antisense polynucleotide having overlapping and/or non-overlapping sequences with a Pancreatic Developmental gene polynucleotide.

8. The method of claim 3, wherein at least one antisense oligonucleotide comprises one or more modifications selected from: at least one modified sugar moiety, at least one modified internucleoside linkage, at least one modified nucleotide, and combinations thereof.

9. The method of claim 8, wherein the one or more modifications comprise at least one modified sugar moiety selected from a 2'-O-methoxyethyl modified sugar moiety, a 2'-methoxy modified sugar moiety, a 2'-O-alkyl modified sugar moiety, a bicyclic sugar moiety, and combinations thereof.

10. The method of claim 8, wherein the one or more modifications comprise at least one modified internucleoside linkage selected from: a phosphorothionate, alkylphosphonate, phosphorodithioate, alkylphosphonothioate, phosphoramidate, carbamate, carbonate, phosphate triester, acetamidate, carboxymethyl ester, and combinations thereof.

11. The method of claim 8, wherein the one or more modifications comprise at least modified nucleotide selected from: a peptide nucleic acid (PNA), a locked nucleic acid (LNA), an arabino-nucleic acid (FANA), and combinations thereof.

12. The method of claim 1, wherein the at least one oligonucleotide comprises at least one oligonucleotide sequences set forth as SEQ ID NOS: 13 to 45.

13. A method of upregulating a function of and/or the expression of a Pancreatic Developmental gene in mammalian cells or tissues in vivo or in vitro comprising: contacting said cells or tissues with at least one short interfering RNA (siRNA) oligonucleotide 19 to 21 nucleotides in length, said at least one siRNA oligonucleotide being specific for a natural antisense polynucleotide of a Pancreatic Developmental gene, wherein said at least one siRNA oligonucleotide has at least 90% sequence complementarity to a sequence of at least about nineteen consecutive nucleic acids of the natural antisense polynucleotide; and, upregulating a function of and/or the expression of a Pancreatic Developmental gene in mammalian cells or tissues in vivo or in vitro.

14. The method of claim 13, wherein said oligonucleotide has sequence complementarity to a sequence of at least about nineteen consecutive nucleic acids of the natural antisense polynucleotide of the Pancreatic Developmental gene polynucleotide.

15. A method of upregulating a function of and/or the expression of a Pancreatic Developmental gene in mammalian cells or tissues in vitro comprising:
   contacting said cells or tissues with at least one single stranded modified antisense oligonucleotide of about 19 to 21 nucleotides in length specific for a natural antisense polynucleotide of a Pancreatic Developmental gene wherein said at least one antisense oligonucleotide has at least 90% sequence identity to a 19 to 21 consecutive nucleotide region of the group consisting of SEQ ID NOS: 1 to 5 or polynucleotides transcribed from the Pancreatic Developmental gene; and, upregulating the function and/or expression of the Pancreatic Developmental gene in mammalian cells or tissues in vitro.

* * * * *

SEQUENCE LISTING

```
<160> NUMBER OF SEQ ID NOS: 45

<210> SEQ ID NO 1
<211> LENGTH: 2641
<212> TYPE: DNA
<213> ORGANISM: Homo sapiens
<300> PUBLICATION INFORMATION:
<308> DATABASE ACCESSION NUMBER: NM_002500
<309> DATABASE ENTRY DATE: 2010-12-26
<313> RELEVANT RESIDUES IN SEQ ID NO: (1)..(2641)

<400> SEQUENCE: 1
gagaacgggg agcgcacagc ctggacgcgt gcgcaggcgt caggcgcata gacctgctag     60
cccctcagct agcggccccg cccgcgctta gcatcactaa ctgggctata taacctgagc    120
gcccgcgcgg ccacgacacg aggaattcgc ccacgcagga ggcgcggcgt ccggaggccc    180
cagggttatg agactatcac tgctcaggac ctactaacaa caaaggaaat cgaaacatga    240
ccaaatcgta cagcgagagt gggctgatgg gcgagcctca gccccaaggt cctccaagct    300
ggacagacga gtgtctcagt tctcaggacg aggagcacga ggcagacaag aaggaggacg    360
acctcgaagc catgaacgca gaggaggact cactgaggaa cggggagag gaggaggacg    420 aagatgagga cctggaagag gaggaagaag aggaagagga ggatgacgat caaaagccca    480
agagacgcgg ccccaaaaag aagaagatga ctaaggctcg cctggagcgt tttaaattga    540
gacgcatgaa ggctaacgcc cgggagcgga accgcatgca cggactgaac gcggcgctag    600
acaacctgcg caaggtggtg ccttgctatt ctaagacgca gaagctgtcc aaaatcgaga    660
ctctgcgctt ggccaagaac tacatctggg ctctgtcgga gatcctgcgc tcaggcaaaa    720
gcccagacct ggtctccttc gttcagacgc tttgcaaggg cttatcccaa cccaccacca    780
```

```
acctggttgc gggctgcctg caactcaatc ctcggacttt tctgcctgag cagaaccagg      840
acatgccccc ccacctgccg acggccagcg cttccttccc tgtacacccc tactcctacc      900
agtcgcctgg gctgcccagt ccgccttacg gtaccatgga cagctcccat gtcttccacg      960
ttaagcctcc gccgcacgcc tacagcgcag cgctggagcc cttctttgaa agccctctga     1020
ctgattgcac cagcccttcc tttgatggac ccctcagccc gccgtcagc atcaatggca      1080
acttctcttt caaacacgaa ccgtccgccg agtttgagaa aaattatgcc tttaccatgc     1140
actatcctgc agcgacactg gcaggggccc aaagccacgg atcaatcttc tcaggcaccg     1200
ctgcccctcg ctgcgagatc cccatagaca atattatgtc cttcgatagc cattcacatc     1260
atgagcgagt catgagtgcc cagctcaatg ccatatttca tgattagagg cacgccagtt     1320
tcaccatttc cggaaacga acccactgtg cttacagtga ctgtcgtgtt tacaaaaggc     1380
agccctttgg gtactactgc tgcaaagtgc aaatactcca agcttcaagt gatatatgta     1440
tttattgtca ttactgcctt tggaagaaac aggggatcaa agttcctgtt caccttatgt     1500
attatttct atagctcttc tatttaaaaa ataaaaaaat acagtaaagt ttaaaaaata      1560
caccacgaat ttggtgtggc tgtattcaga tcgtattaat tatctgatcg ggataacaaa     1620
atcacaagca ataattagga tctatgcaat tttaaacta gtaatgggcc aattaaaata      1680
tatataaata tatattttc aaccagcatt ttactacttg ttacctttcc catgctgaat      1740
tattttgttg tgattttgta cagaattttt aatgactttt tataatgtgg atttcctatt    1800
ttaaaaccat gcagcttcat caatttttat acatatcaga aaagtagaat tatatctaat    1860
ttatacaaaa taatttaact aatttaaacc agcagaaaag tgcttagaaa gttattgtgt    1920
tgccttagca cttcttttcct ctccaattgt aaaaaaaaaa aaaaaaaaaa aaaaaaaaa    1980
aaaattgcac aatttgagca attcatttca ctttaaagtc tttccgtctc cctaaaataa    2040
aaaccagaat cataatttc aagagaagaa aaaattaaga gatacattcc ctatcaaaac    2100
atatcaattc aacacattac ttgcacaagc ttgtatatac atattataaa taatgccaa    2160
cataccttc tttaaatcaa aagctgcttg actatcacat acaatttgca ctgttacttt     2220
ttagtcttt actcctttgc attccatgat tttacagaga atctgaagct attgatgttt    2280
ccagaaaata taaatgcatg attttataca tagtcacaaa aatggtggtt tgtcatatat   2340
tcatgtaata aatctgagcc taaatctaat caggttgtta atgttgggat ttatatctat    2400
agtagtcaat tagtacagta gcttaaataa attcaaacca tttaattcat aattagaaca    2460
atagctattg catgtaaaat gcagtccaga ataagtgctg tttgagatgt gatgctggta    2520
ccactggaat cgatctgtac tgtaattttg tttgtaatcc tgtatattat ggtgtaatgc    2580
acaatttaga aaacattcat ccagttgcaa taaatagta ttgaaagtga aaaaaaaaa      2640
a                                                                    2641
```

<210> SEQ ID NO 2
<211> LENGTH: 3239
<212> TYPE: DNA
<213> ORGANISM: Homo sapiens
<300> PUBLICATION INFORMATION:
<308> DATABASE ACCESSION NUMBER: NM_000457.3
<309> DATABASE ENTRY DATE: 2010-12-20
<313> RELEVANT RESIDUES IN SEQ ID NO: (1)..(3239)

<400> SEQUENCE: 2

```
gggaggaggc agtgggaggg cggagggcgg gggccttcgg ggtgggcgcc cagggtaggg       60
```

| | |
|---|---|
| caggtggccg cggcgtggag gcagggagaa tgcgactctc caaaaccctc gtcgacatgg | 120 |
| acatggccga ctacagtgct gcactggacc cagcctacac caccctggaa tttgagaatg | 180 |
| tgcaggtgtt gacgatgggc aatgacacgt ccccatcaga aggcaccaac ctcaacgcgc | 240 |
| ccaacagcct gggtgtcagc gccctgtgtg ccatctgcgg ggaccgggcc acgggcaaac | 300 |
| actacggtgc ctcgagctgt gacggctgca agggcttctt ccggaggagc gtgcggaaga | 360 |
| accacatgta ctcctgcaga tttagccggc agtgcgtggt ggacaaagac aagaggaacc | 420 |
| agtgccgcta ctgcaggctc aagaaatgct tccgggctgg catgaagaag aagccgtcc | 480 |
| agaatgagcg ggaccggatc agcactcgaa ggtcaagcta tgaggacagc agcctgccct | 540 |
| ccatcaatgc gctcctgcag gcggaggtcc tgtcccgaca gatcacctcc cccgtctccg | 600 |
| ggatcaacgg cgacattcgg gcgaagaaga ttgccagcat cgcagatgtg tgtgagtcca | 660 |
| tgaaggagca gctgctggtt ctcgttgagt gggccaagta catcccagct ttctgcgagc | 720 |
| tcccctgga cgaccaggtg gccctgctca gagcccatgc tggcgagcac ctgctgctcg | 780 |
| gagccaccaa gagatccatg gtgttcaagg acgtgctgct cctaggcaat gactacattg | 840 |
| tccctcggca ctgcccggag ctggcggaga tgagccgggt gtccatacgc atccttgacg | 900 |
| agctggtgct gcccttccag gagctgcaga tcgatgacaa tgagtatgcc tacctcaaag | 960 |
| ccatcatctt ctttgaccca gatgccaagg ggctgagcga tccagggaag atcaagcggc | 1020 |
| tgcgttccca ggtgcaggtg agcttggagg actacatcaa cgaccgccag tatgactcgc | 1080 |
| gtggccgctt tggagagctg ctgctgctgc tgcccacctt gcagagcatc acctggcaga | 1140 |
| tgatcgagca gatccagttc atcaagctct tcggcatggc caagattgac aacctgttgc | 1200 |
| aggagatgct gctgggaggg tcccccagcg atgcaccccca tgcccaccac cccctgcacc | 1260 |
| ctcacctgat gcaggaacat atgggaacca acgtcatcgt tgccaacaca atgcccactc | 1320 |
| acctcagcaa cggacagatg tgtgagtggc ccgacccag gggacaggca gccaccctg | 1380 |
| agaccccaca gccctcaccg ccaggtggct cagggtctga gccctataag ctcctgccgg | 1440 |
| gagccgtcgc cacaatcgtc aagcccctct ctgccatccc ccagccgacc atcaccaagc | 1500 |
| aggaagttat ctagcaagcc gctggggctt gggggctcca ctggctcccc ccagcccct | 1560 |
| aagagagcac ctggtgatca cgtggtcacg gcaaaggaag acgtgatgcc aggaccagtc | 1620 |
| ccagagcagg aatgggaagg atgaagggcc cgagaacatg gcctaagggc cacatcccac | 1680 |
| tgccaccctt gacgccctgc tctggataac aagactttga cttggggaga cctctactgc | 1740 |
| cttgacaact ttttctcatg ttgaagccac tgccttcacc ttcaccttca tccatgtcca | 1800 |
| accccgact tcatcccaaa ggacagccgc ctggagatga cttgaggcct tacttaaacc | 1860 |
| cagctccctt cttccctagc ctggtgcttc tcctctccta gccctgtca tggtgtccag | 1920 |
| acagagccct gtgaggctgg gtccaattgt ggcacttggg gcaccttgct cctccttctg | 1980 |
| ctgctgcccc cacctctgct gcctcccctct gctgtcacct tgctcagcca tcccgtcttc | 2040 |
| tccaacacca cctctccaga ggccaaggag gccttggaaa cgattccccc agtcattctg | 2100 |
| ggaacatgtt gtaagcactg actgggacca ggcaccaggc agggtctaga aggctgtggt | 2160 |
| gagggaagac gcctttctcc tccaacccaa cctcatcctc cttcttcagg acttgggtg | 2220 |
| ggtacttggg tgaggatccc tgaaggcctt caacccgaga aaacaaaccc aggttggcga | 2280 |
| ctgcaacagg aacttggagt ggagaggaaa agcatcagaa agaggcagac catccaccag | 2340 |
| gccttttgaga aagggtagaa ttctggctgg tagagcaggt gagatgggac attccaaaga | 2400 |
| acagcctgag ccaaggccta gtggtagtaa gaatctagca agaattgagg aagaatggtg | 2460 |

```
tgggagaggg atgatgaaga gagagagggc ctgctggaga gcatagggtc tggaacacca    2520
ggctgaggtc ctgatcagct tcaaggagta tgcaggagc tgggcttcca gaaaatgaac    2580
acagcagttc tgcagaggac gggaggctgg aagctgggag gtcaggtggg gtggatgata    2640
taatgcgggt gagagtaatg aggcttgggg ctggagagga caagatgggt aaaccctcac    2700
atcagagtga catccaggag gaataagctc ccagggcctg tctcaagctc ttccttactc    2760
ccaggcactg tcttaaggca tctgacatgc atcatctcat ttaatcctcc cttcctccct    2820
attaacctag agattgtttt tgttttttat tctcctcctc cctccccgcc ctcacccgcc    2880
ccactccctc ctaacctaga gattgttaca gaagctgaaa ttgcgttcta agaggtgaag    2940 tgatttttt tctgaaactc acacaactag gaagtggctg agtcaggact tgaacccagg    3000
tctccctgga tcagaacagg agctcttaac tacagtggct gaatagcttc tccaaaggct    3060
ccctgtgttc tcaccgtgat caagttgagg ggcttccggc tcccttctac agcctcagaa    3120
accagactcg ttcttctggg aaccctgccc actcccagga ccaagattgg cctgaggctg    3180
cactaaaatt cacttagggt cgagcatcct gtttgctgat aaatattaag gagaattca    3239
```

```
<210> SEQ ID NO 3
<211> LENGTH: 1062
<212> TYPE: DNA
<213> ORGANISM: Homo sapiens
<300> PUBLICATION INFORMATION:
<308> DATABASE ACCESSION NUMBER: NM_201589
<309> DATABASE ENTRY DATE: 2010-12-27
<313> RELEVANT RESIDUES IN SEQ ID NO: (1)..(1062)

<400> SEQUENCE: 3
```

```
atggccgcgg agctggcgat gggcgccgag ctgcccagca gccgctggcc catcgagtac      60
gtcaacgact tcgacctgat gaagttcgag gtgaagaagg agcctcccga ggccgagcgc     120
ttctgccacc gctgccgcc aggctcgctg tcctcgacgc cgctcagcac gccctgctcc     180
tccgtgccct cctcgcccag cttctgcgcg cccagcccgg gcaccggcgg cggcggcggc     240
gcggggggcg gcggcggctc gtctcaggcc ggggcgccc ccgggccgcc gagcggggggc     300 cccggcgccg tcggggcac ctcggggaag ccggcgctgg aggatctgta ctggatgagc     360
ggctaccagc atcacctcaa cccccgaggcg ctcaacctga cgcccgagga cgcggtggag     420
gcgctcatcg gcagcggcca ccacggcgcg caccacggcg cgcaccaccc ggcggccgcc     480
gcagcctacg aggctttccg cggcccgggc ttcgcgggcg gcggcggagc ggacgacatg     540
ggcgccggcc accaccacgg cgcgcaccac gccgcccacc atcaccacgc cgcccaccac     600
caccaccacc accaccacca ccatggcggc gcgggacacg gcgtggcgc gggccaccac     660 gtgcgcctgg aggagcgctt ctccgacgac cagctggtgt ccatgtcggt gcgcgagctg     720
aaccggcagc tccgcggctt cagcaaggag gaggtcatcc ggctcaagca gaagcggcgc     780
acgctcaaga accgcggcta cgcgcagtcc tgccgcttca gcggggtgca gcagcggcac     840
attctggaga gcgagaagtg ccaactccag agccaggtgg agcagctgaa gctggaggtg     900
gggcgcctgg ccaaagagcg ggacctgtac aaggagaaat acgagaagct ggcggggccgg     960 ggcggccccg ggagcgcggg cggggccggt ttccgcgggg agcttcgcc gccgcaggcc    1020 ggtcccggcg gggccaaggg cacggccgac ttcttcctgt ag                       1062
```

```
<210> SEQ ID NO 4
<211> LENGTH: 2573
<212> TYPE: DNA
```

-continued

<213> ORGANISM: Homo sapiens
<300> PUBLICATION INFORMATION:
<308> DATABASE ACCESSION NUMBER: NM_000209
<309> DATABASE ENTRY DATE: 2010-12-26
<313> RELEVANT RESIDUES IN SEQ ID NO: (1)..(2573)

<400> SEQUENCE: 4

| | | | | | |
|---|---|---|---|---|---|
| gggtggcgcc | gggagtggga | acgccacaca | gtgccaaatc | cccggctcca | gctcccgact | 60 |
| cccggctccc | ggctcccggc | tcccggtgcc | caatcccggg | ccgcagccat | gaacggcgag | 120 |
| gagcagtact | acgcggccac | gcagctttac | aaggacccat | gcgcgttcca | gcgaggcccg | 180 |
| gcgccggagt | tcagcgccag | ccccctgcg | tgcctgtaca | tgggccgcca | gccccgccg | 240 |
| ccgccgccgc | acccgttccc | tggcgccctg | ggcgcgctgg | agcagggcag | cccccggac | 300 |
| atctccccgt | acgaggtgcc | cccctcgcc | gacgaccccg | cggtggcgca | ccttcaccac | 360 |
| cacctcccgg | ctcagctcgc | gctcccccac | ccgcccgccg | ggcccttccc | ggagggagcc | 420 |
| gagccgggcg | tcctggagga | gcccaaccgc | gtccagctgc | ctttcccatg | gatgaagtct | 480 |
| accaaagctc | acgcgtggaa | aggccagtgg | gcaggcggcg | cctacgctgc | ggagccggag | 540 |
| gagaacaagc | ggacgcgcac | ggcctacacg | cgcgcacagc | tgctagagct | ggagaaggag | 600 |
| ttcctattca | acaagtacat | ctcacggccg | cgccgggtgg | agctggctgt | catgttgaac | 660 |
| ttgaccgaga | gacacatcaa | gatctggttc | caaaaccgcc | gcatgaagtg | gaaaaaggag | 720 |
| gaggacaaga | agcgcggcgg | cgggacagct | gtcgggggtg | gcggggtcgc | ggagcctgag | 780 |
| caggactgcg | ccgtgacctc | cggcgaggag | cttctggcgc | tgccgccgcc | gccgcccccc | 840 |
| ggaggtgctg | tgccgcccgc | tgcccccgtt | gccgccgag | agggccgcct | gccgcctggc | 900 |
| cttagcgcgt | cgccacagcc | ctccagcgtc | gcgcctcggc | ggccgcagga | accacgatga | 960 |
| gaggcaggag | ctgctcctgg | ctgagggct | caaccactc | gccgaggagg | agcagagggc | 1020 |
| ctaggaggac | cccgggcgtg | gaccacccgc | cctggcagtt | gaatggggcg | gcaattgcgg | 1080 |
| ggcccacctt | agaccgaagg | ggaaaacccg | ctctctcagg | cgcatgtgcc | agttggggcc | 1140 |
| ccgcgggtag | atgccggcag | gccttccgga | agaaaaagag | ccattggttt | ttgtagtatt | 1200 |
| ggggcctct | tttagtgata | ctggattggc | gttgtttgtg | gctgttgcgc | acatccctgc | 1260 |
| cctcctacag | cactccacct | tgggacctgt | ttagagaagc | cggctcttca | aagacaatgg | 1320 |
| aaactgtacc | atacacattg | gaaggctccc | taacacacac | agcggggaag | ctgggccgag | 1380 |
| taccttaatc | tgccataaag | ccattcttac | tcgggcgacc | cctttaagtt | tagaaataat | 1440 |
| tgaaaggaaa | tgtttgagtt | ttcaaagatc | ccgtgaaatt | gatgccagtg | gaatacagtg | 1500 |
| agtcctcctc | ttcctcctcc | tcctcttccc | cctcccttc | ctcctcctcc | tcttcttttc | 1560 |
| cctcctcttc | ctcttcctcc | tgctctcctt | tcctccccct | cctctttcc | ctcctcttcc | 1620 |
| tcttcctcct | gctctccttt | cctccccctc | ctctttctcc | tcctcctcct | cttcttcccc | 1680 |
| ctcctctccc | tcctcctctt | cttccccctc | ctctccctcc | tcctcttctt | ctccctcctc | 1740 |
| ttcctcttcc | tcctcttcca | cgtgctctcc | tttcctcccc | ctcctcttgc | tccccttctt | 1800 |
| ccccgtcctc | ttcctcctcc | tcctcttctt | ctccctcctc | ttcctcctcc | tctttcttcc | 1860 |
| tgacctcttt | ctttctcctc | ctcctccttc | tacctcccct | tctcatccct | cctcttcctc | 1920 |
| ttctctagct | gcacacttca | ctactgcaca | tcttataact | tgcacccctt | tcttctgagg | 1980 |
| aagagaacat | cttgcaaggc | agggcgagca | gcggcagggc | tggcttagga | gcagtgcaag | 2040 |
| agtccctgtg | ctccagttcc | acactgctgg | caggaaggc | aagggggac | gggcctggat | 2100 |
| ctgggggtga | gggagaaaga | tggaccctg | ggtgaccact | aaaccaaaga | tattcggaac | 2160 |

```
tttctattta ggatgtggac gtaattcctg ttccgaggta gaggctgtgc tgaagacaag    2220
cacagtggcc tggtgcgcct tggaaaccaa caactattca cgagccagta tgaccttcac    2280
atctttagaa attatgaaaa cgtatgtgat tggagggttt ggaaaaccag ttatcttatt    2340
taacatttta aaaattacct aacagttatt tacaaacagg tctgtgcatc ccaggtctgt    2400
cttcttttca aggtctgggc cttgtgctcg ggttatgttt gtgggaaatg cttaataaat    2460
actgataata tgggaagaga tgaaaactga ttctcctcac tttgtttcaa acctttctgg    2520
cagtgggatg attcgaattc acttttaaaa ttaaattagc gtgttttgtt ttg          2573
```

<210> SEQ ID NO 5
<211> LENGTH: 1116
<212> TYPE: DNA
<213> ORGANISM: Homo sapiens
<300> PUBLICATION INFORMATION:
<308> DATABASE ACCESSION NUMBER: NM_006168
<309> DATABASE ENTRY DATE: 2010-12-26
<313> RELEVANT RESIDUES IN SEQ ID NO: (1)..(1116)

<400> SEQUENCE: 5

```
cgtgggatgt tagcggtggg ggcaatggag ggcacccggc agagcgcatt cctgctcagc      60
agccctcccc tggccgccct gcacagcatg gccgagatga agacccgct gtaccctgcc      120 gcgtatcccc cgctgcctgc cggcccccccc tcctcctcgt cctcgtcgtc gtcctcctcg    180
tcgccctccc cgcctctggg cacccacaac ccaggcggcc tgaagccccc ggccacgggg    240
gggctctcat ccctcggcag ccccccgcag cagctctcgg ccgccacccc acacggcatc    300
aacgatatcc tgagccggcc ctccatgccc gtggcctcgg gggccgccct gccctccgcc    360
tcgccctccg gttcctcctc ctcctcttcc tcgtccgcct ctgcctcctc cgcctctgcc    420
gccgccgcgg ctgctgccgc ggccgcagcc gccgcctcat ccccggcggg gctgctggcc    480
ggactgccac gctttagcag cctgagcccg ccgccgccgc cgcccgggct ctacttcagc    540
cccagcgccg cggccgtggc cgccgtgggc cggtaccccca agccgctggc tgagctgcct    600
ggccggacgc ccatcttctg gccccggagtg atgcagagcc cgccctggag ggacgcacgc    660
ctggcctgta ccccctcatca aggatccatt ttgttggaca aagacgggaa gagaaaacac    720
acgagaccca cttttttccgg acagcagatc ttcgccctgg agaagacttt cgaacaaaca    780
aaatacttgg cggggcccga gagggctcgt ttggcctatt cgttggggat gacagagagt    840
caggtcaagg tctggttcca gaaccgccgg accaagtgga ggaagaagca cgctgccgag    900
atggccacgc caagaagaa gcaggactcg gagacagagc gcctcaaggg ggcctcggag    960
aacgaggaag aggacgacga ctacaataag cctctggatc ccaactcgga cgacgagaaa   1020
atcacgcagc tgttgaagaa gcacaagtcc agcagcggcg gcggcggcgg cctcctactg   1080
cacgcgtccg agccggagag ctcatcctga acgccg                              1116
```

<210> SEQ ID NO 6
<211> LENGTH: 635
<212> TYPE: DNA
<213> ORGANISM: Homo sapiens

<400> SEQUENCE: 6

```
ggtctcacgg tagctgtcct tgggcttccc atcccgcagc gctccgatgt gaccctcctc      60
tgcgcggaaa atttcgaccc ggggcgccgg catcgcgacg tcagccagt gcccgcgagg     120 ctcccaggag atgcggggta gtaaggccct aaaaagagga gcctggacac ggcctggatt     180
```

| | |
|---|---|
| gagaaagaag caagcaaaca aaaatcctcg gtagctgtgt gtagcttcag gagtggagag | 240 |
| ccgagacaca ccgacggcgc cggagcgtcg caagaacaat ggttgctgca gtgggttggg | 300 |
| agagaggacc cggacaagtt cctaaaggca cgggaggaac gcgggcaaac caggtttagg | 360 |
| gccccaggcg aattgtgaa ggaatgactt cctcaaccta tcagcaccgt ggacaattcc | 420 |
| cactccaacg gccctgacct tcggcctact agattcagca aaaatctctc ttcctcccct | 480 |
| gcttcctcct ttccttcctc ccttcctcct ttccttcctg ccttccctcc ctccccttcc | 540 |
| tcctcctttc cttcctttcc tccctcccct tcttcctcct ttctttccct tcctcctttc | 600 |
| cactcttccc tgtttgcttt gtttcaaaaa caaaa | 635 |

<210> SEQ ID NO 7
<211> LENGTH: 17964
<212> TYPE: DNA
<213> ORGANISM: Homo sapiens

<400> SEQUENCE: 7

| | |
|---|---|
| ctaactatct cacaatatag gtccccaacc actgaccaaa ctccagtcca ggcagccacc | 60 |
| agctggcctg gtcttgctgc ttcctttagc ggcttccaag gtccagggac aggggggtctg | 120 |
| ggccaccaag aggctctgct aggctgtccc tgcagccaca gccaccccac tggacccctg | 180 |
| cctcccatct gagaggacag ccctcttcct ggagctggga tctgacactt gctgatacca | 240 |
| acggcagata ccaggtaggt ccctccctt tctcttcctt gagctcctaa aatgccactc | 300 |
| ataccaccct ctgcactcgg caaaggccac tgtggcttaa tcaaatcagg cacccacaaa | 360 |
| gcttcaagac tggaaaagat gccttggcta acccacccat ttagtggacg aaacactgag | 420 |
| gccgtcagg ggagtggcag ctggccacag actgaaccat agacttgggg cccagacctg | 480 |
| gggcccctca cggagcctca gagggtgaaa gggacttgct caagtccacg cagcggtggt | 540 |
| gggtgagctt tgtcttaaca acgagcactt tctacttcat cacagaccat gagtggcatt | 600 |
| gtgtttgttc acccgatgat gggtggccac tggcttgttc acccgatgat gggtggccac | 660 |
| tggcttgtca caggagtatt tccgagagga agatgaggga gcttggggct gaaggccagt | 720 |
| gggtttggaa ggaagcaaca ttcatgtggt taactgataa ctgggcccca tccctgggcc | 780 |
| tccttcctcc ctccctgtcc ttagcctgat taagaccaac ttacccagct gctaatcatt | 840 |
| gctgagcctg ttgattttgc cttaaaaaat taactgggca tgagtttgcg gttttcctca | 900 |
| cccctaaccc tgaaaaggcc tgggtgggca ggaggcctcc agggttatgc aagaggccgc | 960 |
| tggcctccca acgcatagcc cacggccacc tcggctgctc tccaaagaag aggctttgct | 1020 |
| caagagtcaa cagtctgctt gttcccctg tgctgggtcc tgagcaaatt tgctctgtta | 1080 |
| ccaaagagag ataaaggcag ctgggggaga gctttccaaa cagggatggg aagcggcagc | 1140 |
| tttgagcttg gggttctaga actctgcagt gtcagagcca ggagaatctt taggaggatg | 1200 |
| tgggctgggg tttttcaagc tgggttccga ggctcccagg agccaagggt atgcatccac | 1260 |
| aggcccagct tcaaccagcg actcccttt acatgtagtc ttaatatttt atttgagggt | 1320 |
| tggaaaacca ctgattcagc cccatcccct cattgcacag atggggagat ggagatcaga | 1380 |
| gggggaagtg acttgtccaa ggacagaagg tcacctcggg tattcagggg ctccagccag | 1440 |
| catgggaatg aatggtgggc tctctgtgga cccgggcaat gtcttgaaag acattggtga | 1500 |
| acaagacggc tctgcaaacg ccttgccatg ccgttctccc cctcctccca gggctggctg | 1560 |
| gaagcagaga ggtgcctgag agccattgga agacccaagt caggggaatg cacctggctc | 1620 |
| tgtgtcccat gggccctgtg aggatatgac cagcagccag gcactgcaaa ccggagacta | 1680 |

```
cgttataatc catctcagcc acgtcctgtc tctggaggca tcagcacttt gggaggctga    1740
gatgggagga ttacttgagc ccaagagttt gagaccagcc tgggcaacat agtgagaccc    1800
tgtgtctatt ttttaaaaag attttttaaa attaaagaca gatgcccagt ccctatcaca    1860
aaaaaagatg tagagccctg ccctgactct ctccacctct ctgagcctca gtttcttcac    1920
ctgtaaattg ggaattataa tacttaactt ccagggttgt catgaaaatg aaatgaagca    1980
aaatatacac attgatcatc atggccactg gatatgcagc tgttttagga gctttgcatg    2040
tgttacttcc ttgatcctcc cagccactct gggaggtagg caatgttttc accaattttt    2100
tacacaccag aggcacaggg aggttgagcc atatacccat gctcacacag ctgatgagaa    2160
acaagaagtg gaattggaac ttgggcagtc tgtctctaga gtctgtgcct ctaactccag    2220
ggctacccct cccttccagg gatgccagtg agagatggcc aggagaaggg cagagagcag    2280
ggcactgtgg gagatgctga ctgtaaggct ccggaggtag ggcagagagt atggtctgga    2340
gaatgatcag gaaggaagcc aggaggactt ggatctgtgt gggtggagct tctccgcagg    2400
ctgcctcctg ccaggtggct tatgacatct gggctgaggg tgttgctgtc ctcctgttta    2460
tgttcatccc tcctgtttat gttcctgaat ttatctgcag gggtgacctt gggaattaga    2520
tgcggccttc ccggcccttg tggggcctga aggctgatgg gagcccctgc ctgacccaga    2580
ctctggtttg gggagtgagg gctgagccca catcccagaa gccacccttg gtctccccat    2640
actcttgttc tgagggcccc cagggatttg ccaggtcact aaggtgaagt gtttggaagt    2700
cctgaggctc agatcagagt tactgccctg tacagttgtg caggttgctc actgcacaaa    2760
ggttctccag ccaagagggc aggtagggat ggaaacccag cccttgttcc acttgccaag    2820
cgaagtgccc atggagctct gcctgccag agtggggtgc cttttttctta tttgccctag    2880 ggcttcatgt aagctgctgg gtgtcctgcc ccagctctgg ttccagccac tgtgtgtcct    2940
tgggcaaggt catttccctc cctggccttg gtttcccatt ggagaagttt tgtctaacaa    3000
agcagagact catctctgaa gatgaaatag aatcatctga aaccttttaaa atatacagat    3060 gttggccgaa catggtggct tacacctata atcctagcac tttgggaggc tgagatggga    3120
ggtttacttg aacccaggag tttgagacca gcctgggcaa catagtgaga ccctatgtct    3180
attttttaaa aagattttt aaaattaaag acagatgccc agtccctatc acagatcaat    3240
gatcgaatct tggggtaggg gtgggaggt gccaggcgtc tatattttg tgcagccaat    3300 attgagaccc actgtagggg ggcttcaaat ttgaacctgg aaagccttcg atggcatcaa    3360
gttctatcac ttactacaac ttactagtca aaacctcagc gaggctcagt tttcccatct    3420
gtaaagaggg aatgatgatc gtttcctcac aaaatcaaaa tgccaattaa atgagataat    3480
gttcagacag tgcttggcac catgttcccc aagtagggag ctcctgattc ttgctaccaa    3540
gactattatt gttgttatgg gcaatttgac gttgacaaaa taagggcct tctaggtca    3600 aggattcggt gacttgaaga caggcctcct ctgttgcttt gagtcaattt ctagtacctg    3660
ggcctaaatc ttgactgcac accggtcata ttattgaggt atgtgttatt attattattt    3720
aatattttac ttaatttgtg aacatcttta catttagttt tgaattggtg ctacattcgc    3780
atggttcaga atcaaaacat aaaaggtgta aattgagaag tcttgcttcc agctgtctcc    3840
tgttcacctg ttctccttga cttcctcact atggggaacc acatccctta cagatgtatc    3900
tgccaaggtt tctttataca gaccagatag catgtaagat catacatgag tagcctctgc    3960
tcttacactg ttctgtatct tgtttggttc atttaatatc acaacctgga gatgcttcca    4020
```

```
tagcagctga gagcaagctt tgaggatgga agggttctcg tctcccatca caggtgagga    4080
aactgaggct cagagaagaa acatcatttt cccagtgagc caaggcaatg gtgttagaac    4140
tatctctacc tggctccaga gcttgtgttt atgcccctgc accgatacgg ccttccatga    4200
agcccggccc agaaagcttt ggagtctggt tacatctctg ccatgcaggc ctggccttcc    4260
caggacaaga ggtgaggagg ggggctgtcg gggtcctcac tgtgtctgga ctcagaaatc    4320
ccaaagagag gatgaagtgt agaacaaaga atgtcccaag tcatccagat agggacccag    4380
tgggaaggtg tccctggat ggaatagtgg gggcctggtg gctgtgcccg tcagcactgg    4440
agaacctgcc aggaactctc tgccagcctc aggtggtgcg ggtggcaggg gaagtcagga    4500
ggaggatgag aggcagggag ggaagcatgg ccgatgagac aagctctggg tgaggggatg    4560
gaggggaccc catgcctgga gctcaggaag gaggatttgg agttcaaggc agaagtggca    4620
atgagatttt aaccgattgt tttctgctca gggaacttca gggttccctc tggattcttg    4680
acctgcttca gtttgctgac tcactggctt tgggcaagtc attttccctc tccgtgcctc    4740
agtttcccca actgcaaaat gagagagata agagatctgg tctttaggca gccttggact    4800
acccctaata ctctacgggg ctcctctcac cttgttgagg tcgtctggat tctccttctc    4860
tgattggaac gtcattcacc catcagggcc atggacgttc ctgggttagg ggatgagggt    4920
acaaatcctc cacactgctc ccagtctgga atcctccccc ttggttctgt gtctctctcc    4980
taccatccca tccttccttc caggcagatg tggagtcagg accatacctg gtgggtcctg    5040
ggggaagccc tggccccagt ccgacatcct cctcctgctg ctatggggtc ccgcacagtg    5100
cacaacctct tcatccttga gggagctcct gctggcccct ctcagcaccc cagaccctgc    5160
gagggccgct gggcagagtt aatcccttaa tactggtcac aatgagattt cagggatggt    5220
gggaggcggt ctccatggaa actgcagacc tgtccaggat ccatgcaagg aattagcccc    5280
agggctctgc aaggggctcc tagagagcca accccaatag gaatgggaga cacagtggtc    5340
tggactcctg ggtcctgctc tggccctcct gttgtctctc tggagggctt ggaaaaaacc    5400
ataactcttg cattgcttca gtattctgct caactggaca gagccatatt cacagggaga    5460
gccctatcac ctttctgagc gtgtttctcc atcccctat tggcattgta atccttaacc    5520
cagtggcttt tctagaagag tgcaggcttc agagtctgcc agacctgagc ttgaagctca    5580
gcttttccct ccacgactgt aaacttagcc gaggcatttc acttctctga gcctcagctt    5640
cctcatctgt atgatgggca caataatagc aacatggcat ccctcttgtg ctggctggtg    5700
ggtagtaaca tccagtgaat gtgagtctcc ttctcacctt ttcctgactg ccacgcccac    5760
actgcacatt tgccctcccc agcccctgc agcttccaga accccgtggt ctcaagcaga    5820
gagctgtcgc acttccttct ttgccttctc atcctccaag tcccatctta gtcatcttcc    5880
tccgggaaac agaacgccgg ggtcctcctc tgtcccccca tagcccccaa agctttacat    5940
catcatcgtt tagtcagatg gtaattagac tggttgtgtg cctcctccac tggactgtgt    6000
cccatctacc attgtattcc caggacccac ttgatataaa taggctggat gaataactga    6060
gtgaataaag gatggaaatc gtccatcgaa acagtcaaca tttattcagc accttctgcg    6120
tgcatcgttg tgggtggtgg agatgcagca gggaagacca tgggcaaaat atcccccctca    6180
gagggggtgca gatgagcaaa taaaaataca ggatgcccag tcaaatgtga atttaagata    6240
cacaagaaat acttcgttag tatgagcgtg tcccaaataa tgcatgggac ctgcttatac    6300
ttttaaactg tggtgttcat ctgacactca tatgaaactg ggtgtcctgt gttgtgtcgg    6360
gcaaccctac accctccctc acagagcttg cgttttggtg gagaggcggg ttgcagacat    6420
```

```
aagcaagtaa atacatgaaa aacgaagtca attacaaaca gtggttaagt gcagtgaaga      6480
cgcacagcgc gatgtgatag cacctgggga tgggcaggac gatcccctga gctagtggcc      6540
tttgcctgca caggtcattt tagctccaat gagatgccac tttgcaaaag ttctttgagg      6600
atcttaaagg gcacggtgga ggctgctaaa cttgagagaa ggactctgag gagggcaagg      6660
ggcgcacctg agggagtggg gctgctaagt ctcacttgat agactccaca gttttgcaac      6720
ttggatctgg gccttcacaa accttcgcga acccgcagcc ccaccCctcg ggtcagccaa      6780
tgtcttctgt ggggctggga gcaggggaa gaggccaaag gaactgtgca gagaagcgtg      6840
gccacccggg ccgcagctgg gagccctgac acccttTgcc gccccacctc atcccgcggt      6900
tgccccaggg cgcagggcag ggcaggcacc gcgctgggcc ggagggcgtc ccggaggagg      6960
cggccaagac tctccgcagt gctgcgcttt gcgcttcctg ggctcctcct cgtgccaac       7020 gcaggaactg gtgttcagaa acttagatag ccttagggac ttcaccaatc acagcaatcc      7080
cgccaatcac aggcccagac gcactatgtc tctccaaatc cagaggaggc ctgctcggtt      7140
cgatcaccaa tcacagctcg ttggatttag ttacctaaaa gaacatctcc ccatcacaca      7200
ccagcacatg gccacggcag caatcagaac gtaagatttt aaaaccagtt cccagggtag      7260
cagccgctgc ccttccacca cctactaaac ttctgttccc agcaccttgt tccaatgtac      7320
gggggtgggg ggggtctttg aggaaggttc caggctttgt gctgcttcca tgtggaagca      7380
gatgttagca tgtatggggc atgtataatg atattactat cagtaaatgt catacccatt      7440
atgaaaatta agataggcag ggcgtgatgg tgcatgcctg taactccagc tttaggtggc      7500
caaggtggga ggatcgctgg atcccaggag ttggaggctg cagtgagcca cgatggcgcc      7560
actgcactcc agcctgggtg atagagtgag actctgtctc aatttaaaaa aaaaaattaa      7620
tgtgtggata taggagtgtg gaaaaattat aacctttggg ttagacacac ctggagccca      7680
tatactatct ttgtgaagta ggacgactca cctcccttc ctcagtcgtc aaaagagaat      7740
gatagtcata tctacatgtc atatatcatc acccaccttc tctcaattat tcaagccaac      7800
atcttgcaag tcacaatctt tgtgttgtgt ttctcatgcc ttccagttca tcagaaaatc      7860
cagttcttgc caccctccaa acagaatcta gattttccat ctttccatct ccaccccagc      7920
caaccttatg catcatctct ggaggtctgc aaaagtcttt tcacttcttc ccttttttt      7980 tttttaaacc tgccagggtt ggggagggga tctcccccgc tccaccgccc ccccgcctc       8040 cccccccccc cgcctgcctc caccccaccc cttcactttt tctcctgtgg cttccctacc      8100
ccctactctt cactcagggg ccaagggtga tcttgtacaa atgtacattg gctcagatcc      8160
tcttctactt aaatttttat gacttcctat gcatttataa caaaactcat acaactccca      8220
cttaacactg tgaggccatg cacgcccttg ttttatatc cctccgtgtc caacctcatt       8280
tcattccact tgcccccacc cctatcagca gcaggcatac tagccatttt aaagtttttc      8340
tttcctgtct tgggggcctt tgcatatact ttcccctctg cctggaatac ttcttttttt      8400
tttttttttt ttttttttaa gatgaagttt cgctcttgtc actcaggctg gagagcaatg      8460
gcacgatctc ggcttgctgc aacctccgcc tcccaggttc aagcaattct cctgcctcag      8520
cctcctgagt agctgggatc cacacccagc taatttttta atttttagta gagacggggt      8580
ttcgccatgt tggccaggct gatctcaaac tcctgacctc aggtgatcca cccacctcgg      8640
cctcccagag tgctgggatt acaggcatga gccaccacac ctggcctgga atacattTta      8700
gtaagtgttt aatggatagt tgttggatga atgactgaaa aggtctttca agaggaactg      8760
```

```
atagtgatgt aaacttcaag tgctcggtgc gtaacaggta ttcaatgaaa aggattctat   8820
gcatatagta gaaattttgg aaaataaaat aaaaattgaa gatttaaaaa tcgtatgtgc   8880
tccaacattt agaaaggttc aaactcttaa tggctaacca gggtttcttg acctaagcac   8940
taatgacatt tgggctagag aattctttgt cgtggggact gtcctgtaca ttgtccctgg   9000
cagcatgtct ggcctctagc cactagatgt cagcagcact tttccctacc ctcaaggtgt   9060
gataatcaaa actatctcca gacatttata aatgtcccct gggggttgaa attatctcca   9120
ctgagaacca ctgtgctggg cttctaccct acaagaaat tttctctcag tcattcaatg    9180
cttctcaaat cttggtgtcc ataagaatca tctggggcca ttattaaaaa ttcagatggc   9240
agctgggcga ggtggcttac acctgtaatc ccagcacttc gggaggctga ggcaggtgga   9300
ccacttgagt tcaggagttc gagaccagcc tgccaaacat ggtgagacct cgtctctact   9360
aaaaatacaa aattagccga gcgtggtagc acatgcctgt aatcccagct acttgggagg   9420
ctgagacagg aaaatcactt aaacccatga ggcagaggtt gtggtgagcc gggatcgtgc   9480
cattgcactc cagcctggtt aacaagagca aaactctgtc tcaaaaaaaa aaaaaaaaaa   9540
aaaaaaatca gatggtggct gggcacggtg gctcacgcct gtaatcccag cactttggga   9600
ggtgggtgga tcacctgagt tcaggagttc aagaccagcc tggccaacat ggtgaaaccc   9660
tgtctctatt aaaaaaaaaa ttagccaggc gtgatggtgc atgcctgtaa tcccagctac   9720
tcgggaggct gaagcaggag aatcgcttga acctgggagg tggaggttcc agtgagtgaa   9780
gatcgtgcca ctgcactcca gcctgggcgc agagcgaga ccctgcctta aaaaaaacaa    9840
caaaaaaat cagatgcctg gggtcctacc tccaggtgcc aggaccaaca gtgggcctag    9900
tcatcagatt aaaaaaaaga aaatatttaa taatagagg tggggcatgg tggctcatgc    9960
ctgtaatccc aacactttgg gaggccaagg caggtggatc actggagact aagaattcaa  10020
gaccagcctg gccaacatgg tgaaaccttg tctctactaa aagtacaaaa actagctggg  10080
tgtggtggtg catgcctgta atttcagcta cttgggaggc tggggcagga gaattgcttg  10140
aacctgggag gcggaggttg cagtgagaag agatcaggcc actacactcc agcctgggcg  10200
acagagtgag agtccataaa ttaataaaca aacaaattaa ttaattaaaa aatagagacg  10260
gggggaggtg tcttgctatg ttgtccaggc ttgtcttgaa ccccagcctc aagcaaatca  10320
gcctcccaaa gtgctgggat taaaggcagg agccatggag cacctggccc aagtgtttaa  10380
tgagcttctg ggcacttctg ataccaggtg ccctcagacc gcactttgaa aactcctcaa  10440
ggaggcctct caatcacctg atcaccaaac cctgtgtgag gctccctacc cacctggacc  10500
ctctccttga attcctctcc tttccaatta ttacccttcc ctagatagca agtggtgaca  10560
gaaccaaacc ctagctcagc caaagcccaa attgcctcat ctcccttcag ggaataggca  10620
aaaaaaaaa aaaaaaaaa aaaaaagat cacagagttc agctgaaacc acttaggaaa    10680
tatcagcatc cccacctccc cacccaaaag gactcctgag tggcagcctg agaggtgtgt  10740
ctgctcatca gaataatgtt gtcagactgt gttctttctg ggggatcatc acactcccct  10800
ttctgggaac aaatgttggc cacttggtgg gatgggccat catgatctac gtcagacaaa  10860
ttcagtgagt catgactcag cctatctctc tagacccatc ttttatgccc ccttacttat  10920
agtctctctg agggctgttc tcaactattc tatttctctc ctttccggca catgatgggg  10980
attacatttt cttgcttcct ttgaaatgag atgtgaccat gttacttgtt tcaggtaacg  11040
agatgtgagc agaaacaacc tgtgtcacac ctgggcagaa gctttaaagg ccagtgctgc  11100
ccttgtttgg gaagcaagta tagatatgaa tcgttccaca acgcggagcg ccccctgccg  11160
```

-continued

```
acccatgctg ggcgtgtact ataggtgagc aattaacttt gctgttcaaa ccattgagac    11220
ttaggggttt ttttgtggtt gcaagctaac ttcacttcac ttgactgaac acagtctttc    11280
caaagtttca ctaattttt aatgaccatt atgattttt catatctgta acatttttct     11340
tacatcaact cacttcttt tacttcaatt tattttagaa agaaatatta ttactaccaa    11400
atgaaacagt atcataagta gaaagcaatg agaaaataaa cagaatgaaa gaaatcctga    11460
tatcaaatcc tgacttaata ctatttgcct ttcaaagcct ctggaccttt ggtctttatt    11520
taaaaaaaaa aaaaaaaaa aaaaaaagga gccaggggcc aggcgtgatg gctcacacct    11580
gtaatcccag gaatttggga ggccgaggtg ggaagatcac ctgaggtcag gagttcgaga    11640
ccagcctgac caatatgagg aaaccccatc tctactaaaa atacaaaaat tagccgggtg    11700
tggtggcatg tgcctgtaat cccagctact caggaggctg agacaggaga attgcttgaa    11760
cctgggaggc ggaggttgca gtgagccgag atcgctccat tgcactccag cctgggcaac    11820
aagagtgaaa ctccgtctta aaaaaaaaat gggagccagg tgcggtggct catgcctgta    11880
atcccagcag tttgggggc tgaggtgggc agatcacttg aggtcaggag ttcaagacca    11940
ccctagccaa catggtgata tcctgtctct acttaaaatg caaaaattag ctgggcatga    12000
tggcatgtgc ctgtaatatc ccagcctctt gggaggctga ggcaggagaa tcacttgaac    12060
ccaggaggcg gaggttgcag tgagctgaga ttgtaccact gcactccagc tggggggaga    12120
gagttgagac tccgtattta aaaaaaaaaa aaaaaagag gtccccaaga gtacttctca    12180
atcttttgga tccccaaagc tgtctaagat tgtcagaata tttgaaggca gcacagtatt    12240
gaggctgagt gtaccaattc tggaacttga catcctgggc ttaaattctg gttcagtcat    12300
ggactagctg tgtgaccctg gacaagttac tgaactgctc tgtgactgtt ttcttatttg    12360
caaaatagtg accataatga tgtgtatggc attaggtcgt ggtggggatt atttgtgtta    12420
atgtataaaa agggcttaga agtgtgcctg gcacttagtg agtgctatgg aggcattacc    12480
tataaaatga tggcaggatc cagatccaaa tagatttggt gaattattgt ttgttttttt    12540
tgagacaggg tctctgtcac tcaggctgga gtgcagtggc gccatcacag ctcactgcag    12600
cctccaagtc tccaggctca gatgatcctc ctacctcagc ctccagagta gctgggacta    12660
catgtgtgga ccaccacccc tggctaattt ttctatattt tgtagatatg ggatttcacc    12720
atgttgccca ggctggtctg gaactcttgg gttcaagcaa tctgccccctt cttagtcttc    12780 aaagtgttgg gattacagac gtgagtcacc ccacccagcc tggagaaatg tttgaactcc    12840
atggagataa gtaaaaaatc ctctgcattg gttaaaaata aatcacctgg atgatttat    12900 tatttagtgt agatgggaaa agctaccta gcagaaagtg acatagcaaa attctagagg    12960
ttttacttgg tggcagctgc ccaaacctct aacccagtcg tatgtatcat tagagagaat    13020
gtagttccca ggtcagagga gctaagaggt ccttggcatt ctactcctaa ggagcatata    13080
tggacaattg tgtttagttt tcattttaat atgaatactt aaaattttcc taggatggca    13140
gaggatgaga aagctatgcc ccttaggccg agtgcagcgg catggctcat gcctgtaatc    13200
ctggcgcttt gggaggccaa ggcgggcgga tcacgaggtc aagagatcga gatcatgttg    13260
gccaacatgg tgaaactcca tctctactaa aaatacaaaa attagccttg cgtagtggta    13320
cgcacctgta gtcccagcta cttgggaggc tgaggcagga gaattgcttg aacctgggag    13380
gcggagggtg cagtgagccg agatctcgcc accgcactct agcccggcag cagagcgaga    13440
gttcgtctca aaaaaaaaaa agaaagaaag aaagaaagaa agctatgccc cttgaagaat    13500
```

```
aatcaaagat ccaaaagagt tttgggctgg gtattggaga agaggagaga aaggtggtgt   13560
agcagagtgg tcagggccat tgcctttgaa atatcagtgg tgccatttac atagctgttg   13620
gaccttgcta aaatcataag ctcttcaagc cttatttgct tcatctataa aataggaatc   13680
aatgatagga ccttttcata gattgctttg tggagtaaat gtgttaaacc ttataaacct   13740
ggcaggtagc tgcccagcat atagttgcgt tatttactca attcaaagta ctttcctgcc   13800
gggtgcggtg gctcaggcct gtaatcccag cactttggga ggctgaggtg ggtggatcac   13860
ttgaggtcag gagttccaga ccagcctgac caacatggtg aaaccctgtc tctactaaaa   13920
acacaaaaat tagccgggcg tggtggcagt cacctgtaat cccagctact tgggaggctg   13980
aggcacaaga atcacttgaa cctgggaggc agaggttgca atgagctgag atcgtgccgc   14040
tgcacgccat cctgggtgat agattgagac tcagtctcaa aaaaaaggca acaaagtact   14100
ttcctttgga aaagagtgcc cactggctgg gtgaagtggc tcacgcctgt aatctcagca   14160 cttgtgggc  tgaggcaggc agatcagttg aagccaggag tttgagacca gtttcacgtg   14220
gccaacatgg tgaaaccccg tctactaaaa atacaaaaat aagccagatg tggtgtcatg   14280
tgcctgtagt cccagctact caggagagtg agacaggaga atcatttgaa ccctggagtt   14340
ggaggttgca gtgagcagag atcgtgccac tgcactccag cctgggtgac agagtaaaac   14400
tctgtctcaa aaaaaaaaa  aaaaaagct  ctcactgatt cctacagctt cagagaatga   14460
acgaggacca aaatgtggat gctacaggga ggaaacttga ggctcaaaat ggagatcttt   14520
ctataaaata caattgttct accacaggaa aagctgcttt attaagtagt gagtattccg   14580
tcattggaag tattaagccc aagctaaatg gtcaactgtc agggaaggat ggtgagagga   14640
ttccagtggg ttagaggtca aagagcgtct accaggtgca aaagtcttaa ttaacaaagt   14700
actatcaaaa ccaaattcat gtttgggaaa ctgtatatcc acatgcaaaa gaatgaaatc   14760
agactctttc cttacaccat atacgaaaat taactaaaaa tgagtttgac ggaaaagtat   14820
aaaacctttg gaataaaaca taagggaaaa gcttcatgat attagatttg gtgatgattt   14880
cttggatatg acaccaaaag cacaggaaat ttttaaaaat tagataaatt ggactacatc   14940
aaaattagaa aaatttgtgc accaaaggac acttgactga gtgaaaaagc aacttacaga   15000
atgggagaaa atatttgcca atcatatatc tgataagggg ttaatgtccg aaatatataa   15060
agaactctta caactcaata acaacaacca aaaactttaa aaatggacaa agaggccagg   15120
tgtagtggct caagtctgta atctcaccac tttgtgaggc agaggcagga ggattgcttg   15180
agctcaggag tttaagacca gcctgggcaa catagtgaaa ctttgtctct acagaaaaat   15240
ttaaaaatta gccaggcatg ctgcacacct gtagtcccag cttacttggg aggccgaggt   15300
gggaggacca cttgagtcaa ggagtttgag gctgtggtga ccacgatcc  tgctgctgca   15360 ctctagcctg ggtgacagag caagacctgt ctcaagaaaa caaaaaaatt ggcaaaggac   15420
ttgaataggc atttctccaa ggaagatata caaataacca ttaagcacat aaaaagatac   15480
ttaacatcac taatcattag ggaagtgcaa atcaaaactg caataagagg ctgggcacag   15540
tggctcatgc ctgtaatccc agcactttgg gaggccaggg caagtggatc acttgaggtc   15600
aggagtttga gaccagcctg gccaacatgg caaaatccca aatctactaa acaatataaa   15660
aattatctgg gtgtgggcca ggcacagtgg ctcacgcctg taatcccagc actttgggag   15720
gccaaggcgg gcggatcacg aggtcaggag ttcaagacca gcctggccag catggtgaaa   15780
ccccatctct actaaaaata caaaaattag ccgggcatgg tggcatgcat ctgtaatccc   15840
agctactcag gaggctgagg taggagaatc gcttgaacct gggaggcaga ggttgcagtg   15900
```

```
agccaagatc gcgccactgc accccagtct gtgccacaca gtgagactct gtctcaaaaa    15960
aaaaaaaaaa aaaaaaggaa aagaaaaatt atccgggtgt gatggcacat gcctgtaatc    16020
tcagctacct gggaggctga agcaggagaa tcgcttgaac cctggaggag aagtttgcag    16080
tgagctgaga ctgcactact gcactccagc ctgggcgaca gagcaagact atgtctccaa    16140
aaaaaaccaa gacaaacaaa caaacaaaac acacaataag agaccacctc acacccatta    16200
ggatggatat tataaaacaa caacaaaaca gacaatagta agtgttggtg aagatgtgga    16260
gaaattgtaa ccccttttacg ttcctatcac tgctggtggg aacgtaaaat agtgcagctt    16320
ctgtggcaag cagtatggcg gcttcctaaa aaatgaaaaa tagaactatc atatgatcta    16380
gcaattgtac tcccgagtat atacccaaaa gaaccaaaag tagcatctgg aagagagatt    16440
tgtatactca agttcatagc agcattattc ataatagcca aaaggtacag gcaacccaag    16500
tgtcaatcaa tggatgaatg gatcaataaa atgtggtata tgcatacaat ggaatattat    16560
tcagccttaa aaaggatgga aattctgaca catgctacaa catggatgga tcctgagggc    16620
attatgctag gggaaaagct agtcacaaag aacaaatact gtatgattcc actagcctac    16680
aggaaagtag tcaaattcac agagacagaa agtagaaggg gtttgccagg gcctgggaag    16740
aaaggagaac tattttcttt tcttttcttt tcttttttt ttttttttga cgggtct      16800 ctctctgtgg cccaggctgg agtgcagtgg tgcgatctcg gctcactgca acctccactt    16860
cccgggttca gcgagtctc ctgcctcagc ctcctgagta cctgggatta caggcacgca     16920
ccaccacgcc cggctaattt ttttgtattt ttagtattta ttttgtattt ttagtagaga    16980
cgaggtttct ccatgttagc ctcccaaggg gagctatttt ctaatgggta cagtttcagt    17040
gtgggaagat gaaaaaagtt caggtgatgg atggtgctga tggttgtatt acaatgtgaa    17100
tatatttaat gtctctgaac tgtacgttta aaaatggtcg gctgggcgtg gtggctcaca    17160
cctgtaatcc cagcactttg ggaggctgag gtggatggat cacctttggt caggtgttca    17220
agaccagcct gggcaacata gtgaaaccct gtctctacta aaaatacaaa aatcagctgg    17280
gtgcggcggt gcatgcctgt aaccccagct actcggagg ctgaggcaga aaatcactt     17340 gaacctggga ggtggaggtt gtagtgagcc gagatcacgc cactgcactc cagccgggcg    17400
acagagtaag actctgtttc aaaaaaaaaa aaaatacat gcataaaaga tgtttctaag     17460
agtgctaaaa aatgcctaca aattgataag gaaaggtaaa taatacaata gataaatggt    17520
caaaggatac aaacaagcac actcataatg taggaagctc aaatggcaaa agagcctctc    17580
cttctctagt aatagaggaa atgtaaattt gaaagtgaag cataatttta cattcagtat    17640
cttacaaaat caagtgctga tgaggttgta gagcaaccaa aactctgtaa ctattgttgg    17700
aagtggaagt tggcattcaa gaatgagcaa tttagcaaca tctcttaaaa gtgttgatat    17760
ccactgtcta agatacagaa attccatctc tgcatgttac ctagagaaac tctcatccac    17820
aggtataaga atagtctttg gagcatcatc tgagatagtg agccaagatc gtgcaactgc    17880
actccagcct gagtaacaga gtgagactcc atctcaaaac aaacaaataa acaaaacaga    17940
ataaatatac tcaggatatt taca                                          17964
```

<210> SEQ ID NO 8
<211> LENGTH: 30003
<212> TYPE: DNA
<213> ORGANISM: Homo sapiens

<400> SEQUENCE: 8

-continued

| | | | | |
|---|---|---|---|---|
| agtgcccagc | agctgcctcc | tcaccctagc | tgagctgacc | acaagattcc agacctcagc | 60 |
| tggagctgca | gcctcatact | ggctgagtgg | ctccaagaca | cagaaggaag cagggtggca | 120 |
| ggctgacctc | agccagctgc | ctgcccctc | tcctctgagg | ctggcctggg accgatgggg | 180 |
| ctcttccctc | caggaggggt | tccgggcct | cctcttttcc | cctacctccc tgtggagaac | 240 |
| tgtccacccc | tccagatatg | ctccagtgat | gtcggagggg | atgcctcaat ctggcgagac | 300 |
| gcagcggcaa | caaaatctgc | tcagagacaa | acggacatgt | tgctgatatg aatctcactt | 360 |
| ggtgagtggc | aacaacagag | tcctgcattt | gggtctgtgc | agtcgtgcac accagagacc | 420 |
| gctgaccccc | gcccgcagca | cagggaactg | catatataca | cagcaggtac aaatatgggc | 480 |
| acacgacaaa | acgcccatac | aggataaaga | tgcaggaaga | cagggcact ccaacaggtc | 540 |
| cgcatgcaca | aacgcatgtg | ctctatgacc | cgcacacaca | gcacacatgt acaaacatcc | 600 |
| acagacacaa | gtacacacac | atacacactt | acatacataa | gcaagatcaa cacgggcaac | 660 |
| tcctaagaca | caaacacaga | cccactcaat | gaatacaaag | gaaaatagac ccagaactca | 720 |
| cacacagaga | caaatgaaca | cacatatgca | aatgggttcc | tgaaggcatc accccaccca | 780 |
| tacaacctac | atggaaactc | actatccacc | acgaacgcac | acacaacaca cacagtgctg | 840 |
| agttggcttc | gtagttagca | aaacttccct | gagagctcca | ttttccctaa gtgccaattt | 900 |
| catttcccta | ggaaagtccc | aaagacaccg | agaaatgcgg | ttatgtctcc aaccaccatc | 960 |
| tccagggata | caacatccct | tgccgtctct | ctgaacctag | gcccaagggg ttcacgaagg | 1020 |
| ggccgtgctg | ggctgaatcg | ctggagctgg | gcaccaaggg | ggagctcacc atcacgtcac | 1080 |
| tgtgccaagc | gccaagcaga | gccactgtga | ggcagtgagg | actggaaggg cctgggagga | 1140 |
| atagccggga | tcgactttg | ctggaaattg | gcccttgcag | gcctcccttc acccagaatg | 1200 |
| cctgtgatca | ctgtgcctgg | gcacatgggc | ttcacttggc | aacacctgtg ctggcctgta | 1260 |
| ggaccaacct | accattttgt | atcattctcc | tcccacccca | aagttgagtg ccaaagatct | 1320 |
| gctcctggac | ccaggcacac | ctgccccac | tggcacacct | gggcacatct gcccccacct | 1380 |
| accattgccc | atcgtcaaca | cctgcacatt | ctcaaattcc | agggtggtgt aggctgggtc | 1440 |
| cagtgcagca | ctgtagtcgg | ccatgtccat | gtcgacgagg | ttttggaga gtcgcattct | 1500 |
| ccctgcctcc | acgccgcggc | cacctgccct | accctgggcg | cccaccccga aggccccgc | 1560 |
| cctccgccct | cccactgcct | cctcccagtg | ccctctctgc | cttcctttca aaccgtcctc | 1620 |
| tgggaagatc | tgctgggagt | cttggcctag | cctctgtgaa | ggggtggagg ctctgccggg | 1680 |
| gaggggtggg | ggttaatggt | taatcggtcc | ccgccggtg | gataggctgg gcggggctgc | 1740 |
| agggatttgg | ctgtttgttg | gtttctggct | gacacccggg | gtgctaatta caactgctgg | 1800 |
| ggccctaact | caccgatgtt | cagttatcaa | ttgtacaagg | caggcatcat gactcacggg | 1860 |
| cactcatttg | acccttgact | cacccacccc | tccaagccat | tgtcaccca agtcaggcat | 1920 |
| tctaactgat | actatcaggc | actgacagcc | tacctccgag | atccctaat tcaataactt | 1980 |
| cccaaatcat | tgacttctac | cctcaatgct | tttgcagaga | taaggctgcc ccatggccca | 2040 |
| cgatttagaa | acctaaatcc | caggccccag | atgccaatct | tctggatcct tgttctggga | 2100 |
| gctcccttcc | agttccccg | cagtttcccg | gttcccctgg | gagcagaatg gactggaagt | 2160 |
| ttgggagggc | cagattcacc | tccaattccc | cgctcctgct | ccctgtgatc ccaccctgcc | 2220 |
| cctctccgtc | tcccacagct | cccagtgttt | ctgcccagg | ctggctccat ctcggatttt | 2280 |
| cccatcacat | tctcctgttt | ccctcacccc | caccccctcc | cggagcaggc agagacctgg | 2340 |
| atttacattc | aggcacctac | cgtctactaa | ctgggacctt | gggtaaatga ttctcctctc | 2400 |

```
cgagcctcag tttccttttc tgtaaaatgt acaatcaact tcaaagggtg gtttgagaag    2460
gaaatgagat ggcataaatc aagcaccaag tggggcctgg tagacgtcca tcctcttccc    2520
cctcctccct ctccctgttt cgtatccccc ttgccatccc cctgtttctc tccacccgtc    2580
tcctaccttc agagtgggct tgtgggggt atcgccagtg cagtcacagg caacccaacc     2640
cttagaaagt cctggttcct ggttcagtgc tctgctgtgg ttgtcctaaa attcatcatg    2700
acttttgaac aagggattgt gcattttgt tttggacggg gccctgaaaa ttacacagct     2760
ggtcctggct gtctgaagct catggtgcac tctgttcttc tcactccctc cagccctcat    2820
tgccttctgt gcagacattt tcaagggctg ccaatcaatc tggggaagta aagtcttgat    2880
gtagaaggca gagagtgagg gcagaggaag aaaagcctga gacttgggag gcctgggagc    2940
ctgtcctcca ctgctggctg aagggcagg ttggagggcc tcggtgacac ctgtgagcaa     3000
gagtgggcga attagtggga gcaccaatta atgagtgagt gtgtggggga attgatgagt    3060
gggtgaatta ggagtgagtg aattagagac agggagaatt aatgagtgag ttgagtgaat    3120
gcatgaatga gtgagtgaat aacgaatgag gggtaaatta ctgagtaagt gagcaaatgg    3180
gtgggtgaat taatgagtga atgggtgggt gaattaatga gtgagtgaat gagtgaatgt    3240
gtgggtggat taatgagtga gcaaatcggg agtcagggca tgtgtgttcg agtggtatga    3300
ggaggcatct tcatgttctt tccactgcta gaagcccttt ctctgccctg cttagcttta    3360
ttctgtccac ttgatctgac ctctgaagct gagatgactg gggagtgcta ttgcctgtag    3420
ggaaagggga gagggagcaa ctgttgtgga ggacaagaga ggctagattt gatgtcagga    3480
gacctggggt taggaactag ctcagtcact attccgataa ctttatttac atcgtctctt    3540
ctcagggctt caatttctcc ctctgtaaaa tagaaagatg atcctggctc agttttctgt    3600
tagccaggac aagactctga gggagggagc aagaggcagc ccctgcaac ccacactatg     3660 agacttgata aggggctgaa agagaccaaa taccggcggg ttcctcccat gcctacctca    3720
ggagtatctg acctggctcc accggccttg ggggcagtgc agaggtggga agaaacagaa    3780
gatccgacca aggggtaaac acagaagaga tgtggagggc agctccggga ggagcctcca    3840
agggctgagc ccaggcctct gccacctgcc tggcacctat ggcaggccac aggcacagct    3900
actccccaca caatccagga atacatggcc tcttccactc tgaggcacag ttccacattg    3960
cttaacgggg aatgtgatca atgtcatgtc agaatttcat tggcaacaaa ataacaatg     4020 cattttccat agatgacat cttagattca attaaataag gtctacgatc aaccaagatc     4080
aaccacacca tgccacagcc atgacccgtt atatccaaga gctactaggt ggacactgca    4140
aatgaagagc tattagatac atgaatcatg acatacctga cttaccaaat gcacaatctg    4200
catgactgcc taggaggcac attctagatt cacatcccac cacattataa cctaccccat    4260
aagtaaatct atccactcat cactgtaaat tgcataatct attacataca tgattcattc    4320
cacccttagc caacgccaaa cagtatctcc tagatacaca ttcctcatat aaatgacgca    4380
ccacctataa gatctgctgg ctctgtgacc tcaggcaagc tattatttct tttgttcttg    4440
ttgttcattg ttactacata gtttatttaa accaagctat gataatacag ctgcccagaa    4500
tctttgtgga ttacagatgc aaagtaactg agacgtgtc cttgcaccta tagttcagta     4560
atagacagaa agtttgttac atttactaag tacagagaac tgaatacaca tgacattgta    4620
catccatctt tttgctttgt atttccattt taaacatatg tatgttacaa ctttacatttt   4680 taaatatgac tccatgtatt ttgtgacaat ggctaagaac gcaatgatcc catgcccctg    4740
```

```
aaataagcac actttggtct gcaatgcaga atgttttcat tggggtacca aacaaaccct   4800
taacacataa cagacaaaaa ctccttaaaa atcagattta atacaatgtt cttcatgtta   4860
gataaggaga aagaacggga ggtggaaaag gaaaacattg gggtacttta aatgtacagt   4920
gtcttgagac cttgaaagtt tcaggccagg cacaggggct cacacctgta atcctagcat   4980
cttgggaggc cgaggcaggc agatcacctg aggtcaggag ttcaagacca gcctggccaa   5040
catggagaaa ccctgtctct actaaaaata caaaaatcaa aaattagcta ggcatggtgg   5100
catgcccctg cagtccaggc tacttgggag gctgaggcag gagaatcact tgaacctggg   5160
aggtggaagc tgcagtgagc cgagattgtt ccactgcacc tgggtgacag agcaagactc   5220
tgtctaaaaa aaaaaaaaga atgttttctt caggggatga agagacgttg gttcatgggt   5280
acaaaaataa gtgagataga aggaataaga tctagttctt atagcacagt agagcgatta   5340
tagttaacaa tcatttactt tatatttcaa aatagccaga agagaagatc tgaaatgtac   5400
ccaacacaaa gaaatgataa atgtttgagg tgatggatat cctaaatact ttgcatggta   5460
tgcatgtatc aaaatacatg tgctccatat atatgtacaa ttattatgta tcaattataa   5520
aaagtttcat tcccttcctc caagggattt ttttttttaac tagtggaaaa aagaaagcaa   5580
cttcataacg ccctccagtg aggaagaaca ttatcctgac aatgcttagg tgctttcata   5640
tgagcacata ataaatacag gaagtcacag agcaaatgtc acagtattgg tttggttttt   5700
atttctatgc ttataaaaaa tattaagctt ctttctgtgg actgagtggg tgttagcctg   5760
tgggtattgg tctctggtgc ctgtatacca gtgactattt atattccaag cccagggcca   5820
gctgtctgca caaggcaagt ttttatttcg aagccttggt tactccttct gtacaagggg   5880
tctaacttgt cgtttgtcgt gaagattaaa tgagagagta gataagcttc ttagcctctc   5940
ttcccctgac ctctctttag gggaataaac cacagacctt gtgggtcaga tagatctagg   6000
ttaaaatcca ggcagtgcca atgtaccaaa ctctgtgacc tcaacttcta cttttctcag   6060
ccttagttta agcatcagaa aaattgggtt gataccttct tgtagggat ggttcaagca   6120 ttaaatgacc acgtgtaggc atacagtaca atagtagcaa tcactgtcat tggtcattga   6180
ttgcatgaca cactggccac ataatcagtt ggaatcagga cccctgctca ggacagctcc   6240
aggtaccaca cacccagcca tgaacaagca ctagcctcaa tgccatcaat ttagcagctg   6300
ttctttacct ctgctcactt gctgtcgggc cccagctcaa gaggcagcag attccagggg   6360
atagcagagg acctcagagc ccacagagag acccagttga gacgggaagg gattgccctg   6420
ggcaacctgc agttggggag gcatgtgtag ggagcttgtg cctctgctgt ggacggtggt   6480
aagggagctg ccactacgaa ccacattgtt tctcttttac attataataa ggtctaatgt   6540
ttacagagaa attttgtgct agccctggtg ctaaaaacct tctagccttc tcatattatc   6600
tgcctgttga gatagggct attgtcatcc ccatttaaa gatgatgaaa ttgaggctca   6660
gagaggtgaa gtgacttgcc caaagccaca cagctcgtaa gggagggct gttgtttgaa   6720 cccgagtctg cctccagagc ttgagggctt caccctcta cgcattgcct gcatcatgac   6780
tcctggaatc cctgaaagga cttcggaatt ctaaggcact ggagctggtg gtttcactgc   6840
ctcagtcttg caggggaact caaggacctg agaagtaaag cacttatcc cggggtatag   6900 gcaggggcag gggcatcctc cacacgcctg gccacccag ggctgcttgg catcttcact   6960
tccccttggc gctcaccaca ccattatctc ctatctttc ttcccaccc accactccgg   7020 gagaggtgca gagaaaactg ggacttatca agacaaagaa caaagtcgt ggaggaaga   7080 agccaagagc catctctact ctggggtagg gccttcagt tttgcccctt tgaaatttca   7140
```

```
aattccagtt tgtggacaaa gtcctaacta tctcacaata taggtcccca accactgacc    7200
aaactccagt ccaggcagcc accagctggc ctggtcttgc tgcttccttt agcggcttcc    7260
aaggtccagg gacaggsggt ctgggccacc aagaggctct gctaggctgt ccctgcagcc    7320
acagccaccc cactggaccc ctgcctccca tctgagagga cagccctctt cctggagctg    7380
ggatctgaca cttgctgata ccaacggcag ataccaggta ggtcccctcc ctttctcttc    7440
cttgagctcc taaaatgcca ctcataccac cctctgcact cggcaaaggc cactgtggct    7500
taatcaaatc aggcacccac aaagcttcaa gactggaaaa gatgccttgg ctaacccacc    7560
catttagtgg acgaaacac tgaggccgtc aggggagtgg cagctggcca cagactgaac    7620
catagacttg gggcccagac ctggggcccc tcacggagcc tcagagggtg aaagggactt    7680
gctcaagtcc acgcagcggt ggtgggtgag ctttgtctta caacgagca ctttctactt    7740 catcacagac catgagtggc attgtgtttg ttcacccgat gatgggtggc cactggcttg    7800
ttcacccgat gatgggtggc cactggcttg tcacaggagt atttccgaga ggaagatgag    7860
ggagcttggg gctgaaggcc agtgggtttg aaggaagca acattcatgt ggttaactga    7920
taactgggcc ccatccctgg gcctccttcc tccctccctg tccttagcct gattaagacc    7980
aacttaccca gctgctaatc attgctgagc ctgttgattt tgccttaaaa aattaactgg    8040
gcatgagttt gcggttttcc tcacccctaa ccctgaaaag gctgggtgg caggaggcc    8100 tccagggtta tgcaagaggc cgctggcctc ccaacgcata gcccacggcc acctcggctg    8160
ctctccaaag aagaggcttt gctcaagagt caacagtctg cttgttcccc ctgtgctggg    8220
tcctgagcaa atttgctctg ttaccaaaga gagataaagg cagctggggg agagctttcc    8280
aaacagggat gggaagcggc agctttgagc ttggggttct agaactctgc agtgtcagag    8340
ccaggagaat ctttaggagg atgtgggctg gggttttca agctgggttc cgaggctccc    8400
aggagccaag ggtatgcatc cacaggccca gcttcaacca gcgactccct tttacatgta    8460
gtcttaatat tttatttgag ggttggaaaa ccactgattc agccccatcc cctcattgca    8520
cagatgggga gatggagatc agaggggaa gtgacttgtc caaggacaga aggtcacctc    8580
gggtattcag gggctccagc cagcatggga atgaatggtg ggctctctgt ggacccgggc    8640
aatgtcttga agacattgg tgaacaagac ggctctgcaa acgccttgcc atgccgttct    8700 cccctcctc ccagggctgg ctggaagcag agaggtgcct gagagccatt ggaagaccca    8760
agtcagggga atgcacctgg ctctgtgtcc catgggccct gtgaggatat gaccagcagc    8820
caggcactgc aaaccggaga ctacgttata atccatctca gccacgtcct gtctctggag    8880
gcatcagcac tttgggaggc tgagatggga ggattacttg agcccaagag tttgagacca    8940
gcctgggcaa catagtgaga ccctgtgtct attttttaaa aagatttttt aaaattaaag    9000
acagatgccc agtccctatc acaaaaaaag atgtagagcc ctgccctgac tctctccacc    9060
tctctgagcc tcagtttctt cacctgtaaa ttgggaatta taatacttaa cttccagggt    9120
tgtcatgaaa atgaaatgaa gcaaaatata cacattgatc atcatggcca ctggatatgc    9180
agctgtttta ggagctttgc atgtgttact tccttgatcc tcccagccac tctgggaggt    9240
aggcaatgtt ttcaccaatt ttttacacac cagaggcaca gggaggttga gccatatacc    9300
catgctcaca cagctgatga gaaacaagaa gtggaattgg aacttgggca gtctgtctct    9360
agagtctgtg cctctaactc cagggctacc cttcccttcc agggatgcca gtgagagatg    9420
gccaggagaa gggcagagag cagggcactg tgggagatgc tgactgtaag gctccggagg    9480
```

```
tagggcagag agtatggtct ggagaatgat caggaaggaa gccaggagga cttggatctg    9540
tgtgggtgga gcttctccgc aggctgcctc ctgccaggtg gcttatgaca tctgggctga    9600
gggtgttgct gtcctcctgt ttatgttcat ccctcctgtt tatgttcctg aatttatctg    9660
cagggggtgac cttgggaatt agatgcggcc ttcccggccc ttgtggggcc tgaaggctga   9720
tgggagcccc tgcctgaccc agactctggt ttggggagtg agggctgagc ccacatccca    9780
gaagccaccc ttggtctccc catactcttg ttctgagggg ccccagggat ttgccaggtc    9840
actaaggtga agtgtttgga agtcctgagg ctcagatcag agttactgcc ctgtacagtt    9900
gtgcaggttg ctcactgcac aaaggttctc cagccaagag ggcaggtagg gatgaaaacc    9960
cagcccttgt tccacttgcc aagcgaagtg cccatggagc tctgcctgcc cagagtgggg   10020
tgccttttc ttatttgccc tagggcttca tgtaagctgc tgggtgtcct gccccagctc    10080
tggttccagc cactgtgtgt ccttgggcaa ggtcatttcc ctccctggcc ttggtttccc   10140
attggagaag ttttgtctaa caaagcagag actcatctct gaagatgaaa tagaatcatc    10200
tgaaaccttt aaaatataca gatgttggcc gaacatggtg gcttacacct ataatcctag   10260
cactttggga ggctgagatg ggaggtttac ttgaacccag gagtttgaga ccagcctggg   10320
caacatagtg agaccctatg tctatttttt aaaaagatt tttaaaatta agacagatg    10380
cccagtccct atcacagatc aatgatcgaa tcttggggta ggggtgggga ggtgccaggc   10440
gtctatattt ttgtgcagcc aatattgaga cccactgtag gggggcttca aatttgaacc   10500
tggaaagcct tcgatggcat caagttctat cacttactac aacttactag tcaaaacctc   10560
agcgaggctc agttttccca tctgtaaaga gggaatgatg atcgtttcct cacaaaatca   10620
aaatgccaat taaatgagat aatgttcaga cagtgcttgg caccatgttc cccaagtagg   10680
gagctcctga ttcttgctac caagactatt attgttgtta tgggcaattt gacgttgaca   10740
aaataagggg cctttctagg tcaaggattc ggtgacttga agacaggcct cctctgttgc   10800
tttgagtcaa tttctagtac ctgggcctaa atcttgactg cacaccggtc atattattga   10860
ggtatgtgtt attattatta tttaatattt tacttaattt gtgaacatct ttacatttag   10920
ttttgaattg gtgctacatt cgcatggttc agaatcaaaa cataaaaggt gtaaattgag   10980
aagtcttgct tccagctgtc tcctgttcac ctgttctcct tgacttcctc actatgggga   11040
accacatccc ttacagatgt atctgccaag gtttctttat acagaccaga tagcatgtaa   11100
gatcatacat gagtagcctc tgctcttaca ctgttctgta tcttgtttgg ttcatttaat   11160
atcacaacct ggagatgctt ccatagcagc tgagagcaag ctttgaggat ggaagggttc   11220
tcgtctccca tcacaggtga ggaaactgag gctcagagaa gaaacatcat tttcccagtg   11280
agccaaggca atggtgttag aactatctct acctggctcc agagcttgtg tttatgcccc   11340
tgcaccgata cggccttcca tgaagcccgg cccagaaagc tttggagtct ggttacatct   11400
ctgccatgca ggcctggcct tcccaggaca agaggtgagg aggggggctg tcggggtcct   11460
cactgtgtct ggactcagaa atcccaaaga gaggatgaag tgtagaacaa agaatgtccc   11520
aagtcatcca gatagggacc cagtgggaag gtgtcccctg gatggaatag tggggcctg    11580
gtggctgtgc ccgtcagcac tggagaacct gccaggaact ctctgccagc tcaggtggt    11640
gcgggtggca ggggaagtca ggaggaggat gagaggcagg gagggaagca tggccgatga   11700
gacaagctct gggtgagggg atggagggga cccatgcct ggagctcagg aaggaggatt    11760
tggagttcaa ggcagaagtg gcaatgagat tttaaccgat tgtttctgc tcagggaact    11820
tcagggttcc ctctggattc ttgacctgct tcagtttgct gactcactgg ctttgggcaa   11880
```

```
gtcattttcc ctctccgtgc ctcagtttcc ccaactgcaa aatgagagag ataagagatc   11940
tggtctttag gcagccttgg actacccta atactctacg gggctcctct caccttgttg    12000
aggtcgtctg gattctcctt ctctgattgg aacgtcattc acccatcagg gccatggacg   12060
ttcctgggtt aggggatgag ggtacaaatc ctccacactg ctcccagtct ggaatcctcc   12120
cccttggttc tgtgtctctc tcctaccatc ccatccttcc ttccaggcag atgtggagtc   12180
aggaccatac ctggtgggtc ctgggggaag ccctggcccc agtccgacat cctcctcctg   12240
ctgctatggg gtcccgcaca gtgcacaacc tcttcatcct tgagggagct cctgctggcc   12300
cctctcagca ccccagaccc tgcgagggcc gctgggcaga gttaatccct taatactggt   12360
cacaatgaga tttcagggat ggtgggaggc ggtctccatg gaaactgcag acctgtccag   12420
gatccatgca aggaattagc cccagggctc tgcaaggggc tcctagagag ccaaccccaa   12480
taggaatggg agacacagtg gtctggactc ctgggtcctg ctctggccct cctgttgtct   12540
ctctggaggg cttggaaaaa accataactc ttgcattgct tcagtattct gctcaactgg   12600
acagagccat attcacaggg agagccctat caccttctg agcgtgtttc tccatccccc    12660
tattggcatt gtaatcctta acccagtggc ttttctagaa gagtgcaggc ttcagagtct   12720
gccagacctg agcttgaagc tcagcttttc cctccacgac tgtaaactta gccgaggcat   12780
ttcacttctc tgagcctcag cttcctcatc tgtatgatgg gcacaataat agcaacatgg   12840
catccctctt gtgctggctg gtgggtagta acatccagtg aatgtgagtc tccttctcac   12900
cttttcctga ctgccacgcc cacactgcac atttgccctc cccagccccc tgcagcttcc   12960 agaacccgt ggtctcaagc agagagctgt cgcacttcct tctttgcctt ctcatcctcc    13020
aagtcccatc ttagtcatct tcctccggga aacagaacgc cggggtcctc ctctgtcccc   13080
ccatagcccc caaagcttta catcatcatc gtttagtcag atggtaatta gactggttgt   13140
gtgcctcctc cactggactg tgtcccatct accattgtat tcccaggacc cacttgatat   13200
aaataggctg gatgaataac tgagtgaata aaggatggaa atcgtccatc gaaacagtca   13260
acatttattc agcaccttct gcgtgcatcg ttgtgggtgg tggagatgca gcagggaaga   13320
ccatgggcaa aatatccccc tcagaggggt gcagatgagc aaataaaaat acaggatgcc   13380
cagtcaaatg tgaatttaag atacacaaga aatacttcgt tagtatgagc gtgtcccaaa   13440
taatgcatgg gacctgctta tacttttaaa ctgtggtgtt catctgacac tcatatgaaa   13500
ctgggtgtcc tgtgttgtgt cgggcaaccc tacaccctcc ctcacagagc ttgcgttttg   13560
gtggagaggc gggttgcaga cataagcaag taaatacatg aaaaacgaag tcaattacaa   13620
acagtggtta agtgcagtga agacgcacag cgcgatgtga tagcacctgg ggatgggcag   13680
gacgatcccc tgagctagtg gcctttgcct gcacaggtca ttttagctcc aatgagatgc   13740
cactttgcaa aagttcttg aggatcttaa agggcacggt ggaggctgct aaacttgaga    13800
gaaggactct gaggagggca aggggcgcac ctgagggagt ggggctgcta agtctcactt   13860
gatagactcc acagttttgc aacttggatc tgggccttca caaaccttcg cgaacccgca   13920
gccccacccc tcgggtcagc caatgtcttc tgtggggctg ggagccaggg gaagaggcca   13980
aaggaactgt gcagagaagc gtggccaccc gggccgcagc tggagccct gacacccttt    14040 gccgcccac ctcatcccgc ggttgcccca gggcgcaggg cagggcaggc accgcgctgg    14100
gccggagggc gtcccggagg aggcggccaa gactctccgc agtgctgcgc tttgcgcttc   14160
ctgggctcct cctcgtggcc aacgcaggaa ctggtgttca gaaacttaga tagccttagg   14220
```

```
gacttcacca atcacagcaa tcccgccaat cacaggccca gacgcactat gtctctccaa    14280
atccagagga ggcctgctcg gttcgatcac caatcacagc tcgttggatt tagttaccta    14340
aaagaacatc tccccatcac acaccagcac atggccacgg cagcaatcag aacgtaagat    14400
tttaaaacca gttcccaggg tagcagccgc tgcccttcca ccacctacta aacttctgtt    14460
cccagcacct tgttccaatg tacggggtg ggggggtct ttgaggaagg ttccaggctt      14520
tgtgctgctt ccatgtggaa gcagatgtta gcatgtatgg ggcatgtata atgatattac    14580
tatcagtaaa tgtcatacccc attatgaaaa ttaagatagg cagggcgtga tggtgcatgc   14640
ctgtaactcc agctttaggt ggccaaggtg ggaggatcgc tggatcccag gagttggagg    14700
ctgcagtgag ccacgatggc gccactgcac tccagcctgg gtgatagagt gagactctgt    14760
ctcaatttaa aaaaaaaat taatgtgtgg atataggagt gtggaaaaat tataaccttt     14820
gggttagaca cacctggagc ccatatacta tctttgtgaa gtaggacgac tcacctcccc    14880
ttcctcagtc gtcaaaagag aatgatagtc atatctacat gtcatatatc atcacccacc   14940
ttctctcaat tattcaagcc aacatcttgc aagtcacaat ctttgtgttg tgtttctcat    15000
gccttccagt tcatcagaaa atccagttct tgccacccctc caaacagaat ctagattttc   15060 catcttttcca tctccacccc agccaacctt atgcatcatc tctggaggtc tgcaaaagtc  15120
ttttcacttc ttcccttttt ttttttttaa acctgccagg gttggggagg ggatctcccc   15180
cgctccaccg ccccccccgc ctccccccc ccccgcctgc ctccacccca cccccttcact   15240 ttttctcctg tggcttccct accccctact cttcactcag gggccaaggg tgatcttgta   15300
caaatgtaca ttggctcaga tcctcttcta cttaaatttt tatgacttcc tatgcattta   15360
taacaaaact catacaactc ccacttaaca ctgtgaggcc atgcacgccc ttgtttttat   15420
atccctccgt gtccaacctc atttcattcc acttgccccc accccctatca gcagcaggca  15480 tactagccat tttaaagttt ttcttttcctg tcttggggggc ctttgcatat actttcccct 15540
ctgcctggaa tacttctttt tttttttttt ttttttttt taagatgaag tttcgctctt    15600
gtcactcagg ctggagagca atggcacgat ctcggcttgc tgcaacctcc gcctcccagg   15660
ttcaagcaat tctcctgcct cagcctcctg agtagctggg atccacaccc agctaatttt   15720
ttaattttta gtagagacgg ggtttcgcca tgttggccag gctgatctca aactcctgac   15780
ctcaggtgat ccacccacct cggcctccca gagtgctggg attacaggca tgagccacca   15840
cacctggcct ggaatacatt ttagtaagtg tttaatggat agttgttgga tgaatgactg   15900
aaaaggtctt tcaagaggaa ctgatagtga tgtaaacttc aagtgctcgg tgcgtaacag   15960
gtattcaatg aaaaggattc tatgcatata gtagaaattt tggaaaataa aataaaaatt   16020
gaagatttaa aaatcgtatg tgctccaaca tttagaaagg ttcaaactct taatggctaa   16080
ccagggtttc ttgacctaag cactaatgac atttgggcta gagaattctt tgtcgtgggg   16140
actgtcctgt acattgtccc tggcagcatg tctggcctct agccactaga tgtcagcagc   16200 acttttcccct accctcaagg tgtgataatc aaaactatct ccagacattt ataaatgtcc   16260
cttgggggtt gaaattatct ccactgagaa ccactgtgct gggcttctac ccttacaaga   16320 aatttttctct cagtcattca atgcttctca aatcttggtg tccataagaa tcatctgggg   16380
ccattattaa aaattcagat ggcagctggg cgaggtggct tacacctgta atcccagcac    16440 ttcggggaggc tgaggcaggt ggaccacttg agttcaggag ttcgagacca gcctgccaaa   16500
catggtgaga cctcgtctct actaaaaata caaaattagc cgagcgtggt agcacatgcc     16560
tgtaatccca gctacttggg aggctgagac aggaaaatca cttaaaccca tgaggcagag    16620
```

```
gttgtggtga gccgggatcg tgccattgca ctccagcctg gttaacaaga gcaaaactct   16680
gtctcaaaaa aaaaaaaaaa aaaaaaaaaa tcagatggtg gctgggcacg gtggctcacg   16740
cctgtaatcc cagcactttg ggaggtgggt ggatcacctg agttcaggag ttcaagacca   16800
gcctggccaa catggtgaaa ccctgtctct attaaaaaaa aaattagcca ggcgtgatgg   16860
tgcatgcctg taatcccagc tactcgggag gctgaagcag gagaatcgct tgaacctggg   16920
aggtggaggt tccagtgagt gaagatcgtg ccactgcact ccagcctggg cgccagagcg   16980
agaccctgcc ttaaaaaaaa caacaaaaaa aatcagatgc ctggggtcct acctccaggt   17040
gccaggacca acagtgggcc tagtcatcag attaaaaaaa agaaaatatt taataaatag   17100
aggtggggca tggtggctca tgcctgtaat cccaacactt tgggaggcca aggcaggtgg   17160
atcactggag actaagaatt caagaccagc ctggccaaca tggtgaaacc ttgtctctac   17220
taaaagtaca aaaactagct gggtgtggtg gtgcatgcct gtaatttcag ctacttggga   17280 ggctgggca ggagaattgc ttgaacctgg gaggcggagg ttgcagtgag aagagatcag   17340
gccactacac tccagcctgg gcgacagagt gagagtccat aaattaataa acaaacaaat   17400
taattaatta aaaatagag acggggggag gtgtcttgct atgttgtcca ggcttgtctt   17460 gaacccagc ctcaagcaaa tcagcctccc aaagtgctgg gattaaaggc aggagccatg   17520
gagcacctgg cccaagtgtt taatgagctt ctgggcactt ctgataccag gtgccctcag   17580
accgcacttt gaaaactcct caaggaggcc tctcaatcac ctgatcacca aaccctgtgt   17640
gaggctccct acccacctgg accctctcct tgaattcctc tcctttccaa ttattaccct   17700
tccctagata gcaagtggtg acagaaccaa accctagctc agccaaagcc caaattgcct   17760
catctccctt cagggaatag gcaaaaaaaa aaaaaaaaaa aaaaaaaaaa gatcacagag   17820
ttcagctgaa accacttagg aaatatcagc atccccacct ccccacccaa aaggactcct   17880
gagtggcagc ctgagaggtg tgtctgctca tcagaataat gttgtcagac tgtgttcttt   17940
ctgggggatc atcacactcc cttttctggg aacaaatgtt ggccacttgg tgggatgggc   18000
catcatgatc tacgtcagac aaattcagtg agtcatgact cagcctatct ctctagaccc   18060
atcttttatg cccccttact tatagtctct ctgagggctg ttctcaacta ttctatttct   18120
ctcctttccg gcacatgatg gggattacat tttcttgctt cctttgaaat gagatgtgac   18180
catgttactt gtttcaggta acgagatgtg agcagaaaca acctgtgtca cacctgggca   18240
gaagctttaa aggccagtgc tgcccttgtt ggggaagcaa gtatagatat gaatcgttcc   18300
acaacgcgga gcgcccctg ccgacccatg ctgggcgtgt actataggtg agcaattaac   18360
tttgctgttc aaaccattga acttaggggg tttttttgtg gttgcaagct aacttcactt   18420
cacttgactg aacacagtct ttccaaagtt tcactaattt tttaatgacc attatgattt   18480
tttcatatct gtaacatttt tcttacatca actcacttct ttttacttca atttattta   18540 gaaagaaata ttattactac caaatgaaac agtatcataa gtagaaagca atgagaaaat   18600
aaacagaatg aaagaaatcc tgatatcaaa tcctgactta atactatttg cctttcaaag   18660
cctctggacc tttggtcttt atttaaaaaa aaaaaaaaaa aaaaaaaaaa ggagccaggg   18720
gccaggcgtg atggctcaca cctgtaatcc caggaatttg ggaggccgag gtgggaagat   18780
cacctgaggt caggagttcg agaccagcct gaccaatatg aggaaacccc atctctacta   18840
aaaatacaaa aattagccgg gtgtggtggc atgtgcctgt aatcccagct actcaggagg   18900
ctgagacagg agaattgctt gaacctggga ggcggaggtt gcagtgagcc gagatcgctc   18960
```

```
cattgcactc cagcctgggc aacaagagtg aaactccgtc ttaaaaaaaa aatgggagcc   19020
aggtgcggtg gctcatgcct gtaatcccag cagtttgggg ggctgaggtg ggcagatcac   19080
ttgaggtcag gagttcaaga ccaccctagc caacatggtg atatcctgtc tctacttaaa   19140
atgcaaaaat tagctgggca tgatggcatg tgcctgtaat atcccagcct cttgggaggc   19200
tgaggcagga gaatcacttg aacccaggag gcggaggttg cagtgagctg agattgtacc   19260
actgcactcc agcctggggg agagagttga gactccgtat ttaaaaaaaa aaaaaaaaaa   19320
gaggtcccca agagtacttc tcaatctttt ggatccccaa agctgtctaa gattgtcaga   19380
atatttgaag gcagcacagt attgaggctg agtgtaccaa ttctggaact tgacatcctg   19440
ggcttaaatt ctggttcagt catggactag ctgtgtgacc ctggacaagt tactgaactg   19500
ctctgtgact gttttcttat ttgcaaaata gtgaccataa tgatgtgtat ggcattaggt   19560
cgtggtgggg attatttgtg ttaatgtata aaaagggctt agaagtgtgc ctggcactta   19620
gtgagtgcta tggaggcatt acctataaaa tgatggcagg atccagatcc aaatagattt   19680
ggtgaattat tgtttgtttt ttttgagaca gggtctctgt cactcaggct ggagtgcagt   19740
ggcgccatca cagctcactg cagcctccaa gtctccaggc tcagatgatc ctcctacctc   19800
agcctccaga gtagctggga ctacatgtgt ggaccaccac ccctggctaa ttttctata   19860
ttttgtagat atgggatttc accatgttgc ccaggctggt ctggaactct tgggttcaag   19920
caatctgccc cttcttagtc ttcaaagtgt tgggattaca gacgtgagtc acccccaccca   19980
gcctggagaa atgtttgaac tccatggaga taagtaaaaa atcctctgca ttggttaaaa   20040
ataaatcacc tggatgattt atttatttag tgtagatggg aaaagctacc ttagcagaaa   20100
gtgacatagc aaaattctag aggttttact tggtggcagc tgcccaaacc tctaacccag   20160
tcgtatgtat cattagagag aatgtagttc ccaggtcaga ggagctaaga ggtccttggc   20220
attctactcc taaggagcat atatggacaa ttgtgtttag ttttcatttt aatatgaata   20280
cttaaaattt tcctaggatg gcagaggatg agaaagctat gccccttagg ccagtgcag   20340
cggcatggct catgcctgta atcctggcgc tttgggaggc caaggcgggc ggatcacgag   20400
gtcaagagat cgagatcatg ttggccaaca tggtgaaact ccatctctac taaaaataca   20460
aaaattagcc ttgcgtagtg gtacgcacct gtagtcccag ctacttggga ggctgaggca   20520
ggagaattgc ttgaacctgg gaggcggagg gtgcagtgag ccgagatctc gccaccgcac   20580
tctagcccgg cagcagagcg agagttcgtc tcaaaaaaaa aaagaaaga aagaaagaaa   20640
gaaagctatg cccccttgaag aataatcaaa gatccaaaag agttttgggc tgggtattgg   20700
agaagaggag agaaaggtgg tgtagcagag tggtcagggc cattgccttt gaaatatcag   20760
tggtgccatt tacatagctg ttggaccttg ctaaaatcat aagctcttca agccttattt   20820
gcttcatcta taaaatagga atcaatgata ggaccttttc atagattgct ttgtggagta   20880
aatgtgttaa accttataaa cctggcaggt agctgcccag catatagttg cgttatttac   20940
tcaattcaaa gtactttcct gccgggtgcg gtggctcagg cctgtaatcc cagcactttg   21000
ggaggctgag gtgggtggat cacttgaggt caggagttcc agaccagcct gaccaacatg   21060
gtgaaaccct gtctctacta aaaacacaaa aattagccgg gcgtggtggc agtcacctgt   21120
aatcccagct acttgggagg ctgaggcaca agaatcactt gaacctggga ggcagaggtt   21180
gcaatgagct gagatcgtgc cgctgcacgc catcctgggt gatagattga gactcagtct   21240
caaaaaaaag gcaacaaagt actttccttt ggaaaagagt gcccactggc tgggtgaagt   21300
ggctcacgcc tgtaatctca gcacttgtgg ggctgaggca ggcagatcag ttgaagccag   21360
```

```
gagtttgaga ccagtttcac gtggccaaca tggtgaaacc ccgtctacta aaaatacaaa    21420
aataagccag atgtggtgtc atgtgcctgt agtcccagct actcaggaga gtgagacagg    21480
agaatcattt gaaccctgga gttggaggtt gcagtgagca gagatcgtgc cactgcactc    21540
cagcctgggt gacagagtaa aactctgtct caaaaaaaaa aaaaaaaaaa gctctcactg    21600
attcctacag cttcagagaa tgaacgagga ccaaaatgtg gatgctacag ggaggaaact    21660
tgaggctcaa aatggagatc tttctataaa atacaattgt tctaccacag gaaaagctgc    21720
tttattaagt agtgagtatt ccgtcattgg aagtattaag cccaagctaa atggtcaact    21780
gtcagggaag gatggtgaga ggattccagt gggttagagg tcaaagagcg tctaccaggt    21840
gcaaaagtct taattaacaa agtactatca aaaccaaatt catgtttggg aaactgtata    21900
tccacatgca aaagaatgaa atcagactct ttccttacac catatacgaa aattaactaa    21960
aaatgagttt gacggaaaag tataaaacct ttggaataaa acataaggga aaagcttcat    22020
gatattagat ttggtgatga tttcttggat atgacaccaa aagcacagga aattttttaaa    22080 aattagataa attggactac atcaaaatta gaaaaatttg tgcaccaaag gacacttgac    22140
tgagtgaaaa agcaacttac agaatgggag aaaatatttg ccaatcatat atctgataag    22200
gggttaatgt ccgaaatata taaagaactc ttacaactca ataacaacaa ccaaaaactt    22260
taaaaatgga caaagaggcc aggtgtagtg gctcaagtct gtaatctcac cactttgtga    22320
ggcagaggca ggaggattgc ttgagctcag gagtttaaga ccagcctggg caacatagtg    22380
aaactttgtc tctacagaaa aatttaaaaa ttagccaggc atgctgcaca cctgtagtcc    22440
cagcttactt gggaggccga ggtgggagga ccacttgagt caaggagttt gaggctgtgg    22500
tgagccacga tcctgctgct gcactctagc ctgggtgaca gagcaagacc tgtctcaaga    22560
aaacaaaaaa attggcaaag gacttgaata ggcatttctc caaggaagat atacaaataa    22620
ccattaagca cataaaaaga tacttaacat cactaatcat tagggaagtg caaatcaaaa    22680
ctgcaataag aggctgggca cagtggctca tgcctgtaat cccagcactt tgggaggcca    22740
gggcaagtgg atcacttgag gtcaggagtt tgagaccagc ctggccaaca tggcaaaatc    22800
ccaaatctac taaacaatat aaaaattatc tgggtgtggg ccaggcacag tggctcacgc    22860
ctgtaatccc agcactttgg gaggccaagg cgggcggatc acgaggtcag gagttcaaga    22920
ccagcctggc cagcatggtg aaaccccatc tctactaaaa atacaaaaat tagccgggca    22980
tggtggcatg catctgtaat cccagctact caggaggctg aggtaggaga atcgcttgaa    23040
cctgggaggc agaggttgca gtgagccaag atcgcgccac tgcacccccag tctgtgccac    23100 acagtgagac tctgtctcaa aaaaaaaaaa aaaaaaaag gaaaagaaaa attatccggg    23160
tgtgatggca catgcctgta atctcagcta cctgggaggc tgaagcagga gaatcgcttg    23220
aaccctggag gagaagtttg cagtgagctg agactgcact actgcactcc agcctgggcg    23280
acagagcaag actatgtctc aaaaaaaaac caagacaaac aaacaaacaa acacacaat    23340 aagagaccac ctcacaccca ttaggatgga tattataaaa caacaacaaa acagacaata    23400
gtaagtgttg gtgaagatgt ggagaaattg taaccctttt acgttcctat cactgctggt    23460
gggaacgtaa aatagtgcag cttctgtggc aagcagtatg cggcttcct aaaaaatgaa    23520 aaatagaact atcatatgat ctagcaattg tactcccgag tatatacccca aagaaccaa    23580 aagtagcatc tggaagagag atttgtatac tcaagttcat agcagcatta ttctataatag    23640 ccaaaaggta caggcaaccc aagtgtcaat caatggatga atggatcaat aaaatgtggt    23700
```

```
atatgcatac aatggaatat tattcagcct taaaaaggat ggaaattctg acacatgcta   23760
caacatggat ggatcctgag ggcattatgc taggggaaaa gctagtcaca aagaacaaat   23820
actgtatgat tccactagcc tacaggaaag tagtcaaatt cacagagaca gaaagtagaa   23880 gggggtttgcc agggcctggg aagaaaggag aactattttc ttttcttttc ttttcttttt   23940
tttttttttt tgagacgggg tctctctctg tggcccaggc tggagtgcag tggtgcgatc   24000
tcggctcact gcaacctcca cttcccgggt tcaagcgagt ctcctgcctc agcctcctga   24060
gtacctggga ttacaggcac gcaccaccac gcccggctaa ttttttttgta ttttttagtat   24120 ttatttttgta tttttagtag agacgaggtt tctccatgtt agcctcccaa ggggagctat   24180
tttctaatgg gtacagtttc agtgtgggaa gatgaaaaaa gttcaggtga tggatggtgc   24240
tgatggttgt attacaatgt gaatatattt aatgtctctg aactgtacgt ttaaaaatgg   24300
tcggctgggc gtggtggctc acacctgtaa tcccagcact ttgggaggct gaggtggatg   24360
gatcaccttt ggtcaggtgt tcaagaccag cctgggcaac atagtgaaac cctgtctcta   24420
ctaaaaatac aaaaatcagc tgggtgcggc ggtgcatgcc tgtaacccca gctactcggg   24480
aggctgaggc agaaaaatca cttgaacctg ggaggtggag gttgtagtga gccgagatca   24540
cgccactgca ctccagccgg gcgacagagt aagactctgt ttcaaaaaaa aaaaaaaata   24600
catgcataaa agatgtttct aagagtgcta aaaaatgcct acaaattgat aaggaaaggt   24660
aaataataca atagataaat ggtcaaagga tacaaacaag cacactcata atgtaggaag   24720
ctcaaatggc aaaagagcct ctccttctct agtaatagag gaaatgtaaa tttgaaagtg   24780
aagcataatt ttcacattcag tatcttacaa aatcaagtgc tgatgaggtt gtagagcaac   24840
caaaactctg taactattgt tggaagtgga agttggcatt caagaatgag caatttagca   24900
acatctctta aaagtgttga tatccactgt ctaagataca gaaattccat ctctgcatgt   24960
tacctagaga aactctcatc cacaggtata agaatagtct ttggagcatc atctgagata   25020
gtgagccaag atcgtgcaac tgcactccag cctgagtaac agagtgagac tccatctcaa   25080
aacaaacaaa taaacaaaac agaataaata tactcaggat atttacagac acttttattt   25140 tatttttgt tatttcaact ttgttttttt tacctgcctc ccaggtttaa gcgattctca   25200
tgcctcagcc tcccaagtgg ctgggattac aggtgcccac caccaggcct ggttaatttt   25260
tatattttca atagagatag ggtttcacca tgttgcccag gcttgtctcg aactcctgat   25320
ctcaagtgat ccacccgcct cggcctccca aagtgcttgg attacaggca tgagctaccg   25380
cgcccggctg catgtgtttt taaacattgc ctggcccgtt atttcaactt ttattttcga   25440
atcaggaggt acacgtatag gtttgttaca aaggtatatt gcatgatgct gggggtttcca   25500 gtatgaatga attcatcacc caggtaatga gcatggtacc caataggtag ttttcaaca   25560 tttgccccct ccctctctaa cccctttggt ttctccagtg cctattgttc ccatctttat   25620
gtccatgtgt acccaaggtt tagccccac gtataggtga aacatatgt tatttgaatt   25680 tctgtttctg cattagtttg cttcggataa tggtttccag ccatatccat gttgctgcag   25740
aggacatgat ttcattcttt tttatgactg tatagtactt catggataca cagcatttta   25800
tctattttat ttcttttta ttttattttt tgatagagac agggtttcac catgttgccc   25860
aggctggctc ttgaactcct gggcttaagt gatctacttg cctcggcctc ccaaagtgtt   25920
ggaattacag gtgagccact gcacccagcc tacacagcat tttaaatgag tggtctggtg   25980
caacttgtat catcatgaaa agatccgaga acctattatg aggagtaata aaaggaagtt   26040
gctgcaggat atgtacagta tatcatttaa ataaattttc cagataagca aaatattta   26100
```

```
ctttgcttat atagccacgt atggtagaac tgtgaaaatg tgtctggtaa tgacacatta   26160
ccagataaat accaaataca catgataaat accaaatggt gaccatgatc accactgata   26220
agggtggcag ggtgatggga tcaggaagac aaggggcttc aactctaagt gtaatgttta   26280
atttgtcatt aaaacaaaca aacaaacaaa caacatccaa agaaaacatg gtcatgtagt   26340
aagatttgac aaaattgaga ggtggataca taaatgttca taatattatt ctctatactt   26400
ctctgcatat ttgtaatatt tcttacttta aaaaaggag aaatgagatt ataaaaaaaa   26460
gtcaaccatc ttcctacata ccagcgacag acaatttggt agtataattt taaaaatcat   26520
acaatttgca caatgacaac aatttgcaca atgacaagca accgtggata aaaatctaga   26580
aatctatata tatattttt tctttgagac agagtctcag tctgttgccc aggctggagt   26640
gcagtggcat gatctcggct cactgcaacc tctgcctccc gggttgaagc aattctcctg   26700
cctcagcctc ctgagtagct aggattacag gtgcatgcca ccatgcccgg ctaattacca   26760
tgcccggcta atttttttg tatttttagt agagacagag tttcatcatg ttggtcaggc   26820
tgatctcaaa ctcttaacct cgtgatccgc ctgcctcaac ctcccaaagt gctgggatta   26880
caggcatgag ccaccatgcc cggccctaga atcctatttt ttaaaagcaa ctaggagtat   26940
atctaagata tagcatttct ctgtctgaga gcagggagag cttgcatagg tgtcaatgtc   27000
cttcaaggga ctcttgaaac taattcaggg ccctatacac tgcaggcatt tcttggagtg   27060
gccaaggtat tgtcatgtgt taagaattct gagaagttct cggataatga aatttgtgca   27120 gctttctttta attcagcagt tttcaaacat ctaacaatag aatccttctt gtctgagggg   27180
cctcgcctta ggaaaggctg ccctaacaac ctcaaagttc ccttccaaca cccacagtcc   27240
accattctag tcttggctct gccactaact tactgtatga ctttggccga atcacctttc   27300 ctcttgggt ctcagtttgt taagttatta acaccctggg tgacagagca agaccctgtc   27360
tcaaaaaaaa aaaacaaaaa catttccctg gcaaaaatt tatgactaaa tcctccaaag   27420
caatcgcaac aaaaccaaaa attgacaagt gacacctaat taaactaaag agcctctaca   27480
cagcaaaaga aactatcaac agagtaaaca ggcaacctac agaatgggag aaaatatttg   27540
cgaactctga atccaacaaa ggtctacaag gaacttagca attctacaag gagctagaac   27600
ctacaaggaa cttaaacaat tcaacaagca aaaacaaag aaccccaaca aaagtggat   27660 agagcacatg aacagacact tctcaaaaga agatgtacaa gcggccaaca aagatgaaaa   27720
aatgttcaac atcactaatc atcagagaaa tgcaaatgaa atcgtgagat accatctcac   27780
actagtcaaa atgattatta agtttctttt tttgtcccca cccttgatat ctgaagaatg   27840
gctgtcatta aaagtcaaa aaataacag atgttggcaa ggctgtggaa aaagggaac   27900 acttatacac tgttggtggg aatataaatt agttcagcca ctgtgaaaag ctatttggag   27960
atttctcaaa gaacttaaaa cagaaccacc attcaattta gcaatttcat gatttggtat   28020
ataaccaaag gaaatgaat tcttctacca aaagacaca tgcacttata tgttctacac   28080
agcactattc acaatagaaa gacatcagcc aagcacagtg gctcacgcct gtaatcctag   28140
cactttggga ggccgaggcg ggcggatcac ctgaggtcag gagttcgaga ccaacctggc   28200
taacatggta aaactgtgtc tctactaaaa atacaaaaat tagccaggca tggtggcaca   28260
tgcctgtaat cccagctact tgggaggctg agacaggaga atggcttgaa cctgggaggc   28320
agaggttgca gtgagctgag attgcgccac tgcactccag cctgggtgac agagtgagac   28380
tccatctcaa acaaaacaaa acagtagaaa gacatggaat caacctaagt gcccatcagc   28440
```

```
agtggaatgg ataatgaaaa tgtggtacat atacactatg gaatagtatg cagccataaa    28500
agggaacaaa acctcaacca agttcaagga cagtgtcaaa aaaataaaaa agggaacaaa    28560
gtcgtgtcct ttgccacacc aggaatggag ctggaggacc tcatcctaag tgaatcaaca    28620
cagaaacaaa aaaacaaata ctgcatgttc tcacttgtaa aaggaagcta acattgggt     28680 acacgttgac atcaagagag gaacaataga cgctgcggac ttctagagga agggcaaggg    28740
ctaaaaaact ctctgttggg tactatgctc actacttggg tgatgagctc aatcatagcc    28800
taaacttcag tgtcacacaa tatacccatg taacaaacct gtacatgtac cccctgaatc    28860
taaaataaaa gtttaattaa ggcctggtgc agtggctcac acctgtaatc ccagcagttt    28920
gggaggctga ggtaggtgga tcaccagagg tcaggagttc gagatcaggc tggccaacat    28980
ggtgaaaccc cacctctact aaaaatacaa aaagaagcca ggcatggtgg tgcgtgcctg    29040
tagttccagc tactcaggag gctgaggcag gagaattgct tgaacccagg aggcggaggt    29100
tgcagtgagc cgagatcatg ccattattct agcctgggca atggagcaag actgtctctg    29160
aaaaaactaa aaagtttaat ttaaaaaaaa aagggtgtgt atagtttgat ctcttacctt    29220
ttcccagcca taacacctca tgttggaccc cacgtttagg ggtttattag gggctttttta   29280 ggggtttggt tttatttctc ctcccccagt taactgtttc ttacttaact aaagcaggtt    29340
catggtagag gaattacaaa aatgcagaga aggatgatta aaaagaatt aaactaggct     29400 gggtgtggtg gctaacacct gtaatcccag tgctttggga ggctgagttg aaggatcat    29460 ttcaggctag gagtttgaga ccagcctggg caacacagta agaccccatc tctacagaaa    29520 atttaaaac ttaaaaaaat taaaaagtaa acgttagaca ggcatggtgg tgtgtgtctg     29580
tagtcccagc tacttgtgag gcttaggcga gaggatggct tgagcccagg aatttgaggc    29640
tgtagtgggt tttgactatg ccactgcact ccagcccggg tgacacagca aaaccctatc    29700
tcttaaaaac aaatcagatt tactccaaat gccacttttg gctctttatg atgacagctg    29760
acatttatag agcctttatg tgcaaagcgc agtggtagga tatctcgttt cacttctcgt    29820
tgaagtggaa gtcaagtcta ttcttatcct tattttacag atgaggagac tgaggatcag    29880
agagataaag tcacctgtcc aaggtcatac tgtggatgta gctctaaccc aagccctccc    29940
gactgcagca caaattctca gccactaccc tattagcccc ttcatttgaa ggtgtcttca    30000
tca                                                                  30003
```

<210> SEQ ID NO 9
<211> LENGTH: 486
<212> TYPE: DNA
<213> ORGANISM: Homo sapiens

<400> SEQUENCE: 9

```
ggactgaagg acagagagaa attgcatgcc tggagtctca ctgctagtac atagaggtgt     60
tatcttcctt tcatctaaca tatttattga gcacctacta tgtaccaggc cttgtgctag    120
actctgggga tatggaaatg agcaaagtag atgtaccccc gaaacttgtg gactaatgga    180
ggagacggac cttaatcaga tcgtcattca aagatactat tacaaactgt tctgagagcc    240
gaggaagcag gaaggagctg tgagagactg agctctaacc ttggccatca aagacaagct    300
gtgcagctct ggttttttga gggcaggaca tggagggtca ggcccagctg gaggcgcacc    360
aaagcccaga gaaattcag aaccacgtga acttgttgga tttcagcccc ttgaagcaca     420
tgttgctatt gcagctgcct tgataactgg ggggacagga ggagcacggc tttcccatct    480
tgtacg                                                               486
```

<210> SEQ ID NO 10
<211> LENGTH: 494
<212> TYPE: DNA
<213> ORGANISM: Homo sapiens

<400> SEQUENCE: 10

```
gtggtgcgcg ccgtggtgcg cgccgtggtg gccgctgccg atgagcgcct ccaccgcgtc    60
ctcgggcgtc aggttgagcg cctcggggtt gaggtgatgc tggtagccgc tcatccagta   120
cagatcctcc agcgccggct tccccgaggt gccccgacg gcgccggggc cccgctcgg    180
cggcccgggg gcgcccccgg cctgagacga gccgccgcc ttttccgcgc cgccgccgcc   240
gccggtgccc gggctgggcg cgcagaagct gggcgaggag ggcacggagg agcagggcgt   300
gctgagcggc gtcgaggaca gcgagcctgg cggcaggcgg tggcagaagc gctcggcctc   360
gggaggctcc ttcttcacct cgaacttcat caggtcgaag tcgttgacgt actcgatggc   420
cagcgggctg ctgggcagct cggcgcccat cgccagctcc gcgggcatcg cccggggccc   480
gcgcccggcc gcgc                                                    494
```

<210> SEQ ID NO 11
<211> LENGTH: 1992
<212> TYPE: DNA
<213> ORGANISM: Homo sapiens

<400> SEQUENCE: 11

```
cggctcccgg ctccgggaaa gaccttctgt tctctgccgg cgcggagggc cgcaggaacc    60
aggcctctcg cctccccacc agctaggcag ggagcgccca tctcctgaaa aattacttcc   120
tgggaagcgg tgcggggaga cagcttcaat tgctttcggt tggtgaaaaa cgaattcgct   180
tctcagattg ctctcctagc tgccaggctc tgacgttgag aggccggctt tcagcctcgc   240
gctggacctt ccacaagtgt ttgcacatga cctggaagac agtcagaggc agaagtccct   300
gcaaatgctc ctggctactt cctgcaggca gctcatgctg ctgcagcaga gacttttcct   360
atgtctagct gccagtattc tgggtgctgg gggcatcctg ttcctaggat cacagccatg   420
gtggtatgtt ctagaactca gaaatttacc aaatcactgg atggaccaga ggagtgagct   480
ccaggttggg tttccagaag ggactcccag aactcttcca ccatacaggc ctctcaggga   540
gctgctccct ctgccatggt cagtgagagg gggaagcagg agccgccatt ggggttgttg   600
agttcgtggc tgcaacccag ggatgaggaa gctgctgcta cacacccatg aagctgatgc   660
ctggacataa atccctactg ataagtgttt acgacatttc cagcgtggtg ccgacactgc   720
atggaaatgc tgcatggaaa gtccttatac atctatcttt gtgcatttat tgtgagcacc   780
tactatgagt aaaacctggg ctggtggctg agaaacatg aagatgagta agagccaatt   840
cctgttcttg gggatttaat aatatattca agggaaaaga cacaaaataa ccatttccag   900
gtaaactctg gtggggaggg tgggaggaga accgtggttt gcttttgtgc ccaacacttc   960
acattcctta cctctttctc cccaccgaga ccttgaggag cagcctgagc cagaggacca  1020
gcatcctcat cttctctcca cctcttacta gggggtggc tttgggccag tttcttacat  1080
tctttgggcc actttagttt ccttattgaa aaatggggat aataatagtg gctacatctc  1140
agtgtgattc tgaggaaacc agaattgtac atgcagagca catgcacaga acagtgcctg  1200
gcacagtcag taattgatca atgtgcgcta ttgttgttgt gtatattagt tctcccctga  1260
tacagatgag agctatctct aactcagaga cttgccacat cattaaatta ggagtgagaa  1320
```

| | |
|---|---|
| ctgagcctgg ataaggaaga ggaacaggaa ttcaacacag tgaacacagc aggaaaggct | 1380 |
| tgtgcgaagg ctctgggctg agatgtgta aagcatgtct ggagatgggg aaggtccatt | 1440 |
| gggccaggaa accacaggct ctgctctcct ggagcagaag cacagcgaaa tcacagccga | 1500 |
| gcagaggagg gcaagggaga gggccgcccc agtctgagag ctgcagggtc tggctggaac | 1560 |
| tgctcccggc cagcggactt cacccgggcg cggggccgc acctgccggg cgcggcctgc | 1620 |
| tctatggcgc cctctgctgt tagtccgccc caggctccgc gccggcctct cctgggtccg | 1680 |
| tggggcctgc gggctgcggg gatcaccgag acccacattc ccgtggccag cagcctttcg | 1740 |
| ctctgctcag aggagaggca gaagggcata ttgctgtttc ccagtcgctt tttacacctg | 1800 |
| ccttcttcgg ataaacccaa aaatcttcct tcagagaaga cggcccgtat ttcccgttat | 1860 |
| ttggggtgg aggtggggct aagggcgtca tagggagagc cttactttca acattctgca | 1920 |
| ttatgaaacc aagggagact ttttttccca acaagtgtga acatttttt tcaagagaat | 1980 |
| taaatcgttt at | 1992 |

<210> SEQ ID NO 12
<211> LENGTH: 1767
<212> TYPE: DNA
<213> ORGANISM: Homo sapiens

<400> SEQUENCE: 12

| | |
|---|---|
| gggttgaact gcgggctgga gaaggaaaac cctttgacaa ttttgagaat tcagcatgtt | 60 |
| aaagtaacac accattggaa ggtggtcgct acagcaaatt tggatgagat cattaattac | 120 |
| aattttaatg agcagaaaac agaaataaac gcaataaatg gctcaagaat aaaatttgat | 180 |
| cagcaccacc gacggatgga gtttagctat tggtgtcaaa gcgctcattt gggtccaagc | 240 |
| acgaaaagcc aggagggcgt actccgcttc gataaccttc gtttactaag cactagtttt | 300 |
| taagggtcag cttgagtttg agtctgaaac tgggggaagg aagggttata tttgccagtt | 360 |
| ttatttcctt ctaagataga agcaatgtta ttttggtcctc ctcttccttt atctttcttc | 420 |
| attaacttca agactggttt aaatctatta tttcatggac tttagaatct gacctggggt | 480 |
| aaggtgaagt ccttcgtcag catgaatagt gctaaggagt caagccaaga cttgcttcag | 540 |
| aagagagctg atgtgcggac cttctgcatt tccacgcggg gatccagtgc ttgggtctaa | 600 |
| accccagcgc cctgccacct cggcaggaa gctgcgggag gatggtggca ggcatagccc | 660 |
| gtcctagcct tgaaactggg gggcctatgt ctctggcttc gttacaaacg aaacgtttct | 720 |
| cgccttcgga cactccaccc tggcggtggt acccaacctt cagtctccac tctgcgcctg | 780 |
| gccctccagc gacctcctca catcctccag gacactgcat tctcaaggac taggtaggaa | 840 |
| ttgggaggaa aagaggccag tcatcccaa agattccaat gttaaagagt gatccccttt | 900 |
| ttatctcatg taaatattat gactcggaag agagttgaat atttccctat tgagaatgtt | 960 |
| agtatctact attggaggcg gggttgccaa agagagacac gggggtgggg gagagattga | 1020 |
| gactgagatt caactcaatc caactcaggg tgaactgtct tgagtaaata gttgcaacgc | 1080 |
| ttggtgtaag gatgtctcca tcgttcactt ttacgtatca tttgcattgc caaattaaaa | 1140 |
| tggcagcatt gttcttaatt atgacaataa aaaattccgg atccgtgtac cttgatccct | 1200 |
| ggtagtgagg gggtgagccc cgggtgctcg atcccgcgta gagcagcgtg tattgcagac | 1260 |
| gcacgctggg cagcacggga aggcaggccg gtgcctcctg ccaggtgcta gttgtagtgg | 1320 |
| atctgctgcc tgtctacagc tgggagcggt gacaacgatg gagcgtcctc ggagagggtg | 1380 |
| ggctgccccc tgtcactccc ggggaagat cgccctgccc tccgctctaa ctgcgtggtt | 1440 |

-continued

```
gaaaccagtt tcgggacccg agtcctggtc ccgctgacgc gggaggcttg tttctggtgg      1500
ggcagtctta acgcattgcc ttcagatgcc tttgagagtc aggacttgct ctttcttggg      1560
gatcctccga aaccagcatg ccttcctgcc cacgacctaa taaagtggga ctttttcaag      1620
taccccttgg gagtggacgt gtaacacgtg gtcgcaagga tcccggcgca tctctacgca      1680
gtatatctaa tggggatggg ggggctctgt ttgaaagcaa atgatttgca ttttaattga      1740
aaaataaatg aaagcggttt ggcaaat                                          1767
```

<210> SEQ ID NO 13
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 13
tcctctctcc caacccact                                                   19

<210> SEQ ID NO 14
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 14
tgtctcggct ctccactcct                                                  20

<210> SEQ ID NO 15
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 15
cattccttcc acaattcgcc t                                                21

<210> SEQ ID NO 16
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 16
gttcctcccg tgcctttag                                                   19

<210> SEQ ID NO 17
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 17
acctatagta cacgcccagc a                                                21

<210> SEQ ID NO 18
<211> LENGTH: 20
<212> TYPE: DNA
<213> ORGANISM: Artificial Sequence
<220> FEATURE:

<223> OTHER INFORMATION: Antisense oligonucleotide

<400> SEQUENCE: 18
gcttctgccc aggtgtgaca                                                   20

<210> SEQ ID NO 19
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 19
cagcaagtgt cagatccca                                                    19

<210> SEQ ID NO 20
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 20
agtgtcagat cccagctcca g                                                 21

<210> SEQ ID NO 21
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 21
ggagtttggt cagtggttgg g                                                 21

<210> SEQ ID NO 22
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 22
gtgtcagatc ccagctccag                                                   20

<210> SEQ ID NO 23
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 23
ctcgttacct cttgtcctgg g                                                 21

<210> SEQ ID NO 24
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 24
agtcgggagg gcttgggtta                                                   20

```
<210> SEQ ID NO 25
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 25
ccctgcttcc ttctgtgtct                                               20

<210> SEQ ID NO 26
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 26
gccaccctgc ttccttctgt                                               20

<210> SEQ ID NO 27
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 27
tcctgcttcc tcggctctca                                               20

<210> SEQ ID NO 28
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 28
cctccatgtc ctgccctcaa                                               20

<210> SEQ ID NO 29
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 29
tccgtctcct ccattagtcc a                                             21

<210> SEQ ID NO 30
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 30
tccgtctcct ccattagtcc                                               20

<210> SEQ ID NO 31
<211> LENGTH: 21
<212> TYPE: DNA
<213> ORGANISM: Artificial Sequence
<220> FEATURE:
<223> OTHER INFORMATION: Antisense oligonucleotide
```

```
<400> SEQUENCE: 31
gtccgtctcc tccattagtc c                                              21

<210> SEQ ID NO 32
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 32
ctaccagcat cacctcaacc c                                              21

<210> SEQ ID NO 33
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 33
agttcgaggt gaagaaggag c                                              21

<210> SEQ ID NO 34
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 34
cgctggagga tctgtactgg a                                              21

<210> SEQ ID NO 35
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 35
cctgatgaag ttcgaggtga                                                20

<210> SEQ ID NO 36
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 36
gtacgtcaac gacttcgacc t                                              21

<210> SEQ ID NO 37
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 37
gcaattgaag ctgtctccc                                                 19

<210> SEQ ID NO 38
<211> LENGTH: 19
```

```
<212> TYPE: DNA
<213> ORGANISM: Artificial Sequence
<220> FEATURE:
<223> OTHER INFORMATION: Antisense oligonucleotide

<400> SEQUENCE: 38
cggcagagaa cagaaggtc                                              19

<210> SEQ ID NO 39
<211> LENGTH: 19
<212> TYPE: DNA
<213> ORGANISM: Artificial Sequence
<220> FEATURE:
<223> OTHER INFORMATION: Antisense oligonucleotide

<400> SEQUENCE: 39
tttcaggaga tgggcgctc                                              19

<210> SEQ ID NO 40
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 40
ggagagcaat ctgagaagcg a                                           21

<210> SEQ ID NO 41
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 41
gcctctcaac gtcagagcct                                             20

<210> SEQ ID NO 42
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 42
tctcagtctc aatctctccc                                             20

<210> SEQ ID NO 43
<211> LENGTH: 21
<212> TYPE: DNA
<213> ORGANISM: Artificial Sequence
<220> FEATURE:
<223> OTHER INFORMATION: Antisense oligonucleotide

<400> SEQUENCE: 43
gttacacgtc cactcccaag g                                           21

<210> SEQ ID NO 44
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 44
```

```
gctatgcctg ccaccatcct                                                    20

<210> SEQ ID NO 45
<211> LENGTH: 20
<212> TYPE: DNA
<213> ORGANISM: Artificial Sequence
<220> FEATURE:
<223> OTHER INFORMATION: Antisense oligonucleotide

<400> SEQUENCE: 45
tttcctccca attcctacct                                                    20
```